US005710022A

United States Patent [19]
Zhu et al.

[11] Patent Number: 5,710,022
[45] Date of Patent: Jan. 20, 1998

[54] NUCLEAR MITOTIC PHOSPHOPROTEIN

[75] Inventors: Xueling Zhu, Hefei, China; Wen-Hwa Lee, San Antonio, Tex.

[73] Assignee: Board of Regents of the University of Texas System, Austin, Tex.

[21] Appl. No.: 328,254

[22] Filed: Oct. 24, 1994

Related U.S. Application Data

[63] Continuation-in-part of Ser. No. 141,239, Oct. 22, 1993, abandoned.
[51] Int. Cl.⁶ .................. C07K 14/435; C12N 1/21; C12N 15/12; C12N 15/63
[52] U.S. Cl. ............. 435/69.1; 435/252.3; 435/254.11; 435/320.1; 435/325; 435/419; 536/23.5
[58] Field of Search ................ 536/23.5; 435/320.1, 435/240.2, 252.3, 254.11, 69.1, 325, 419

[56] References Cited

FOREIGN PATENT DOCUMENTS

94/12521  6/1994  WIPO.

OTHER PUBLICATIONS

Wadhwa et al., Cell Structure & Function 19:467 (1994).
Lee et al., "RB Protein as a Cellular 'Corral' for Growth-promoting Proteins" Cold Spring Harbor Symp. Quart. Biol. LVI:211–217 (1991).
Kaelin et al.; "Identification of Cellular Proteins That Can Interact Specifically with the T/E1A–Binding Region of the Retinoblastoma Gene Product" Cell 64:521–532 (1991).
Goodrich, David W. and Lee, Wen-Hwa, "Molecular characterization of the retinoblastoma susceptibility gene" Biochem. Biophys. Acta 1155:43–61 (1993).
Weinberg, Robert A., "Tumor Suppressor Genes" Science 254:1138–1146 (1991).
Shan et al., "Molecular Cloning of Cellular Genes Encoding Retinoblastoma–Associated Proteins: Identification of a Gene with Properties of the Transcription Factor E2F" Mol. Cell. Biol. 12:5620–5631 (1992).

Helin et al., "A cDNA Encoding a pRB–binding Protein with Properties of the Transcription Factor E2F" Cell 70:337–350 (1992).

Kaelin et al., "Expression Cloning of a cDNA Encoding a Retinoblastoma–Binding Protein with E2F–like Properties" Cell 70:351–364 (1992).

Landschulz et al., "The Leucine Zipper: A Hypothetical Structure Common to a New Class of DNA Binding Proteins" Science 240:1759–1763 (1988).

Keyomarsi et al., "Synchronization of Tumor and Normal Cells from $G_1$ to Multiple Cell Cycles by Lovastatin" Cancer Res. 51:3602–3609 (1991).

(List continued on next page.)

Primary Examiner—Eric Grimes
Attorney, Agent, or Firm—Townsend & Townsend & Crew LLP

[57] ABSTRACT

A novel purified phosphoprotein designated mitosin is provided by this invention. Also provided is the amino acid sequence of mitosin, active fragments of mitosin, and a nucleic acid molecule encoding mitosin. Diagnostic and therapeutic methods of using the protein and nucleic acid molecule are also provided. The nucleic acid molecules are useful to recombinantly produce mitosin and for use as probes. The compositions and methods of this invention are based on the discovery that the intracellular presence of mitosin is necessary for the cell to enter the M phase of mitosis, and that the degradation of mitosin is necessary for the cell to advance to the next stage. Thus, an anti-mitosin antibody, or a mutant or non-functional analog of mitosin, would inhibit the mitotic cell cycle by preventing cells from entering the M phase, and overexpression of mitosin, or a functional equivalent thereof, would inhibit the cycle by preventing cells from leaving the M phase. Such overexpression could be achieved either by addition of the protein or through gene therapy, i.e., delivery of a gene encoding the protein or a functional equivalent thereof.

8 Claims, 14 Drawing Sheets

OTHER PUBLICATIONS

Earnshaw, William C. and Rothfield, Naomi, "Identification of a family of human centromere proteins using autoimmune sera from patients with scleroderma" *Chromosoma* 91:313–321 (1985).

Compton et al., "Identification of Novel Centromere/Kinetochore-associated Proteins Using Monoclonal Antibodies Generated against Human Mitotic Chromosome Scaffolds" *J. Cell Biol.* 112:1083–1097 (1991).

Yen et al., "CENP–E, a novel human centromere–associated protein required for progression from metaphase to anaphase" *EMBO J.* 10(5) :1245–1254 (1991).

Guillemot et al., "Physical linkage of a guanine nucleotide–binding protein–related gene to the chicken major histocompatibility complex" *PNAS USA* 86:4594–4598 (1989).

Buchkovich et al., "The Retinoblastoma Protein Is Phosphorylated during Specific Phases of the Cell Cycle" *Cell* 58:1097–1105 (1989).

Chen et al., "Phosphorylation of the retinoblastoma gene product is modulated during the cell cycle and cellular differentiation" *Cell* 58:1193–1198 (1989).

Shenoy et al., "Purified Maturation Promoting Factor Phosphorylates $pp60^{c-src}$ at the Sites Phosphorylated during Fibroblast Mitosis" *Cell* 57:763–774 (1989).

Feramisco et al., "Optimal Spatial Requirements for the Location of Basic Residues in Peptide Substrates for the Cyclic AMP–dependent Protein Kinase" *J. Biol. Chem.* 255(9):4240–4245 (1980).

Earnshaw et al., "Molecular Cloning of cDNA for CENP–B, the Major Human Centromere Autoantigen" *J. Cell Biol.* 104:817–829 (1987).

Glass et al., "Synthetic Peptides Corresponding to the Site Phosphorylated in 6–phosphofructo–2–kinase/Fructose–2, 6–bisphosphatase as Substrates of Cyclic Nucleotide–dependent Protein Kinases" *J. Biol. Chem.* 261(6):2987–2993 (1986).

Saitoh et al., "CENP–C, an Autoantigen in Scleroderma, Is a Component of the Human Inner Kinetochore Plate" *Cell* 70:115–125 (1992).

Yen et al., "CENP–E is a putative kinetochore motor that accumulates just before mitosis" *Nature* 359:536–539 (1992).

Durfee et al., "The retinoblastoma protein associates with the protein phosphatase type 1 catalytic subunit" *Genes& Develop.* 7:555–569 (1993).

Dingwall, Colin and Laskey, Ronald A., "Nuclear targeting sequences—a consensus?" *TIBS* 16:478–481 (1991).

Lee et al., "Human Retinoblastoma Susceptibility Gene: Cloning, Identification and Sequence" *Science* 235:1394–1399 (1987).

Kruger et al., "Nebulin as a Length Regulator of Thin Filaments of Vertebrate Skeletal Muscles: Correlation of Thin Filament Length, Nebulin Size, and Epitope Profile" *J. Cell Biol.* 115(1):97–107 (1991).

Cooper et al., "RB and the Cell Cycle: Entrance or Exit?" *Cell* 58:1009–1011 (1989).

Adams et al., "Hydroxyurea" *J. Biol. Chem.* 242:1314–1317 (1967).

Booher, Robert and Beach, David, "Involvement of a Type 1 Protein Phosphatase Encoded by bws1+ in Fission Yeast Mitotic Control" *Cell* 57:1009–1016 (1989).

Zieve et al., "Production of large numbers of mitotic mammalian cells by use of the reversible microtubule inhibitor nocodazole" *Exp. Cell Res.* 126:397–405 (1980).

Doonan, John H. and Morris, N. Ronald, "The bimG Gene of *Aspergillus nidulans*, Required for Completion of Anaphase, Encodes a Homolog of Mammalian Phosphoprotein Phosphatase 1" *Cell* 57:987–996 (1989).

Hirano et al., "A Temperature–sensitive Mutation of the *Schizosaccharomyces pombe* Gene nuc2+ That Encodes a Nuclear Scaffold–like Protein Blocks Spindle Elongation in Mitotic Anaphase" *J. Cell Biol.* 106:1171–1183 (1988).

Ludlow et al., "SV40 Large T Antigen Binds Preferentially to an Underphosphorylated Member of the Retinoblastoma Susceptibility Gene Product Family" *Cell* 56:57–65 (1989).

DeCaprio et al., "The Product of the Retinoblastoma Susceptibility Gene Has Properties of a Cell Cycle Regulatory Element" *Cell* 58:1085–1095 (1989).

Ludlow et al., "The Retinoblastoma Susceptibility Gene Product Undergoes Cell Cycle–Dependent Dephosphorylation and Binding to and Release from SV40 Large T" *Cell* 60:387–396 (1990).

Mihara et al., "Cell Cycle–dependent Regulation of Phosphorylation of the Human Retinoblastoma Gene Product" *Science* 246:1300–1303 (1989).

Landmann et al., "Prolonged Interferon–γ Application by Subcutaneous Infusion in Cancer Patients: Differential Response of Serum CD14, Neopterin and Monocyte HLA Class I and Ii Antigens" *J. Interferon Res.* 12:103–111 (1992).

Aulitzky et al., "Recombinant Tumour Necrosis Factor Alpha Administered Subcutaneously or Intramuscularly for Treatment of Advanced Malignant Disease: a Phase I Trial" *Eur. J. Cancer* 27(4):462–467 (1991).

Supersaxo et al., "Recombinant Human Interferon Alpha–2a: Delivery to Lymphoid Tissue by Selected Modes of Application" *Pharm. Res.* 5(8):472–476 (1988).

Demetri et al., "A Phase I Trial of Recombinant Human Tumor Necrosis Factor and Interferon–Gamma: Effects of Combination Cytokine Administration in Vivo" *J. Clin. Oncol.* 7(10):1545–1553 (1989).

LeMaistre et al., "Therapeutic effects of genetically engineered toxin ($DAB_{486}IL-2$) in patient with chronic lymphocytic leukaemia" *Lancet* 337:1124–1125 (1991).

Zhu et al., "Systemic Gene Expression After Intravenous DNA Delivery into Adult Mice" *Science* 261:209–211 (1993).

Riggs, P., in: *Current Protocols in Molecular Biology*, Ausebel et al. (eds.), New York, Greene Associates/Wiley Interscience, pp. 16.6.1–16.6.14 (1990).

Smith, Donald B. and Johnson, Kevin S., "Single–step purification of polypeptides expressed in *Escherichia coli* as fusions with glutathione S–transferase" *Gene* 67:31–40 (1988).

Levine, "The Tumor Suppressor Genes" *Ann. Rev. Biochem.* 62:623–651 (1993).

Lantz et al., "Infusion of tumor necrosis factor (TNF) causes an increase in circulating TNF–binding protein in humans" *Cytokine* 2:402–406 (1990).

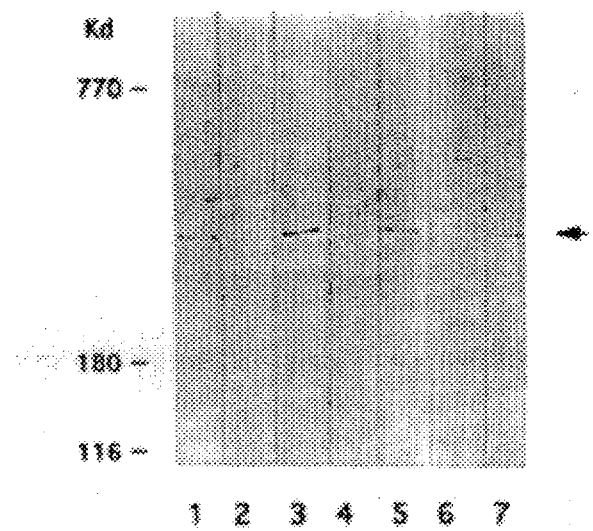
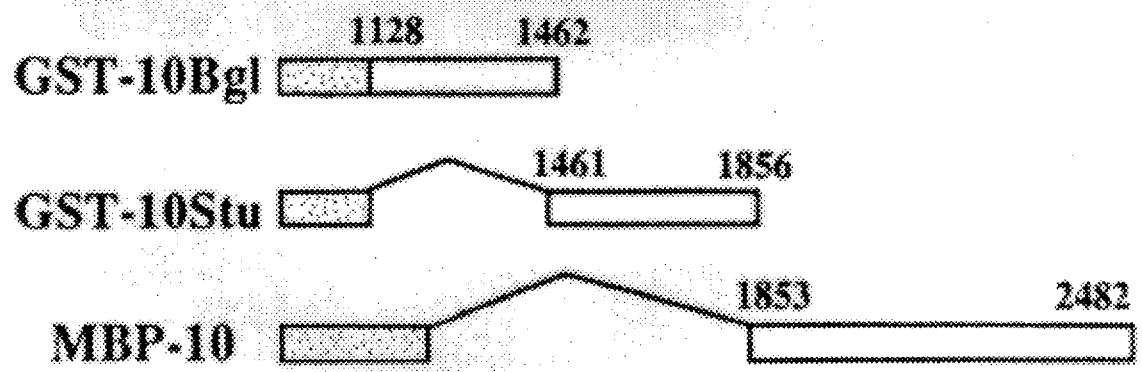
FIG. 2

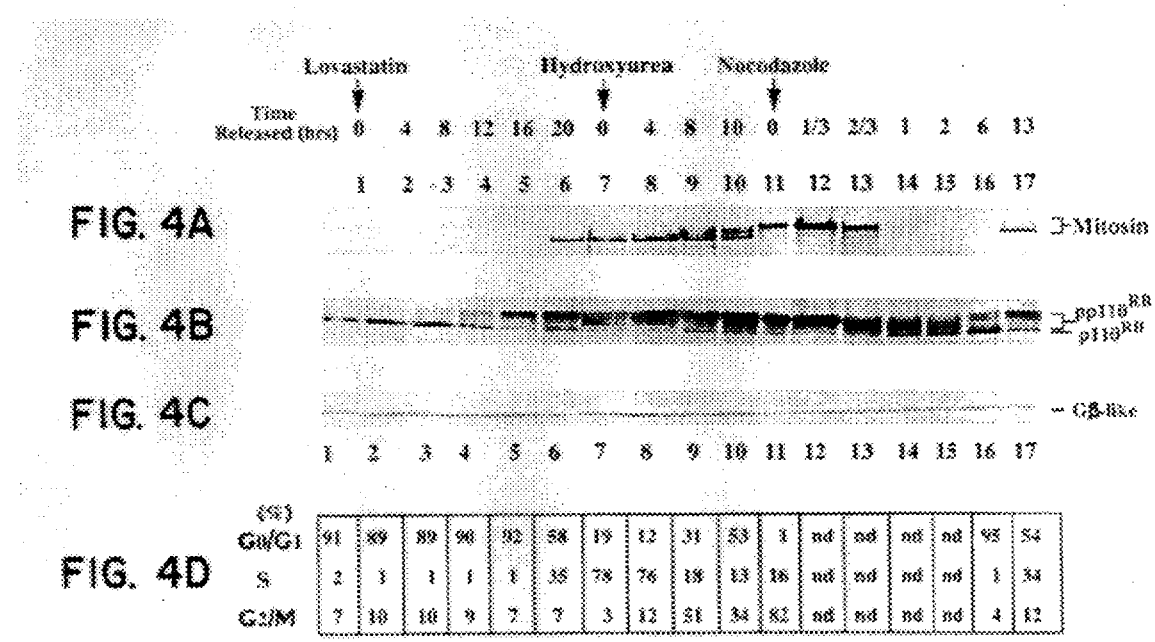

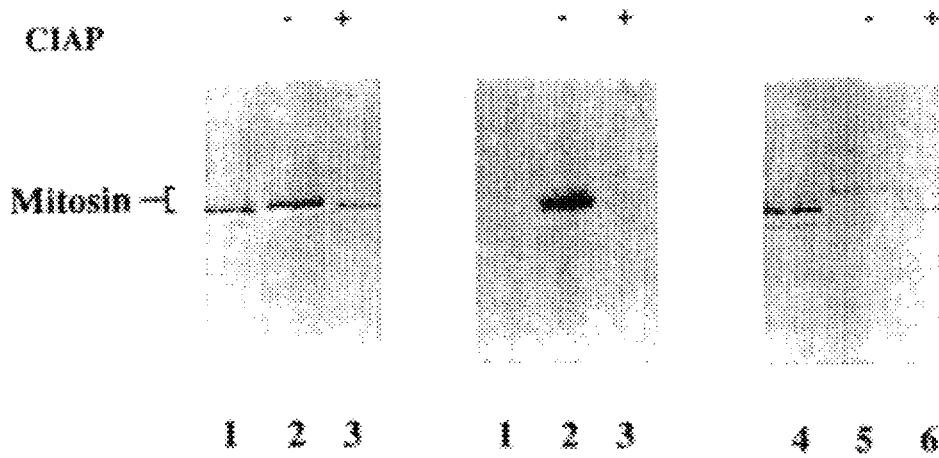
FIG. 5A    FIG. 5B    FIG. 5C
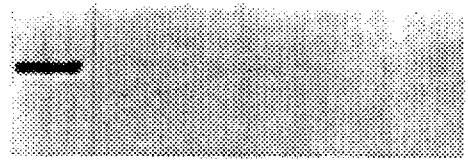
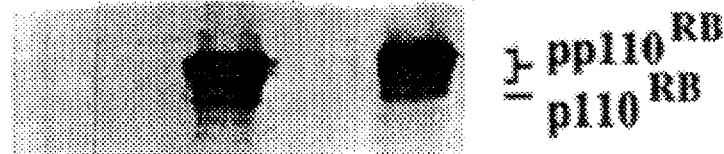

| Name | Amino acid residues | 56K$^{RB}$ Binding |
|---|---|---|
| MBP-10 | 1853-2482 | + |
| MBP-10/H | 1853-2296 | − |
| MBP-10/NB | 1853-2014 | − |
| MBP-10/KN | 2014-2482 | + |
| MBP-10/NI | 2271-2482 | + |
| GST-1045 | 2330-2375 | + |

FIG. 7C

E2F-1   439   IS LSPPHEAL DYHFGLEEGE GIRDLF DCDF GDL   471
Mitosin  2328  AVMSGIHPAE DTEGTE FEPE GLPEVVKKGF ADI   2360

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
  ( A ) LENGTH: 6 amino acids
  ( B ) TYPE: amino acid
  ( D ) TOPOLOGY: linear ( x i ) SEQUENCE DESCRIPTION: SEQ ID NO:1:

```
Ser  Thr  Pro  Xaa  Lys  Arg
1                 5
```

( 2 ) INFORMATION FOR SEQ ID NO:2:

( i ) SEQUENCE CHARACTERISTICS:
  ( A ) LENGTH: 5 amino acids
  ( B ) TYPE: amino acid
  ( D ) TOPOLOGY: linear ( x i ) SEQUENCE DESCRIPTION: SEQ ID NO:2:

```
Ser  Thr  Pro  Lys  Arg
1                 5
```

( 2 ) INFORMATION FOR SEQ ID NO:3:

( i ) SEQUENCE CHARACTERISTICS:
  ( A ) LENGTH: 33 amino acids
  ( B ) TYPE: amino acid
  ( D ) TOPOLOGY: linear ( x i ) SEQUENCE DESCRIPTION: SEQ ID NO:3:

```
Ile  Ser  Leu  Ser  Pro  Pro  His  Glu  Ala  Leu  Asp  Tyr  His  Phe  Gly  Leu
1                 5                          10                           15
Glu  Glu  Gly  Glu  Gly  Ile  Arg  Asp  Leu  Phe  Asp  Cys  Asp  Phe  Gly  Asp
                 20                          25                           30
Leu
```

( 2 ) INFORMATION FOR SEQ ID NO:4:

( i ) SEQUENCE CHARACTERISTICS:
  ( A ) LENGTH: 33 amino acids
  ( B ) TYPE: amino acid
  ( D ) TOPOLOGY: linear ( x i ) SEQUENCE DESCRIPTION: SEQ ID NO:4:

```
Ala  Val  Met  Ser  Gly  Ile  His  Pro  Ala  Glu  Asp  Thr  Glu  Gly  Thr  Glu
1                 5                          10                           15
Phe  Glu  Pro  Glu  Gly  Leu  Pro  Glu  Val  Val  Lys  Lys  Gly  Phe  Ala  Asp
                 20                          25                           30
Ile
```

( 2 ) INFORMATION FOR SEQ ID NO:5:

( i ) SEQUENCE CHARACTERISTICS:
  ( A ) LENGTH: 8789 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
    ( A ) NAME/KEY: CDS
    ( B ) LOCATION: 544..7990

( x i ) SEQUENCE DESCRIPTION: SEQ ID NO:5:

```
GGCCGCATAG GATGCCCAGC CATAGTTGAA TCTCAGATAA ACAATGAATA ATATTTTCAT        60

ACAGTATGCC TCAATTATTA CATGGGACAC ACTCATACCA AAAATTATTT TAGATTCTAT       120

AGGGTGTCTT GTATTTTATG TGCCAATCCG ATCAATGTGA AGATTCAACA GGTGCATTTC       180

TTGGAAGAGA GAAAGTGGGG TTGGCCTTGA GCAGGAGAAG GTTGAGAAGG AAGGGCTGGT       240

GGCCACAGAA AGAGAGGTGG CCTCAAAGAC ATCCATGAAG ATAAGCCAAC AAGGACATCA       300

GGGTGCCTGC TCCTGACCCC ACTCCAGGGA GGAGGCTGGG AAGCACTGCC CTTCCTCCCC       360

GTACCCACTC ACGACCCAG ATTCTGGCCT GTGCTTCAGG GGCTTTGTGA GCATGTGCAG        420

CTTTTCTTCT TCTTCTTCCT CTTCCTCTCT TTAGAGTTAA AAAAGAAAGA ATATGAAGAA       480

TTGAAAGAAG AGAAAACTCT GTTTTCTTGT TGGAAAAGTG AAAACGAAAA ACTTTTAACT       540
```

| | | | | | | | | | | | | | | | |
|---|---|---|---|---|---|---|---|---|---|---|---|---|---|---|---|
| CAG | ATG | GAA | TCA | GAA | AAG | GAA | AAC | TTG | CAG | AGT | AAA | ATT | AAT | CAC | TTG | 588
| | Met | Glu | Ser | Glu | Lys | Glu | Asn | Leu | Gln | Ser | Lys | Ile | Asn | His | Leu |
| | 1 | | | 5 | | | | | 10 | | | | | | 15 |

| GAA | ACT | TGT | CTG | AAG | ACA | CAG | CAA | ATA | AAA | AGT | CAT | GAA | TAC | AAC | GAG | 636
| Glu | Thr | Cys | Leu | Lys | Thr | Gln | Gln | Ile | Lys | Ser | His | Glu | Tyr | Asn | Glu |
| | | | | 20 | | | | | 25 | | | | | 30 | |

| AGA | GTA | AGA | ACG | CTG | GAG | ATG | GAC | AGA | GAA | AAC | CTA | AGT | GTC | GAG | ATC | 684
| Arg | Val | Arg | Thr | Leu | Glu | Met | Asp | Arg | Glu | Asn | Leu | Ser | Val | Glu | Ile |
| | | | 35 | | | | | 40 | | | | | 45 | | |

| AGA | AAC | CTT | CAC | AAC | GTG | TTA | GAC | AGT | AAG | TCA | GTG | GAG | GTA | GAG | ACC | 732
| Arg | Asn | Leu | His | Asn | Val | Leu | Asp | Ser | Lys | Ser | Val | Glu | Val | Glu | Thr |
| | | 50 | | | | | 55 | | | | | 60 | | | |

| CAG | AAA | CTA | GCT | TAT | ATG | GAG | CTA | CAG | CAG | AAA | GCT | GAG | TTC | TCA | GAT | 780
| Gln | Lys | Leu | Ala | Tyr | Met | Glu | Leu | Gln | Gln | Lys | Ala | Glu | Phe | Ser | Asp |
| 65 | | | | | 70 | | | | | 75 | | | | | |

| CAG | AAA | CAT | CAG | AAG | GAA | ATA | GAA | AAT | ATG | TGT | TTG | AAG | ACT | TCT | CAG | 828
| Gln | Lys | His | Gln | Lys | Glu | Ile | Glu | Asn | Met | Cys | Leu | Lys | Thr | Ser | Gln |
| 80 | | | | 85 | | | | | 90 | | | | | 95 | |

| CTT | ACT | GGG | CAA | GTT | GAA | GAT | CTA | GAA | CAC | AAG | CTT | CAG | TTA | CTG | TCA | 876
| Leu | Thr | Gly | Gln | Val | Glu | Asp | Leu | Glu | His | Lys | Leu | Gln | Leu | Leu | Ser |
| | | | | 100 | | | | | 105 | | | | | 110 | |

| AAT | GAA | ATA | ATG | GAC | AAA | GAC | CGG | TGT | TAC | CAA | GAC | TTG | CAT | GCC | GAA | 924
| Asn | Glu | Ile | Met | Asp | Lys | Asp | Arg | Cys | Tyr | Gln | Asp | Leu | His | Ala | Glu |
| | | | 115 | | | | | 120 | | | | | 125 | | |

| TAT | GAG | AGC | CTC | AGG | GAT | CTG | CTA | AAA | TCC | AAA | GAT | GCT | TCT | CTG | GTG | 972
| Tyr | Glu | Ser | Leu | Arg | Asp | Leu | Leu | Lys | Ser | Lys | Asp | Ala | Ser | Leu | Val |
| | | 130 | | | | | 135 | | | | | 140 | | | |

| ACA | AAT | GAA | GAT | CAT | CAG | AGA | AGT | CTT | TTG | GCT | TTT | GAT | CAG | CAG | CCT | 1020
| Thr | Asn | Glu | Asp | His | Gln | Arg | Ser | Leu | Leu | Ala | Phe | Asp | Gln | Gln | Pro |
| | 145 | | | | 150 | | | | | 155 | | | | | |

| GCC | ATG | CAT | CAT | TCC | TTT | GCA | AAT | ATA | ATT | GGA | GAA | CAA | GGA | AGC | ATG | 1068
| Ala | Met | His | His | Ser | Phe | Ala | Asn | Ile | Ile | Gly | Glu | Gln | Gly | Ser | Met |
| 160 | | | | | 165 | | | | | 170 | | | | | 175 |

| CCT | TCA | GAG | AGG | AGT | GAA | TGT | CGT | TTA | GAA | GCA | GAC | CAA | AGT | CCG | AAA | 1116
| Pro | Ser | Glu | Arg | Ser | Glu | Cys | Arg | Leu | Glu | Ala | Asp | Gln | Ser | Pro | Lys |
| | | | 180 | | | | | 185 | | | | | 190 | | |

| AAT | TCT | GCC | ATC | CTA | CAA | AAT | AGA | GTT | GAT | TCA | CTT | GAA | TTT | TCA | TTA | 1164
| Asn | Ser | Ala | Ile | Leu | Gln | Asn | Arg | Val | Asp | Ser | Leu | Glu | Phe | Ser | Leu |
| | | | 195 | | | | | 200 | | | | | 205 | | |

| GAG | TCT | CAA | AAA | CAG | ATG | AAC | TCA | GAC | CTG | CAA | AAG | CAG | TGT | GAA | GAG | 1212
| Glu | Ser | Gln | Lys | Gln | Met | Asn | Ser | Asp | Leu | Gln | Lys | Gln | Cys | Glu | Glu |
| | | 210 | | | | | 215 | | | | | 220 | | | |

| | | | | | | | | | | | | | | | | |
|---|---|---|---|---|---|---|---|---|---|---|---|---|---|---|---|---|
| TTG | GTG | CAA | ATC | AAA | GGA | GAA | ATA | GAA | GAA | AAT | CTC | ATG | AAA | GCA | GAA | 1260 |
| Leu | Val | Gln | Ile | Lys | Gly | Glu | Ile | Glu | Glu | Asn | Leu | Met | Lys | Ala | Glu | |
| | 225 | | | | 230 | | | | | 235 | | | | | | |
| CAG | ATG | CAT | CAA | AGT | TTT | GTG | GCT | GAA | ACA | AGT | CAG | CGC | ATT | AGT | AAG | 1308 |
| Gln | Met | His | Gln | Ser | Phe | Val | Ala | Glu | Thr | Ser | Gln | Arg | Ile | Ser | Lys | |
| 240 | | | | | 245 | | | | | 250 | | | | | 255 | |
| TTA | CAG | GAA | GAC | ACT | TCT | GCT | CAC | CAG | AAT | GTT | GTT | GCT | GAA | ACC | TTA | 1356 |
| Leu | Gln | Glu | Asp | Thr | Ser | Ala | His | Gln | Asn | Val | Val | Ala | Glu | Thr | Leu | |
| | | | | 260 | | | | | 265 | | | | | 270 | | |
| AGT | GCC | CTT | GAG | AAC | AAG | GAA | AAA | GAG | CTG | CAA | CTT | TTA | AAT | GAT | AAG | 1404 |
| Ser | Ala | Leu | Glu | Asn | Lys | Glu | Lys | Glu | Leu | Gln | Leu | Leu | Asn | Asp | Lys | |
| | | | 275 | | | | | 280 | | | | | 285 | | | |
| GTA | GAA | ACT | GAG | CAG | GCA | GAG | ATT | CAA | GAA | TTA | AAA | AAG | AGC | AAC | CAT | 1452 |
| Val | Glu | Thr | Glu | Gln | Ala | Glu | Ile | Gln | Glu | Leu | Lys | Lys | Ser | Asn | His | |
| | | | 290 | | | | | 295 | | | | | 300 | | | |
| CTA | CTT | GAA | GAC | TCT | CTA | AAG | GAG | CTA | CAA | CTT | TTA | TCC | GAA | ACC | CTA | 1500 |
| Leu | Leu | Glu | Asp | Ser | Leu | Lys | Glu | Leu | Gln | Leu | Leu | Ser | Glu | Thr | Leu | |
| | 305 | | | | | 310 | | | | | 315 | | | | | |
| AGC | TTG | GAG | AAG | AAA | GAA | ATG | AGT | TCC | ATC | ATT | TCT | CTA | AAT | AAA | AGG | 1548 |
| Ser | Leu | Glu | Lys | Lys | Glu | Met | Ser | Ser | Ile | Ile | Ser | Leu | Asn | Lys | Arg | |
| 320 | | | | | 325 | | | | | 330 | | | | | 335 | |
| GAA | ATT | GAA | GAG | CTG | ACC | CAA | GAG | AAT | GGG | ACT | CTT | AAG | GAA | ATT | AAT | 1596 |
| Glu | Ile | Glu | Glu | Leu | Thr | Gln | Glu | Asn | Gly | Thr | Leu | Lys | Glu | Ile | Asn | |
| | | | | 340 | | | | | 345 | | | | | 350 | | |
| GCA | TCC | TTA | AAT | CAA | GAG | AAG | ATG | AAC | TTA | ATC | CAG | AAA | AGT | GAG | AGT | 1644 |
| Ala | Ser | Leu | Asn | Gln | Glu | Lys | Met | Asn | Leu | Ile | Gln | Lys | Ser | Glu | Ser | |
| | | | 355 | | | | | 360 | | | | | 365 | | | |
| TTT | GCA | AAC | TAT | ATA | GAT | GAA | AGG | GAG | AAA | AGC | ATT | TCA | GAG | TTA | TCT | 1692 |
| Phe | Ala | Asn | Tyr | Ile | Asp | Glu | Arg | Glu | Lys | Ser | Ile | Ser | Glu | Leu | Ser | |
| | | 370 | | | | | 375 | | | | | 380 | | | | |
| GAT | CAG | TAC | AAG | CAA | GAA | AAA | CTT | ATT | TTA | CTA | CAA | AGA | TGT | GAA | GAA | 1740 |
| Asp | Gln | Tyr | Lys | Gln | Glu | Lys | Leu | Ile | Leu | Leu | Gln | Arg | Cys | Glu | Glu | |
| 385 | | | | | 390 | | | | | 395 | | | | | | |
| ACC | GGA | AAT | GCA | TAT | GAG | GAT | CTT | AGT | CAA | AAA | TAC | AAA | GCA | GCA | CAG | 1788 |
| Thr | Gly | Asn | Ala | Tyr | Glu | Asp | Leu | Ser | Gln | Lys | Tyr | Lys | Ala | Ala | Gln | |
| 400 | | | | | 405 | | | | | 410 | | | | | 415 | |
| GAA | AAG | AAT | TCT | AAA | TTA | GAA | TGC | TTG | CTA | AAT | GAA | TGC | ACT | AGT | CTT | 1836 |
| Glu | Lys | Asn | Ser | Lys | Leu | Glu | Cys | Leu | Leu | Asn | Glu | Cys | Thr | Ser | Leu | |
| | | | | 420 | | | | | 425 | | | | | 430 | | |
| TGT | GAA | AAT | AGG | AAA | AAT | GAG | TTG | GAA | CAG | CTA | AAG | GAA | GCA | TTT | GCA | 1884 |
| Cys | Glu | Asn | Arg | Lys | Asn | Glu | Leu | Glu | Gln | Leu | Lys | Glu | Ala | Phe | Ala | |
| | | | 435 | | | | | 440 | | | | | 445 | | | |
| AAG | GAA | CAC | CAA | GAA | TTC | TTA | ACA | AAA | TTA | GCA | TTT | GCT | GAA | GAA | AGA | 1932 |
| Lys | Glu | His | Gln | Glu | Phe | Leu | Thr | Lys | Leu | Ala | Phe | Ala | Glu | Glu | Arg | |
| | | 450 | | | | | 455 | | | | | 460 | | | | |
| AAT | CAG | AAT | CTG | ATG | CTA | GAG | TTG | GAG | ACA | GTG | CAG | CAA | GCT | CTG | AGA | 1980 |
| Asn | Gln | Asn | Leu | Met | Leu | Glu | Leu | Glu | Thr | Val | Gln | Gln | Ala | Leu | Arg | |
| | 465 | | | | | 470 | | | | | 475 | | | | | |
| TCT | GAG | ATG | ACA | GAT | AAC | CAA | AAC | AAT | TCT | AAG | AGC | GAG | GCT | GGT | GGT | 2028 |
| Ser | Glu | Met | Thr | Asp | Asn | Gln | Asn | Asn | Ser | Lys | Ser | Glu | Ala | Gly | Gly | |
| 480 | | | | | 485 | | | | | 490 | | | | | 495 | |
| TTA | AAG | CAA | GAA | ATC | ATG | ACT | TTA | AAG | GAA | GAA | CAA | AAC | AAA | ATG | CAA | 2076 |
| Leu | Lys | Gln | Glu | Ile | Met | Thr | Leu | Lys | Glu | Glu | Gln | Asn | Lys | Met | Gln | |
| | | | | 500 | | | | | 505 | | | | | 510 | | |
| AAG | GAA | GTT | AAT | GAC | TTA | TTA | CAA | GAG | AAT | GAA | CAG | CTG | ATG | AAG | GTA | 2124 |
| Lys | Glu | Val | Asn | Asp | Leu | Leu | Gln | Glu | Asn | Glu | Gln | Leu | Met | Lys | Val | |
| | | | 515 | | | | | 520 | | | | | 525 | | | |
| ATG | AAG | ACT | AAA | CAT | GAA | TGT | CAA | AAT | CTA | GAA | TCA | GAA | CCA | ATT | AGG | 2172 |
| Met | Lys | Thr | Lys | His | Glu | Cys | Gln | Asn | Leu | Glu | Ser | Glu | Pro | Ile | Arg | |
| | | 530 | | | | | 535 | | | | | 540 | | | | |

| | | | | | | | | | | | | | | | | |
|---|---|---|---|---|---|---|---|---|---|---|---|---|---|---|---|---|
| AAC | TCT | GTG | AAA | GAA | AGA | GAG | AGT | GAG | AGA | AAT | CAA | TGT | AAT | TTT | AAA | 2220 |
| Asn | Ser | Val | Lys | Glu | Arg | Glu | Ser | Glu | Arg | Asn | Gln | Cys | Asn | Phe | Lys | |
| | 545 | | | | 550 | | | | | 555 | | | | | | |
| CCT | CAG | ATG | GAT | CTT | GAA | GTT | AAA | GAA | ATT | TCT | CTA | GAT | AGT | TAT | AAT | 2268 |
| Pro | Gln | Met | Asp | Leu | Glu | Val | Lys | Glu | Ile | Ser | Leu | Asp | Ser | Tyr | Asn | |
| 560 | | | | | 565 | | | | 570 | | | | | | 575 | |
| GCG | CAG | TTG | GTG | CAA | TTA | GAA | GCT | ATG | CTA | AGA | AAT | AAG | GAA | TTA | AAA | 2316 |
| Ala | Gln | Leu | Val | Gln | Leu | Glu | Ala | Met | Leu | Arg | Asn | Lys | Glu | Leu | Lys | |
| | | | | 580 | | | | | 585 | | | | | 590 | | |
| CTT | CAG | GAA | AGT | GAG | AAG | GAG | AAG | GAG | TGC | CTG | CAG | CAT | GAA | TTA | CAG | 2364 |
| Leu | Gln | Glu | Ser | Glu | Lys | Glu | Lys | Glu | Cys | Leu | Gln | His | Glu | Leu | Gln | |
| | | | 595 | | | | 600 | | | | | 605 | | | | |
| ACA | ATT | AGA | GGA | GAT | CTT | GAA | ACC | AGC | AAT | TTG | CAA | GAC | ATG | CAG | TCA | 2412 |
| Thr | Ile | Arg | Gly | Asp | Leu | Glu | Thr | Ser | Asn | Leu | Gln | Asp | Met | Gln | Ser | |
| | | 610 | | | | 615 | | | | | 620 | | | | | |
| CAA | GAA | ATT | AGT | GGC | CTT | AAA | GAC | TGT | GAA | ATA | GAT | GCG | GAA | GAA | AAG | 2460 |
| Gln | Glu | Ile | Ser | Gly | Leu | Lys | Asp | Cys | Glu | Ile | Asp | Ala | Glu | Glu | Lys | |
| 625 | | | | | 630 | | | | | 635 | | | | | | |
| TAT | ATT | TCA | GGG | CCT | CAT | GAG | TTG | TCA | ACA | AGT | CAA | AAC | GAC | AAT | GCA | 2508 |
| Tyr | Ile | Ser | Gly | Pro | His | Glu | Leu | Ser | Thr | Ser | Gln | Asn | Asp | Asn | Ala | |
| 640 | | | | | 645 | | | | | 650 | | | | | 655 | |
| CAC | CTT | CAG | TGC | TCT | CTG | CAA | ACA | ACA | ATG | AAC | AAG | CTG | AAT | GAG | CTA | 2556 |
| His | Leu | Gln | Cys | Ser | Leu | Gln | Thr | Thr | Met | Asn | Lys | Leu | Asn | Glu | Leu | |
| | | | | 660 | | | | | 665 | | | | | 670 | | |
| GAG | AAA | ATA | TGT | GAA | ATA | CTG | CAG | GCT | GAA | AAG | TAT | GAA | CTC | GTA | ACT | 2604 |
| Glu | Lys | Ile | Cys | Glu | Ile | Leu | Gln | Ala | Glu | Lys | Tyr | Glu | Leu | Val | Thr | |
| | | | 675 | | | | | 680 | | | | | 685 | | | |
| GAG | CTG | AAT | GAT | TCA | AGG | TCA | GAA | TGT | ATC | ACA | GCA | ACT | AGG | AAA | ATG | 2652 |
| Glu | Leu | Asn | Asp | Ser | Arg | Ser | Glu | Cys | Ile | Thr | Ala | Thr | Arg | Lys | Met | |
| | | 690 | | | | 695 | | | | | 700 | | | | | |
| GCA | GAA | GAG | GTA | GGG | AAA | CTA | CTA | AAT | GAA | GTT | AAA | ATA | TTA | AAT | GAT | 2700 |
| Ala | Glu | Glu | Val | Gly | Lys | Leu | Leu | Asn | Glu | Val | Lys | Ile | Leu | Asn | Asp | |
| 705 | | | | | 710 | | | | | 715 | | | | | | |
| GAC | AGT | GGT | CTT | CTC | CAT | GGT | GAG | TTA | GTG | GAA | GAC | ATA | CCA | GGA | GGT | 2748 |
| Asp | Ser | Gly | Leu | Leu | His | Gly | Glu | Leu | Val | Glu | Asp | Ile | Pro | Gly | Gly | |
| 720 | | | | | 725 | | | | | 730 | | | | | 735 | |
| GAA | TTT | GGT | GAA | CAA | CCA | AAT | GAA | CAG | CAC | CCT | GTG | TCT | TTG | GCT | CCA | 2796 |
| Glu | Phe | Gly | Glu | Gln | Pro | Asn | Glu | Gln | His | Pro | Val | Ser | Leu | Ala | Pro | |
| | | | | 740 | | | | | 745 | | | | | 750 | | |
| TTG | GAC | GAG | AGT | AAT | TCC | TAC | GAG | CAC | TTG | ACA | TTG | TCA | GAC | AAA | GAA | 2844 |
| Leu | Asp | Glu | Ser | Asn | Ser | Tyr | Glu | His | Leu | Thr | Leu | Ser | Asp | Lys | Glu | |
| | | | 755 | | | | 760 | | | | | 765 | | | | |
| GTT | CAA | ATG | CAC | TTT | GCC | GAA | TTG | CAA | GAG | AAA | TTC | TTA | TCT | TTA | CAA | 2892 |
| Val | Gln | Met | His | Phe | Ala | Glu | Leu | Gln | Glu | Lys | Phe | Leu | Ser | Leu | Gln | |
| | | 770 | | | | 775 | | | | | 780 | | | | | |
| AGT | GAA | CAC | AAA | ATT | TTA | CAT | GAT | CAG | CAC | TGT | CAG | ATG | AGC | TCT | AAA | 2940 |
| Ser | Glu | His | Lys | Ile | Leu | His | Asp | Gln | His | Cys | Gln | Met | Ser | Ser | Lys | |
| 785 | | | | | 790 | | | | | 795 | | | | | | |
| ATG | TCA | GAG | CTG | CAG | ACC | TAT | GTT | GAC | TCA | TTA | AAG | GCC | GAA | AAT | TTG | 2988 |
| Met | Ser | Glu | Leu | Gln | Thr | Tyr | Val | Asp | Ser | Leu | Lys | Ala | Glu | Asn | Leu | |
| 800 | | | | | 805 | | | | | 810 | | | | | 815 | |
| GTC | TTG | TCA | ACG | AAT | CTG | AGA | AAC | TTT | CAA | GGT | GAC | TTG | GTG | AAG | GAG | 3036 |
| Val | Leu | Ser | Thr | Asn | Leu | Arg | Asn | Phe | Gln | Gly | Asp | Leu | Val | Lys | Glu | |
| | | | | 820 | | | | | 825 | | | | | 830 | | |
| ATG | CAG | CTG | GGC | TTG | GAG | GAG | GGG | CTC | GTT | CCA | TCC | CTG | TCA | TCC | TCT | 3084 |
| Met | Gln | Leu | Gly | Leu | Glu | Glu | Gly | Leu | Val | Pro | Ser | Leu | Ser | Ser | Ser | |
| | | | 835 | | | | 840 | | | | | 845 | | | | |
| TGT | GTG | CCT | GAC | AGC | TCT | AGT | CTT | AGC | AGT | TTG | GGA | GAC | TCC | TCC | TTT | 3132 |
| Cys | Val | Pro | Asp | Ser | Ser | Ser | Leu | Ser | Ser | Leu | Gly | Asp | Ser | Ser | Phe | |
| | | 850 | | | | 855 | | | | | 860 | | | | | |

| | | | | | | | | | | | | | | | | |
|---|---|---|---|---|---|---|---|---|---|---|---|---|---|---|---|---|
| TAC | AGA | GCT | CTT | TTA | GAA | CAG | ACA | GGA | GAT | ATG | TCT | CTT | TTG | AGT | AAT | 3180 |
| Tyr | Arg | Ala | Leu | Leu | Glu | Gln | Thr | Gly | Asp | Met | Ser | Leu | Leu | Ser | Asn | |
| 865 | | | | | 870 | | | | | 875 | | | | | | |
| TTA | GAA | GGG | GCT | GTT | TCA | GCA | AAC | CAG | TGC | AGT | GTA | GAT | GAA | GTA | TTT | 3228 |
| Leu | Glu | Gly | Ala | Val | Ser | Ala | Asn | Gln | Cys | Ser | Val | Asp | Glu | Val | Phe | |
| 880 | | | | | 885 | | | | | 890 | | | | | 895 | |
| TGC | AGC | AGT | CTG | CAG | GAG | GAG | AAT | CTG | ACC | AGG | AAA | GAA | ACC | CCT | TCG | 3276 |
| Cys | Ser | Ser | Leu | Gln | Glu | Glu | Asn | Leu | Thr | Arg | Lys | Glu | Thr | Pro | Ser | |
| | | | | 900 | | | | | 905 | | | | | 910 | | |
| GCC | CCA | GCG | AAG | GGT | GTT | GAA | GAG | CTT | GAG | TCC | CTC | TGT | GAG | GTG | TAC | 3324 |
| Ala | Pro | Ala | Lys | Gly | Val | Glu | Glu | Leu | Glu | Ser | Leu | Cys | Glu | Val | Tyr | |
| | | | 915 | | | | | 920 | | | | | 925 | | | |
| CGG | CAG | TCC | CTC | GAG | AAG | CTA | GAA | GAG | AAA | ATG | GAA | AGT | CAA | GGG | ATT | 3372 |
| Arg | Gln | Ser | Leu | Glu | Lys | Leu | Glu | Glu | Lys | Met | Glu | Ser | Gln | Gly | Ile | |
| | | | 930 | | | | | 935 | | | | | 940 | | | |
| ATG | AAA | AAT | AAG | GAA | ATT | CAA | GAG | CTC | GAG | CAG | TTA | TTA | AGT | TCT | GAA | 3420 |
| Met | Lys | Asn | Lys | Glu | Ile | Gln | Glu | Leu | Glu | Gln | Leu | Leu | Ser | Ser | Glu | |
| 945 | | | | | 950 | | | | | 955 | | | | | | |
| AGG | CAA | GAG | CTT | GAC | TGC | CTT | AGG | AAG | CAG | TAT | TTG | TCA | GAA | AAT | GAA | 3468 |
| Arg | Gln | Glu | Leu | Asp | Cys | Leu | Arg | Lys | Gln | Tyr | Leu | Ser | Glu | Asn | Glu | |
| 960 | | | | | 965 | | | | | 970 | | | | | 975 | |
| CAG | TGG | CAA | CAG | AAG | CTG | ACA | AGC | GTG | ACT | CTG | GAG | ATG | GAG | TCC | AAG | 3516 |
| Gln | Trp | Gln | Gln | Lys | Leu | Thr | Ser | Val | Thr | Leu | Glu | Met | Glu | Ser | Lys | |
| | | | | 980 | | | | | 985 | | | | | 990 | | |
| TTG | GCG | GCA | GAA | AAG | AAA | CAG | ACG | GAA | CAA | CTG | TCA | CTT | GAG | CTG | GAA | 3564 |
| Leu | Ala | Ala | Glu | Lys | Lys | Gln | Thr | Glu | Gln | Leu | Ser | Leu | Glu | Leu | Glu | |
| | | | | 995 | | | | | 1000 | | | | | 1005 | | |
| GTA | GCA | CGA | CTC | CAG | CTA | CAA | GGT | CTG | GAC | TTA | AGT | TCT | CGG | TCT | TTG | 3612 |
| Val | Ala | Arg | Leu | Gln | Leu | Gln | Gly | Leu | Asp | Leu | Ser | Ser | Arg | Ser | Leu | |
| | | | | 1010 | | | | | 1015 | | | | | 1020 | | |
| CTT | GGC | ATC | GAC | ACA | GAA | GAT | GCT | ATT | CAA | GGC | CGA | AAT | GAG | AGC | TGT | 3660 |
| Leu | Gly | Ile | Asp | Thr | Glu | Asp | Ala | Ile | Gln | Gly | Arg | Asn | Glu | Ser | Cys | |
| | | | | 1025 | | | | | 1030 | | | | | 1035 | | |
| GAC | ATA | TCA | AAA | GAA | CAT | ACT | TCA | GAA | ACT | ACA | GAA | AGA | ACA | CCA | AAG | 3708 |
| Asp | Ile | Ser | Lys | Glu | His | Thr | Ser | Glu | Thr | Thr | Glu | Arg | Thr | Pro | Lys | |
| 1040 | | | | | 1045 | | | | | 1050 | | | | | 1055 | |
| CAT | GAT | GTT | CAT | CAG | ATT | TGT | GAT | AAA | GAT | GCT | CAG | CAG | GAC | CTC | AAT | 3756 |
| His | Asp | Val | His | Gln | Ile | Cys | Asp | Lys | Asp | Ala | Gln | Gln | Asp | Leu | Asn | |
| | | | | 1060 | | | | | 1065 | | | | | 1070 | | |
| CTA | GAC | ATT | GAG | AAA | ATA | ACT | GAG | ACT | GGT | GCA | TTG | AAA | CCC | ACA | GGA | 3804 |
| Leu | Asp | Ile | Glu | Lys | Ile | Thr | Glu | Thr | Gly | Ala | Leu | Lys | Pro | Thr | Gly | |
| | | | | 1075 | | | | | 1080 | | | | | 1085 | | |
| GAG | TGC | TCT | GGG | GAA | CAG | TCC | CCA | GAT | ACC | AAT | TAT | GAG | CCT | CCA | GGG | 3852 |
| Glu | Cys | Ser | Gly | Glu | Gln | Ser | Pro | Asp | Thr | Asn | Tyr | Glu | Pro | Pro | Gly | |
| | | | | 1090 | | | | | 1095 | | | | | 1100 | | |
| GAA | GAT | AAA | ACC | CAG | GGC | TCT | TCA | GAA | TGC | ATT | TCT | GAA | TTG | TCA | TTT | 3900 |
| Glu | Asp | Lys | Thr | Gln | Gly | Ser | Ser | Glu | Cys | Ile | Ser | Glu | Leu | Ser | Phe | |
| | | | | 1105 | | | | | 1110 | | | | | 1115 | | |
| TCT | GGT | CCT | AAT | GCT | TTG | GTA | CCT | ATG | GAT | TTC | CTG | GGG | AAT | CAG | GAA | 3948 |
| Ser | Gly | Pro | Asn | Ala | Leu | Val | Pro | Met | Asp | Phe | Leu | Gly | Asn | Gln | Glu | |
| 1120 | | | | | 1125 | | | | | 1130 | | | | | 1135 | |
| GAT | ATC | CAT | AAT | CTT | CAA | CTG | CGG | GTA | AAA | GAG | ACA | TCA | AAT | GAG | AAT | 3996 |
| Asp | Ile | His | Asn | Leu | Gln | Leu | Arg | Val | Lys | Glu | Thr | Ser | Asn | Glu | Asn | |
| | | | | 1140 | | | | | 1145 | | | | | 1150 | | |
| TTG | AGA | TTA | CTT | CAT | GTG | ATA | GAG | GAC | CGT | GAC | AGA | AAA | GTT | GAA | AGT | 4044 |
| Leu | Arg | Leu | Leu | His | Val | Ile | Glu | Asp | Arg | Asp | Arg | Lys | Val | Glu | Ser | |
| | | | | 1155 | | | | | 1160 | | | | | 1165 | | |
| TTG | CTA | AAT | GAA | ATG | AAA | GAA | TTA | GAC | TCA | AAA | CTC | CAT | TTA | CAG | GAG | 4092 |
| Leu | Leu | Asn | Glu | Met | Lys | Glu | Leu | Asp | Ser | Lys | Leu | His | Leu | Gln | Glu | |
| | | | | 1170 | | | | | 1175 | | | | | 1180 | | |

| | | |
|---|---|---|
| GTA CAA CTA ATG ACC AAA ATT GAA GCA TGC ATA GAA TTG GAA AAA ATA<br>Val Gln Leu Met Thr Lys Ile Glu Ala Cys Ile Glu Leu Glu Lys Ile<br>1185                    1190                1195 | 4140 |
| GTT GGG GAA CTT AAG AAA GAA AAC TCA GAT TTA AGT GAA AAA TTG GAA<br>Val Gly Glu Leu Lys Lys Glu Asn Ser Asp Leu Ser Glu Lys Leu Glu<br>1200                    1205              1210                1215 | 4188 |
| TAT TTT TCT TGT GAT CAC CAG GAG TTA CTC CAG AGA GTA GAA ACT TCT<br>Tyr Phe Ser Cys Asp His Gln Glu Leu Leu Gln Arg Val Glu Thr Ser<br>1220                    1225              1230 | 4236 |
| GAA GGC CTC AAT TCT GAT TTA GAA ATG CAT GCA GAT AAA TCA TCA CGT<br>Glu Gly Leu Asn Ser Asp Leu Glu Met His Ala Asp Lys Ser Ser Arg<br>1235                    1240              1245 | 4284 |
| GAA GAT ATT GGA GAT AAT GTG GCC AAG GTG AAT GAC AGC TGG AAG GAG<br>Glu Asp Ile Gly Asp Asn Val Ala Lys Val Asn Asp Ser Trp Lys Glu<br>1250                    1255              1260 | 4332 |
| AGA TTT CTT GAT GTG GAA AAT GAG CTG AGT AGG ATC AGA TCG GAG AAA<br>Arg Phe Leu Asp Val Glu Asn Glu Leu Ser Arg Ile Arg Ser Glu Lys<br>1265                    1270              1275 | 4380 |
| GCT AGC ATT GAG CAT GAA GCC CTC TAC CTG GAG GCT GAC TTA GAG GTA<br>Ala Ser Ile Glu His Glu Ala Leu Tyr Leu Glu Ala Asp Leu Glu Val<br>1280                    1285              1290                1295 | 4428 |
| GTT CAA ACA GAG AAG CTA TGT TTA GAA AAA GAC AAT GAA AAT AAG CAG<br>Val Gln Thr Glu Lys Leu Cys Leu Glu Lys Asp Asn Glu Asn Lys Gln<br>1300                    1305              1310 | 4476 |
| AAG GTT ATT GTC TGC CTT GAA GAA GAA CTC TCA GTG GTC ACA AGT GAG<br>Lys Val Ile Val Cys Leu Glu Glu Glu Leu Ser Val Val Thr Ser Glu<br>1315                    1320              1325 | 4524 |
| AGA AAC CAG CTT CGT GGA GAA TTA GAT ACT ATG TCA AAA AAA ACC ACG<br>Arg Asn Gln Leu Arg Gly Glu Leu Asp Thr Met Ser Lys Lys Thr Thr<br>1330                    1335              1340 | 4572 |
| GCA CTG GAT CAG TTG TCT GAA AAA ATG AAG GAG AAA ACA CAA GAG CTT<br>Ala Leu Asp Gln Leu Ser Glu Lys Met Lys Glu Lys Thr Gln Glu Leu<br>1345                    1350              1355 | 4620 |
| GAG TCT CAT CAA AGT GAG TGT CTC CAT TGC ATT CAG GTG GCA GAG GCA<br>Glu Ser His Gln Ser Glu Cys Leu His Cys Ile Gln Val Ala Glu Ala<br>1360                    1365              1370                1375 | 4668 |
| GAG GTG AAG GAA AAG ACG GAA CTC CTT CAG ACT TTG TCC TCT GAT GTG<br>Glu Val Lys Glu Lys Thr Glu Leu Leu Gln Thr Leu Ser Ser Asp Val<br>1380                    1385              1390 | 4716 |
| AGT GAG CTG TTA AAA GAC AAA ACT CAT CTC CAG GAA AAG CTG CAG AGT<br>Ser Glu Leu Leu Lys Asp Lys Thr His Leu Gln Glu Lys Leu Gln Ser<br>1395                    1400              1405 | 4764 |
| TTG GAA AAG GAC TCA CAG GCA CTG TCT TTG ACA AAA TGT GAG CTG GAA<br>Leu Glu Lys Asp Ser Gln Ala Leu Ser Leu Thr Lys Cys Glu Leu Glu<br>1410                    1415              1420 | 4812 |
| AAC CAA ATT GCA CAA CTG AAT AAA GAG AAA GAA TTG CTT GTC AAG GAA<br>Asn Gln Ile Ala Gln Leu Asn Lys Glu Lys Glu Leu Leu Val Lys Glu<br>1425                    1430              1435 | 4860 |
| TCT GAA AGC CTG CAG GCC AGA CTG AGT GAA TCA GAT TAT GAA AAG CTG<br>Ser Glu Ser Leu Gln Ala Arg Leu Ser Glu Ser Asp Tyr Glu Lys Leu<br>1440                    1445              1450                1455 | 4908 |
| AAT GTC TCC AAG GCC TTG GAG GCC GCA CTG GTG GAG AAA GGT GAG TTC<br>Asn Val Ser Lys Ala Leu Glu Ala Ala Leu Val Glu Lys Gly Glu Phe<br>1460                    1465              1470 | 4956 |
| GCA TTG AGG CTG AGC TCA ACA CAG GAG GAA GTG CAT CAG CTG AGA AGA<br>Ala Leu Arg Leu Ser Ser Thr Gln Glu Glu Val His Gln Leu Arg Arg<br>1475                    1480              1485 | 5004 |
| GGC ATC GAG AAA CTG AGA GTT CGC ATT GAG GCC GAT GAA AAG AAG CAG<br>Gly Ile Glu Lys Leu Arg Val Arg Ile Glu Ala Asp Glu Lys Lys Gln<br>1490                    1495              1500 | 5052 |

| | |
|---|---|
| CTG CAC ATC GCA GAG AAA CTG AAA GAA CGC GAG CGG GAG AAT GAT TCA<br>Leu His Ile Ala Glu Lys Leu Lys Glu Arg Glu Arg Glu Asn Asp Ser<br>1505                    1510                    1515 | 5100 |
| CTT AAG GAT AAA GTT GAG AAC CTT GAA AGG GAA TTG CAG ATG TCA GAA<br>Leu Lys Asp Lys Val Glu Asn Leu Glu Arg Glu Leu Gln Met Ser Glu<br>1520                    1525                  1530                  1535 | 5148 |
| GAA AAC CAG GAG CTA GTG ATT CTT GAT GCC GAG AAT TCC AAA GCA GAA<br>Glu Asn Gln Glu Leu Val Ile Leu Asp Ala Glu Asn Ser Lys Ala Glu<br>1540                    1545                  1550 | 5196 |
| GTA GAG ACT CTA AAA ACA CAA ATA GAA GAG ATG GCC AGA AGC CTG AAA<br>Val Glu Thr Leu Lys Thr Gln Ile Glu Glu Met Ala Arg Ser Leu Lys<br>1555                    1560                  1565 | 5244 |
| GTT TTT GAA TTA GAC CTT GTC ACG TTA AGG TCT GAA AAA GAA AAT CTG<br>Val Phe Glu Leu Asp Leu Val Thr Leu Arg Ser Glu Lys Glu Asn Leu<br>1570                    1575                  1580 | 5292 |
| ACA AAA CAA ATA CAA GAA AAA CAA GGT CAG TTG TCA GAA CTA GAC AAG<br>Thr Lys Gln Ile Gln Glu Lys Gln Gly Gln Leu Ser Glu Leu Asp Lys<br>1585                    1590                  1595 | 5340 |
| TTA CTC TCT TCA TTT AAA AGT CTG TTA GAA GAA AAG GAG CAA GCA GAG<br>Leu Leu Ser Ser Phe Lys Ser Leu Leu Glu Glu Lys Glu Gln Ala Glu<br>1600                    1605                  1610                  1615 | 5388 |
| ATA CAG ATC AAA GAA GAA TCT AAA ACT GCA GTG GAG ATG CTT CAG AAT<br>Ile Gln Ile Lys Glu Glu Ser Lys Thr Ala Val Glu Met Leu Gln Asn<br>1620                    1625                  1630 | 5436 |
| CAG TTA AAG GAG CTA AAT GAG GCA GTA GCA GCC TTG TGT GGT GAC CAA<br>Gln Leu Lys Glu Leu Asn Glu Ala Val Ala Ala Leu Cys Gly Asp Gln<br>1635                    1640                  1645 | 5484 |
| GAA ATT ATG AAG GCC ACA GAA CAG AGT CTA GAC CCA CCA ATA GAG GAA<br>Glu Ile Met Lys Ala Thr Glu Gln Ser Leu Asp Pro Pro Ile Glu Glu<br>1650                    1655                  1660 | 5532 |
| GAG CAT CAG CTG AGA AAT AGC ATT GAA AAG CTG AGA GCC CGC CTA GAA<br>Glu His Gln Leu Arg Asn Ser Ile Glu Lys Leu Arg Ala Arg Leu Glu<br>1665                    1670                  1675 | 5580 |
| GCT GAT GAA AAG AAG CAG CTC TGT GTC TTA CAA CAA CTG AAG GAA AGT<br>Ala Asp Glu Lys Lys Gln Leu Cys Val Leu Gln Gln Leu Lys Glu Ser<br>1680                    1685                  1690                  1695 | 5628 |
| GAG CAT CAT GCA GAT TTA CTT AAG GGT AGA GTG GAG AAC CTT GAA AGA<br>Glu His His Ala Asp Leu Leu Lys Gly Arg Val Glu Asn Leu Glu Arg<br>1700                    1705                  1710 | 5676 |
| GAG CTA GAG ATA GCC AGG ACA AAC CAA GAG CAT GCA GCT CTT GAG GCA<br>Glu Leu Glu Ile Ala Arg Thr Asn Gln Glu His Ala Ala Leu Glu Ala<br>1715                    1720                  1725 | 5724 |
| GAG AAT TCC AAA GGA GAG GTA GAG ACC CTA AAA GCA AAA ATA GAA GGG<br>Glu Asn Ser Lys Gly Glu Val Glu Thr Leu Lys Ala Lys Ile Glu Gly<br>1730                    1735                  1740 | 5772 |
| ATG ACC CAA AGT CTG AGA GGT CTG GAA TTA GAT GTT GTT ACT ATA AGG<br>Met Thr Gln Ser Leu Arg Gly Leu Glu Leu Asp Val Val Thr Ile Arg<br>1745                    1750                  1755 | 5820 |
| TCA GAA AAA GAA AAT CTG ACA AAT GAA TTA CAA AAA GAG CAA GAG CGA<br>Ser Glu Lys Glu Asn Leu Thr Asn Glu Leu Gln Lys Glu Gln Glu Arg<br>1760                    1765                  1770                  1775 | 5868 |
| ATA TCT GAA TTA GAA ATA ATA AAT TCA TCA TTT GAA AAT ATT TTG CAA<br>Ile Ser Glu Leu Glu Ile Ile Asn Ser Ser Phe Glu Asn Ile Leu Gln<br>1780                    1785                  1790 | 5916 |
| GAA AAA GAG CAA GAG AAA GTA CAG ATG AAA GAA AAA TCA AGC ACT GCC<br>Glu Lys Glu Gln Glu Lys Val Gln Met Lys Glu Lys Ser Ser Thr Ala<br>1795                    1800                  1805 | 5964 |
| ATG GAG ATG CTT CAA ACA CAA TTA AAA GAG CTC AAT GAG AGA GTG GCA<br>Met Glu Met Leu Gln Thr Gln Leu Lys Glu Leu Asn Glu Arg Val Ala<br>1810                    1815                  1820 | 6012 |

| | | | | | | | | | | | | | | | | |
|---|---|---|---|---|---|---|---|---|---|---|---|---|---|---|---|---|
| GCC | CTG | CAT | AAT | GAC | CAA | GAA | GCC | TGT | AAG | GCC | AAA | GAG | CAG | AAT | CTT | 6060 |
| Ala | Leu | His | Asn | Asp | Gln | Glu | Ala | Cys | Lys | Ala | Lys | Glu | Gln | Asn | Leu | |
| | | 1825 | | | 1830 | | | | | 1835 | | | | | | |
| AGT | AGT | CAA | GTA | GAG | TGT | CTT | GAA | CTT | GAG | AAG | GCT | CAG | TTG | CTA | CAA | 6108 |
| Ser | Ser | Gln | Val | Glu | Cys | Leu | Glu | Leu | Glu | Lys | Ala | Gln | Leu | Leu | Gln | |
| 1840 | | | | 1845 | | | | 1850 | | | | | | 1855 | | |
| GGC | CTT | GAT | GAG | GCC | AAA | AAT | AAT | TAT | ATT | GTT | TTG | CAA | TCT | TCA | GTG | 6156 |
| Gly | Leu | Asp | Glu | Ala | Lys | Asn | Asn | Tyr | Ile | Val | Leu | Gln | Ser | Ser | Val | |
| | | | | 1860 | | | | | 1865 | | | | | 1870 | | |
| AAT | GGC | CTC | ATT | CAA | GAA | GTA | GAA | GAT | GGC | AAG | CAG | AAA | CTG | GAG | AAG | 6204 |
| Asn | Gly | Leu | Ile | Gln | Glu | Val | Glu | Asp | Gly | Lys | Gln | Lys | Leu | Glu | Lys | |
| | | | 1875 | | | | | 1880 | | | | | 1885 | | | |
| AAG | GAT | GAA | GAA | ATC | AGT | AGA | CTG | AAA | AAT | CAA | ATT | CAA | GAC | CAA | GAG | 6252 |
| Lys | Asp | Glu | Glu | Ile | Ser | Arg | Leu | Lys | Asn | Gln | Ile | Gln | Asp | Gln | Glu | |
| | | | 1890 | | | | | 1895 | | | | | 1900 | | | |
| CAG | CTT | GTC | TCT | AAA | CTG | TCC | CAG | GTG | GAA | GGA | GAG | CAC | CAA | CTT | TGG | 6300 |
| Gln | Leu | Val | Ser | Lys | Leu | Ser | Gln | Val | Glu | Gly | Glu | His | Gln | Leu | Trp | |
| | | 1905 | | | | | 1910 | | | | | 1915 | | | | |
| AAG | GAG | CAA | AAC | TTA | GAA | CTG | AGA | AAT | CTG | ACA | GTG | GAA | TTG | GAG | CAG | 6348 |
| Lys | Glu | Gln | Asn | Leu | Glu | Leu | Arg | Asn | Leu | Thr | Val | Glu | Leu | Glu | Gln | |
| 1920 | | | | | 1925 | | | | | 1930 | | | | | 1935 | |
| AAG | ATC | CAA | GTG | CTA | CAA | TCC | AAA | AAT | GCC | TCT | TTG | CAG | GAC | ACA | TTA | 6396 |
| Lys | Ile | Gln | Val | Leu | Gln | Ser | Lys | Asn | Ala | Ser | Leu | Gln | Asp | Thr | Leu | |
| | | | | 1940 | | | | | 1945 | | | | | 1950 | | |
| GAA | GTG | CTG | CAG | AGT | TCT | TAC | AAG | AAT | CTA | GAG | AAT | GAG | CTT | GAA | TTG | 6444 |
| Glu | Val | Leu | Gln | Ser | Ser | Tyr | Lys | Asn | Leu | Glu | Asn | Glu | Leu | Glu | Leu | |
| | | | 1955 | | | | | 1960 | | | | | 1965 | | | |
| ACA | AAA | ATG | GAC | AAA | ATG | TCC | TTT | GTT | GAA | AAA | GTA | AAC | AAA | ATG | ACT | 6492 |
| Thr | Lys | Met | Asp | Lys | Met | Ser | Phe | Val | Glu | Lys | Val | Asn | Lys | Met | Thr | |
| | | | 1970 | | | | | 1975 | | | | | 1980 | | | |
| GCA | AAG | GAA | ACT | GAG | CTG | CAG | AGG | GAA | ATG | CAT | GAG | ATG | GCA | CAG | AAA | 6540 |
| Ala | Lys | Glu | Thr | Glu | Leu | Gln | Arg | Glu | Met | His | Glu | Met | Ala | Gln | Lys | |
| | 1985 | | | | | 1990 | | | | | 1995 | | | | | |
| ACA | GCA | GAG | CTG | CAA | GAA | GAA | CTC | AGT | GGA | GAG | AAA | AAT | AGG | CTA | GCT | 6588 |
| Thr | Ala | Glu | Leu | Gln | Glu | Glu | Leu | Ser | Gly | Glu | Lys | Asn | Arg | Leu | Ala | |
| 2000 | | | | | 2005 | | | | | 2010 | | | | | 2015 | |
| GGA | GAG | TTG | CAG | TTA | CTG | TTG | GAA | GAA | ATA | AAG | AGC | AGC | AAA | GAT | CAA | 6636 |
| Gly | Glu | Leu | Gln | Leu | Leu | Leu | Glu | Glu | Ile | Lys | Ser | Ser | Lys | Asp | Gln | |
| | | | | 2020 | | | | | 2025 | | | | | 2030 | | |
| TTG | AAG | GAG | CTC | ACA | CTA | GAA | AAT | AGT | GAA | TTG | AAG | AAG | AGC | CTA | GAT | 6684 |
| Leu | Lys | Glu | Leu | Thr | Leu | Glu | Asn | Ser | Glu | Leu | Lys | Lys | Ser | Leu | Asp | |
| | | | 2035 | | | | | 2040 | | | | | 2045 | | | |
| TGC | ATG | CAC | AAA | GAC | CAG | GTG | GAA | AAG | GAA | GGG | AAA | GTG | AGA | GAG | GAA | 6732 |
| Cys | Met | His | Lys | Asp | Gln | Val | Glu | Lys | Glu | Gly | Lys | Val | Arg | Glu | Glu | |
| | | | 2050 | | | | | 2055 | | | | | 2060 | | | |
| ATA | GCT | GAA | TAT | CAG | CTA | CGG | CTT | CAT | GAA | GCT | GAA | AAG | AAA | CAC | CAG | 6780 |
| Ile | Ala | Glu | Tyr | Gln | Leu | Arg | Leu | His | Glu | Ala | Glu | Lys | Lys | His | Gln | |
| | | 2065 | | | | | 2070 | | | | | 2075 | | | | |
| GCT | TTG | CTT | TTG | GAC | ACA | AAC | AAA | CAG | TAT | GAA | GTA | GAA | ATC | CAG | ACA | 6828 |
| Ala | Leu | Leu | Leu | Asp | Thr | Asn | Lys | Gln | Tyr | Glu | Val | Glu | Ile | Gln | Thr | |
| 2080 | | | | | 2085 | | | | | 2090 | | | | | 2095 | |
| TAC | CGA | GAG | AAA | TTG | ACT | TCT | AAA | GAA | GAA | TGT | CTC | AGT | TCA | CAG | AAG | 6876 |
| Tyr | Arg | Glu | Lys | Leu | Thr | Ser | Lys | Glu | Glu | Cys | Leu | Ser | Ser | Gln | Lys | |
| | | | | 2100 | | | | | 2105 | | | | | 2110 | | |
| CTG | GAG | ATA | GAC | CTT | TTA | AAG | TCT | AGT | AAA | GAA | GAG | CTC | AAT | AAT | TCA | 6924 |
| Leu | Glu | Ile | Asp | Leu | Leu | Lys | Ser | Ser | Lys | Glu | Glu | Leu | Asn | Asn | Ser | |
| | | | 2115 | | | | | 2120 | | | | | 2125 | | | |
| TTG | AAA | GCT | ACT | ACT | CAG | ATT | TTG | GAA | GAA | TTG | AAG | AAA | ACC | AAG | ATG | 6972 |
| Leu | Lys | Ala | Thr | Thr | Gln | Ile | Leu | Glu | Glu | Leu | Lys | Lys | Thr | Lys | Met | |
| | | 2130 | | | | | 2135 | | | | | 2140 | | | | |

```
GAC AAT CTA AAA TAT GTA AAT CAG TTG AAG AAG GAA AAT GAA CGT GCC        7020
Asp Asn Leu Lys Tyr Val Asn Gln Leu Lys Lys Glu Asn Glu Arg Ala
2145                2150                2155

CAG GGG AAA ATG AAG TTG TTG ATC AAA TCC TGT AAA CAG CTG GAA GAG        7068
Gln Gly Lys Met Lys Leu Leu Ile Lys Ser Cys Lys Gln Leu Glu Glu
2160                2165                2170                2175

GAA AAG GAG ATA CTG CAG AAA GAA CTC TCT CAA CTT CAA GCT GCA CAG        7116
Glu Lys Glu Ile Leu Gln Lys Glu Leu Ser Gln Leu Gln Ala Ala Gln
                2180                2185                2190

GAG AAG CAG AAA ACA GGT ACT GTT ATG GAT ACC AAG GTC GAT GAA TTA        7164
Glu Lys Gln Lys Thr Gly Thr Val Met Asp Thr Lys Val Asp Glu Leu
2195                2200                2205

ACA ACT GAG ATC AAA GAA CTG AAA GAA ACT CTT GAA GAA AAA ACC AAG        7212
Thr Thr Glu Ile Lys Glu Leu Lys Glu Thr Leu Glu Glu Lys Thr Lys
2210                2215                2220

GAG GCA GAT GAA TAC TTG GAT AAG TAC TGT TCC TTG CTT ATA AGC CAT        7260
Glu Ala Asp Glu Tyr Leu Asp Lys Tyr Cys Ser Leu Leu Ile Ser His
2225                2230                2235

GAA AAG TTA GAG AAA GCT AAA GAG ATG TTA GAG ACA CAA GTG GCC CAT        7308
Glu Lys Leu Glu Lys Ala Lys Glu Met Leu Glu Thr Gln Val Ala His
2240                2245                2250                2255

CTG TGT TCA CAG CAA TCT AAA CAA GAT TCC CGA GGG TCT CCT TTG CTA        7356
Leu Cys Ser Gln Gln Ser Lys Gln Asp Ser Arg Gly Ser Pro Leu Leu
                2260                2265                2270

GGT CCA GTT GTT CCA GGA CCA TCT CCA ATC CCT TCT GTT ACT GAA AAG        7404
Gly Pro Val Val Pro Gly Pro Ser Pro Ile Pro Ser Val Thr Glu Lys
2275                2280                2285

AGG TTA TCA TCT GGC CAA AAT AAA GCT TCA GGC AAG AGG CAA AGA TCC        7452
Arg Leu Ser Ser Gly Gln Asn Lys Ala Ser Gly Lys Arg Gln Arg Ser
2290                2295                2300

AGT GGA ATA TGG GAG AAT GGT GGA GGA CCA ACA CCT GCT ACC CCA GAG        7500
Ser Gly Ile Trp Glu Asn Gly Gly Gly Pro Thr Pro Ala Thr Pro Glu
2305                2310                2315

AGC TTT TCT AAA AAA AGC AAG AAA GCA GTC ATG AGT GGT ATT CAC CCT        7548
Ser Phe Ser Lys Lys Ser Lys Lys Ala Val Met Ser Gly Ile His Pro
2320                2325                2330                2335

GCA GAA GAC ACG GAA GGT ACT GAG TTT GAG CCA GAG GGA CTT CCA GAA        7596
Ala Glu Asp Thr Glu Gly Thr Glu Phe Glu Pro Glu Gly Leu Pro Glu
                2340                2345                2350

GTT GTA AAG AAA GGG TTT GCT GAC ATC CCG ACA GGA AAG ACT AGC CCA        7644
Val Val Lys Lys Gly Phe Ala Asp Ile Pro Thr Gly Lys Thr Ser Pro
2355                2360                2365

TAT ATC CTG CGA AGA ACA ACC ATG GCA ACT CGG ACC AGC CCC CGC CTG        7692
Tyr Ile Leu Arg Arg Thr Thr Met Ala Thr Arg Thr Ser Pro Arg Leu
2370                2375                2380

GCT GCA CAG AAG TTA GCG CTA TCC CCA CTG AGT CTC GGC AAA GAA AAT        7740
Ala Ala Gln Lys Leu Ala Leu Ser Pro Leu Ser Leu Gly Lys Glu Asn
2385                2390                2395

CTT GCA GAG TCC TCC AAA CCA ACA GCT GGT GGC AGC AGA TCA CAA AAG        7788
Leu Ala Glu Ser Ser Lys Pro Thr Ala Gly Gly Ser Arg Ser Gln Lys
2400                2405                2410                2415

GTC AAA GTT GCT CAG CGG AGC CCA GTA GAT TCA GGC ACC ATC CTC CGA        7836
Val Lys Val Ala Gln Arg Ser Pro Val Asp Ser Gly Thr Ile Leu Arg
                2420                2425                2430

GAA CCC ACC ACG AAA TCC GTC CCA GTC AAT AAT CTT CCT GAG AGA AGT        7884
Glu Pro Thr Thr Lys Ser Val Pro Val Asn Asn Leu Pro Glu Arg Ser
2435                2440                2445

CCG ACT GAC AGC CCC AGA GAG GGC CTG AGG GTC AAG CGA GGC CGA CTT        7932
Pro Thr Asp Ser Pro Arg Glu Gly Leu Arg Val Lys Arg Gly Arg Leu
2450                2455                2460
```

-continued

| | | | | | | | | | | | | | | | | |
|---|---|---|---|---|---|---|---|---|---|---|---|---|---|---|---|---|
| GTC | CCC | AGC | CCC | AAA | GCT | GGA | CTG | GAG | TCC | AAG | GGC | AGT | GAG | AAC | TGT | 7980 |
| Val | Pro | Ser | Pro | Lys | Ala | Gly | Leu | Glu | Ser | Lys | Gly | Ser | Glu | Asn | Cys | |
| | 2465 | | | | 2470 | | | | | 2475 | | | | | | |

| | | | | | |
|---|---|---|---|---|---|
| AAG | GTC | CAG | T GAAGGCACTT TGTGTGTCAG TACCCCTGGG AGGTGCCAGT | | 8030 |
| Lys | Val | Gln | | | |
| 2480 | | | | | |

| | | | | |
|---|---|---|---|---|
| CATTGAATAG | ATAAGGCTGT | GCCTACAGGA | CTTCTCTTTA | GTCAGGGCAT GCTTTATTAG | 8090 |
| TGAGGAGAAA | ACAATTCCTT | AGAAGTCTTA | AATATATTGT | ACTCTTTAGA TCTCCCATGT | 8150 |
| GTAGGTATTG | AAAAGTTTG | GAAGCACTGA | TCACCTGTTA | GCATTGCCAT TCCTCTACTG | 8210 |
| CAATGTAAAT | AGTATAAAGC | TATGTATATA | AAGCTTTTG | GTAATATGTT ACAATTAAAA | 8270 |
| TGACAAGCAC | TATATCACAA | TCTCTGTTTG | TATGTGGGTT | TTACACTAAA AAAATGCAAA | 8330 |
| ACACATTTTA | TTCTTCTAAT | TAACAGCTCC | TAGGAAAATG | TAGACTTTTG CTTTATGATA | 8390 |
| TTCTATCTGT | AGTATGAGGC | ATGGAATAGT | TTTGTATCGG | GAATTCTCA GAGCTGAGTA | 8450 |
| AAATGAAGGA | AAAGCATGTT | ATGTGTTTTT | AAGGAAAATG | TGCACACATA TACATGTAGG | 8510 |
| AGTGTTTATC | TTTCTCTTAC | AATCTGTTTT | AGACATCTTT | GCTTATGAAA CCTGTACATA | 8570 |
| TGTGTGTGTG | GGTATGTGTT | TATTTCCAGT | GAGGGCTGCA | GGCTTCCTAG AGGTGTGCTA | 8630 |
| TACCATGCGT | CTGTCGTTGT | GCTTTTTTCT | GTTTTAGAC | CAATTTTTA CAGTTCTTTG | 8690 |
| GTAAGCATTG | TCGTATCTGG | TGATGGATTA | ACATATAGCC | TTTGTTTTCT AATAAAATAG | 8750 |
| TCGCCTTCGT | TTTCTGTAAA | AAAAAAAAA | AAAAAAAA | | 8789 |

(2) INFORMATION FOR SEQ ID NO:6:

(i) SEQUENCE CHARACTERISTICS:
        (A) LENGTH: 2482 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Met | Glu | Ser | Glu | Lys | Glu | Asn | Leu | Gln | Ser | Lys | Ile | Asn | His | Leu | Glu |
| 1 | | | | 5 | | | | | 10 | | | | | 15 | |
| Thr | Cys | Leu | Lys | Thr | Gln | Gln | Ile | Lys | Ser | His | Glu | Tyr | Asn | Glu | Arg |
| | | | 20 | | | | | 25 | | | | | 30 | | |
| Val | Arg | Thr | Leu | Glu | Met | Asp | Arg | Glu | Asn | Leu | Ser | Val | Glu | Ile | Arg |
| | | 35 | | | | | 40 | | | | | 45 | | | |
| Asn | Leu | His | Asn | Val | Leu | Asp | Ser | Lys | Ser | Val | Glu | Val | Glu | Thr | Gln |
| | 50 | | | | | 55 | | | | | 60 | | | | |
| Lys | Leu | Ala | Tyr | Met | Glu | Leu | Gln | Gln | Lys | Ala | Glu | Phe | Ser | Asp | Gln |
| 65 | | | | | 70 | | | | | 75 | | | | | 80 |
| Lys | His | Gln | Lys | Glu | Ile | Glu | Asn | Met | Cys | Leu | Lys | Thr | Ser | Gln | Leu |
| | | | | 85 | | | | | 90 | | | | | 95 | |
| Thr | Gly | Gln | Val | Glu | Asp | Leu | Glu | His | Lys | Leu | Gln | Leu | Leu | Ser | Asn |
| | | | 100 | | | | | 105 | | | | | 110 | | |
| Glu | Ile | Met | Asp | Lys | Asp | Arg | Cys | Tyr | Gln | Asp | Leu | His | Ala | Glu | Tyr |
| | | 115 | | | | | 120 | | | | | 125 | | | |
| Glu | Ser | Leu | Arg | Asp | Leu | Leu | Lys | Ser | Lys | Asp | Ala | Ser | Leu | Val | Thr |
| | 130 | | | | | 135 | | | | | 140 | | | | |
| Asn | Glu | Asp | His | Gln | Arg | Ser | Leu | Leu | Ala | Phe | Asp | Gln | Gln | Pro | Ala |
| 145 | | | | | 150 | | | | | 155 | | | | | 160 |
| Met | His | His | Ser | Phe | Ala | Asn | Ile | Ile | Gly | Glu | Gln | Gly | Ser | Met | Pro |
| | | | | 165 | | | | | 170 | | | | | 175 | |
| Ser | Glu | Arg | Ser | Glu | Cys | Arg | Leu | Glu | Ala | Asp | Gln | Ser | Pro | Lys | Asn |

|     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- |
| Ser | Ala | Ile<br>195 | Leu | Gln | Asn | Arg | Val<br>200 | Asp | Ser | Leu | Glu | Phe<br>205 | Ser | Leu | Glu |
| Ser | Gln<br>210 | Lys | Gln | Met | Asn | Ser<br>215 | Asp | Leu | Gln | Lys | Gln<br>220 | Cys | Glu | Glu | Leu |
| Val<br>225 | Gln | Ile | Lys | Gly | Glu<br>230 | Ile | Glu | Glu | Asn | Leu<br>235 | Met | Lys | Ala | Glu | Gln<br>240 |
| Met | His | Gln | Ser | Phe<br>245 | Val | Ala | Glu | Thr | Ser<br>250 | Gln | Arg | Ile | Ser | Lys<br>255 | Leu |
| Gln | Glu | Asp | Thr<br>260 | Ser | Ala | His | Gln | Asn<br>265 | Val | Val | Ala | Glu | Thr<br>270 | Leu | Ser |
| Ala | Leu | Glu<br>275 | Asn | Lys | Glu | Lys | Glu<br>280 | Leu | Gln | Leu | Leu | Asn<br>285 | Asp | Lys | Val |
| Glu | Thr<br>290 | Glu | Gln | Ala | Glu | Ile<br>295 | Gln | Glu | Leu | Lys | Lys<br>300 | Ser | Asn | His | Leu |
| Leu<br>305 | Glu | Asp | Ser | Leu | Lys<br>310 | Glu | Leu | Gln | Leu | Leu<br>315 | Ser | Glu | Thr | Leu | Ser<br>320 |
| Leu | Glu | Lys | Lys | Glu<br>325 | Met | Ser | Ser | Ile | Ile<br>330 | Ser | Leu | Asn | Lys | Arg<br>335 | Glu |
| Ile | Glu | Glu | Leu<br>340 | Thr | Gln | Glu | Asn | Gly<br>345 | Thr | Leu | Lys | Glu | Ile<br>350 | Asn | Ala |
| Ser | Leu | Asn<br>355 | Gln | Glu | Lys | Met | Asn<br>360 | Leu | Ile | Gln | Lys | Ser<br>365 | Glu | Ser | Phe |
| Ala | Asn<br>370 | Tyr | Ile | Asp | Glu | Arg<br>375 | Glu | Lys | Ser | Ile | Ser<br>380 | Glu | Leu | Ser | Asp |
| Gln<br>385 | Tyr | Lys | Gln | Glu | Lys<br>390 | Leu | Ile | Leu | Leu | Arg<br>395 | Cys | Glu | Glu | Thr<br>400 |     |
| Gly | Asn | Ala | Tyr | Glu<br>405 | Asp | Leu | Ser | Gln | Lys<br>410 | Tyr | Lys | Ala | Ala | Gln<br>415 | Glu |
| Lys | Asn | Ser | Lys<br>420 | Leu | Glu | Cys | Leu | Leu<br>425 | Asn | Glu | Cys | Thr | Ser<br>430 | Leu | Cys |
| Glu | Asn | Arg<br>435 | Lys | Asn | Glu | Leu | Glu<br>440 | Gln | Leu | Lys | Glu | Ala<br>445 | Phe | Ala | Lys |
| Glu | His<br>450 | Gln | Glu | Phe | Leu | Thr<br>455 | Lys | Leu | Ala | Phe | Ala<br>460 | Glu | Glu | Arg | Asn |
| Gln | Asn<br>465 | Leu | Met | Leu | Glu<br>470 | Leu | Glu | Thr | Val | Gln<br>475 | Gln | Ala | Leu | Arg | Ser<br>480 |
| Glu | Met | Thr | Asp | Asn<br>485 | Gln | Asn | Asn | Ser | Lys<br>490 | Ser | Glu | Ala | Gly | Gly<br>495 | Leu |
| Lys | Gln | Glu | Ile<br>500 | Met | Thr | Leu | Lys | Glu<br>505 | Glu | Gln | Asn | Lys | Met<br>510 | Gln | Lys |
| Glu | Val | Asn<br>515 | Asp | Leu | Leu | Gln | Glu<br>520 | Asn | Glu | Gln | Leu | Met<br>525 | Lys | Val | Met |
| Lys | Thr<br>530 | Lys | His | Glu | Cys | Gln<br>535 | Asn | Leu | Glu | Ser | Glu<br>540 | Pro | Ile | Arg | Asn |
| Ser<br>545 | Val | Lys | Glu | Arg | Glu<br>550 | Ser | Glu | Arg | Asn | Gln<br>555 | Cys | Asn | Phe | Lys | Pro<br>560 |
| Gln | Met | Asp | Leu | Glu<br>565 | Val | Lys | Glu | Ile | Ser<br>570 | Leu | Asp | Ser | Tyr | Asn<br>575 | Ala |
| Gln | Leu | Val | Gln | Leu<br>580 | Glu | Ala | Met | Leu | Arg<br>585 | Asn | Lys | Glu | Leu<br>590 | Lys | Leu |
| Gln | Glu | Ser<br>595 | Glu | Lys | Glu | Lys | Glu<br>600 | Cys | Leu | Gln | His | Glu<br>605 | Leu | Gln | Thr |

-continued

| | | | | | | | | | | | | | | |
|---|---|---|---|---|---|---|---|---|---|---|---|---|---|---|
| Ile | Arg<br>610 | Gly | Asp | Leu | Glu<br>615 | Thr | Ser | Asn | Leu | Gln<br>620 | Asp | Met | Gln | Ser | Gln |
| Glu<br>625 | Ile | Ser | Gly | Leu | Lys<br>630 | Asp | Cys | Glu | Ile | Asp<br>635 | Ala | Glu | Lys | Tyr<br>640 |
| Ile | Ser | Gly | Pro | His<br>645 | Glu | Leu | Ser | Thr | Ser<br>650 | Gln | Asn | Asp | Asn | Ala<br>655 | His |
| Leu | Gln | Cys | Ser<br>660 | Leu | Gln | Thr | Thr | Met<br>665 | Asn | Lys | Leu | Asn | Glu<br>670 | Leu | Glu |
| Lys | Ile | Cys<br>675 | Glu | Ile | Leu | Gln | Ala<br>680 | Glu | Lys | Tyr | Glu | Leu<br>685 | Val | Thr | Glu |
| Leu | Asn<br>690 | Asp | Ser | Arg | Ser | Glu<br>695 | Cys | Ile | Thr | Ala | Thr<br>700 | Arg | Lys | Met | Ala |
| Glu<br>705 | Glu | Val | Gly | Lys | Leu<br>710 | Leu | Asn | Glu | Val | Lys<br>715 | Ile | Leu | Asn | Asp | Asp<br>720 |
| Ser | Gly | Leu | Leu | His<br>725 | Gly | Glu | Leu | Val | Glu<br>730 | Asp | Ile | Pro | Gly | Gly<br>735 | Glu |
| Phe | Gly | Glu | Gln<br>740 | Pro | Asn | Glu | Gln | His<br>745 | Pro | Val | Ser | Leu | Ala<br>750 | Pro | Leu |
| Asp | Glu | Ser<br>755 | Asn | Ser | Tyr | Glu | His<br>760 | Leu | Thr | Leu | Ser | Asp<br>765 | Lys | Glu | Val |
| Gln | Met<br>770 | His | Phe | Ala | Glu | Leu<br>775 | Gln | Glu | Lys | Phe | Leu<br>780 | Ser | Leu | Gln | Ser |
| Glu<br>785 | His | Lys | Ile | Leu | His<br>790 | Asp | Gln | His | Cys | Gln<br>795 | Met | Ser | Ser | Lys | Met<br>800 |
| Ser | Glu | Leu | Gln | Thr<br>805 | Tyr | Val | Asp | Ser | Leu<br>810 | Lys | Ala | Glu | Asn | Leu<br>815 | Val |
| Leu | Ser | Thr | Asn<br>820 | Leu | Arg | Asn | Phe | Gln<br>825 | Gly | Asp | Leu | Val | Lys<br>830 | Glu | Met |
| Gln | Leu | Gly<br>835 | Leu | Glu | Glu | Gly | Leu<br>840 | Val | Pro | Ser | Leu | Ser<br>845 | Ser | Ser | Cys |
| Val | Pro<br>850 | Asp | Ser | Ser | Ser | Leu<br>855 | Ser | Ser | Leu | Gly | Asp<br>860 | Ser | Ser | Phe | Tyr |
| Arg<br>865 | Ala | Leu | Leu | Glu | Gln<br>870 | Thr | Gly | Asp | Met | Ser<br>875 | Leu | Leu | Ser | Asn | Leu<br>880 |
| Glu | Gly | Ala | Val | Ser<br>885 | Ala | Asn | Gln | Cys | Ser<br>890 | Val | Asp | Glu | Val | Phe<br>895 | Cys |
| Ser | Ser | Leu | Gln<br>900 | Glu | Glu | Asn | Leu | Thr<br>905 | Arg | Lys | Glu | Thr | Pro<br>910 | Ser | Ala |
| Pro | Ala | Lys<br>915 | Gly | Val | Glu | Glu | Leu<br>920 | Glu | Ser | Leu | Cys | Glu<br>925 | Val | Tyr | Arg |
| Gln | Ser<br>930 | Leu | Glu | Lys | Leu<br>935 | Glu | Glu | Lys | Met | Glu<br>940 | Ser | Gln | Gly | Ile | Met |
| Lys<br>945 | Asn | Lys | Glu | Ile | Gln<br>950 | Glu | Leu | Glu | Gln | Leu<br>955 | Leu | Ser | Ser | Glu | Arg<br>960 |
| Gln | Glu | Leu | Asp | Cys<br>965 | Leu | Arg | Lys | Gln | Tyr<br>970 | Leu | Ser | Glu | Asn | Glu<br>975 | Gln |
| Trp | Gln | Gln | Lys<br>980 | Leu | Thr | Ser | Val | Thr<br>985 | Leu | Glu | Met | Glu | Ser<br>990 | Lys | Leu |
| Ala | Ala | Glu<br>995 | Lys | Lys | Gln | Thr<br>1000 | Glu | Gln | Leu | Ser | Leu<br>1005 | Glu | Leu | Glu | Val |
| Ala | Arg | Leu<br>1010 | Gln | Leu | Gln | Gly<br>1015 | Leu | Asp | Leu | Ser | Ser<br>1020 | Arg | Ser | Leu | Leu |
| Gly | Ile<br>1025 | Asp | Thr | Glu | Asp<br>1030 | Ala | Ile | Gln | Gly | Arg<br>1035 | Asn | Glu | Ser | Cys | Asp<br>1040 |

```
Ile  Ser  Lys  Glu  His  Thr  Ser  Glu  Thr  Thr  Glu  Arg  Thr  Pro  Lys  His
              1045                     1050                     1055

Asp  Val  His  Gln  Ile  Cys  Asp  Lys  Asp  Ala  Gln  Gln  Asp  Leu  Asn  Leu
              1060                     1065                     1070

Asp  Ile  Glu  Lys  Ile  Thr  Glu  Thr  Gly  Ala  Leu  Lys  Pro  Thr  Gly  Glu
              1075                     1080                     1085

Cys  Ser  Gly  Glu  Gln  Ser  Pro  Asp  Thr  Asn  Tyr  Glu  Pro  Pro  Gly  Glu
              1090                     1095                     1100

Asp  Lys  Thr  Gln  Gly  Ser  Ser  Glu  Cys  Ile  Ser  Glu  Leu  Ser  Phe  Ser
1105                     1110                     1115                     1120

Gly  Pro  Asn  Ala  Leu  Val  Pro  Met  Asp  Phe  Leu  Gly  Asn  Gln  Glu  Asp
              1125                     1130                     1135

Ile  His  Asn  Leu  Gln  Leu  Arg  Val  Lys  Glu  Thr  Ser  Asn  Glu  Asn  Leu
              1140                     1145                     1150

Arg  Leu  Leu  His  Val  Ile  Glu  Asp  Arg  Asp  Arg  Lys  Val  Glu  Ser  Leu
              1155                     1160                     1165

Leu  Asn  Glu  Met  Lys  Glu  Leu  Asp  Ser  Lys  Leu  His  Leu  Gln  Glu  Val
              1170                     1175                     1180

Gln  Leu  Met  Thr  Lys  Ile  Glu  Ala  Cys  Ile  Glu  Leu  Glu  Lys  Ile  Val
1185                     1190                     1195                     1200

Gly  Glu  Leu  Lys  Lys  Glu  Asn  Ser  Asp  Leu  Ser  Glu  Lys  Leu  Glu  Tyr
              1205                     1210                     1215

Phe  Ser  Cys  Asp  His  Gln  Glu  Leu  Leu  Gln  Arg  Val  Glu  Thr  Ser  Glu
              1220                     1225                     1230

Gly  Leu  Asn  Ser  Asp  Leu  Glu  Met  His  Ala  Asp  Lys  Ser  Ser  Arg  Glu
              1235                     1240                     1245

Asp  Ile  Gly  Asp  Asn  Val  Ala  Lys  Val  Asn  Asp  Ser  Trp  Lys  Glu  Arg
              1250                     1255                     1260

Phe  Leu  Asp  Val  Glu  Asn  Glu  Leu  Ser  Arg  Ile  Arg  Ser  Glu  Lys  Ala
1265                     1270                     1275                     1280

Ser  Ile  Glu  His  Glu  Ala  Leu  Tyr  Leu  Glu  Ala  Asp  Leu  Glu  Val  Val
              1285                     1290                     1295

Gln  Thr  Glu  Lys  Leu  Cys  Leu  Glu  Lys  Asp  Asn  Glu  Asn  Lys  Gln  Lys
              1300                     1305                     1310

Val  Ile  Val  Cys  Leu  Glu  Glu  Glu  Leu  Ser  Val  Val  Thr  Ser  Glu  Arg
              1315                     1320                     1325

Asn  Gln  Leu  Arg  Gly  Glu  Leu  Asp  Thr  Met  Ser  Lys  Lys  Thr  Thr  Ala
              1330                     1335                     1340

Leu  Asp  Gln  Leu  Ser  Glu  Lys  Met  Lys  Glu  Lys  Thr  Gln  Glu  Leu  Glu
1345                     1350                     1355                     1360

Ser  His  Gln  Ser  Glu  Cys  Leu  His  Cys  Ile  Gln  Val  Ala  Glu  Ala  Glu
              1365                     1370                     1375

Val  Lys  Glu  Lys  Thr  Glu  Leu  Leu  Gln  Thr  Leu  Ser  Ser  Asp  Val  Ser
              1380                     1385                     1390

Glu  Leu  Leu  Lys  Asp  Lys  Thr  His  Leu  Gln  Glu  Lys  Leu  Gln  Ser  Leu
              1395                     1400                     1405

Glu  Lys  Asp  Ser  Gln  Ala  Leu  Ser  Leu  Thr  Lys  Cys  Glu  Leu  Glu  Asn
              1410                     1415                     1420

Gln  Ile  Ala  Gln  Leu  Asn  Lys  Glu  Lys  Glu  Leu  Leu  Val  Lys  Glu  Ser
1425                     1430                     1435                     1440

Glu  Ser  Leu  Gln  Ala  Arg  Leu  Ser  Glu  Ser  Asp  Tyr  Glu  Lys  Leu  Asn
              1445                     1450                     1455

Val  Ser  Lys  Ala  Leu  Glu  Ala  Ala  Leu  Val  Glu  Lys  Gly  Glu  Phe  Ala
```

-continued

```
                1460                    1465                    1470
Leu  Arg  Leu  Ser  Ser  Thr  Gln  Glu  Glu  Val  His  Gln  Leu  Arg  Arg  Gly
         1475                    1480                    1485
Ile  Glu  Lys  Leu  Arg  Val  Arg  Ile  Glu  Ala  Asp  Glu  Lys  Lys  Gln  Leu
         1490                    1495                    1500
His  Ile  Ala  Glu  Lys  Leu  Lys  Glu  Arg  Glu  Arg  Glu  Asn  Asp  Ser  Leu
1505                    1510                    1515                    1520
Lys  Asp  Lys  Val  Glu  Asn  Leu  Glu  Arg  Glu  Leu  Gln  Met  Ser  Glu  Glu
         1525                    1530                    1535
Asn  Gln  Glu  Leu  Val  Ile  Leu  Asp  Ala  Glu  Asn  Ser  Lys  Ala  Glu  Val
         1540                    1545                    1550
Glu  Thr  Leu  Lys  Thr  Gln  Ile  Glu  Glu  Met  Ala  Arg  Ser  Leu  Lys  Val
         1555                    1560                    1565
Phe  Glu  Leu  Asp  Leu  Val  Thr  Leu  Arg  Ser  Glu  Lys  Glu  Asn  Leu  Thr
         1570                    1575                    1580
Lys  Gln  Ile  Gln  Glu  Lys  Gln  Gly  Gln  Leu  Ser  Glu  Leu  Asp  Lys  Leu
1585                    1590                    1595                    1600
Leu  Ser  Ser  Phe  Lys  Ser  Leu  Leu  Glu  Glu  Lys  Glu  Gln  Ala  Glu  Ile
         1605                    1610                    1615
Gln  Ile  Lys  Glu  Glu  Ser  Lys  Thr  Ala  Val  Glu  Met  Leu  Gln  Asn  Gln
         1620                    1625                    1630
Leu  Lys  Glu  Leu  Asn  Glu  Ala  Val  Ala  Ala  Leu  Cys  Gly  Asp  Gln  Glu
         1635                    1640                    1645
Ile  Met  Lys  Ala  Thr  Glu  Gln  Ser  Leu  Asp  Pro  Pro  Ile  Glu  Glu  Glu
         1650                    1655                    1660
His  Gln  Leu  Arg  Asn  Ser  Ile  Glu  Lys  Leu  Arg  Ala  Arg  Leu  Glu  Ala
1665                    1670                    1675                    1680
Asp  Glu  Lys  Lys  Gln  Leu  Cys  Val  Leu  Gln  Gln  Leu  Lys  Glu  Ser  Glu
         1685                    1690                    1695
His  His  Ala  Asp  Leu  Leu  Lys  Gly  Arg  Val  Glu  Asn  Leu  Glu  Arg  Glu
         1700                    1705                    1710
Leu  Glu  Ile  Ala  Arg  Thr  Asn  Gln  Glu  His  Ala  Ala  Leu  Glu  Ala  Glu
         1715                    1720                    1725
Asn  Ser  Lys  Gly  Glu  Val  Glu  Thr  Leu  Lys  Ala  Lys  Ile  Glu  Gly  Met
         1730                    1735                    1740
Thr  Gln  Ser  Leu  Arg  Gly  Leu  Glu  Leu  Asp  Val  Val  Thr  Ile  Arg  Ser
1745                    1750                    1755                    1760
Glu  Lys  Glu  Asn  Leu  Thr  Asn  Glu  Leu  Gln  Lys  Glu  Gln  Glu  Arg  Ile
         1765                    1770                    1775
Ser  Glu  Leu  Glu  Ile  Ile  Asn  Ser  Ser  Phe  Glu  Asn  Ile  Leu  Gln  Glu
         1780                    1785                    1790
Lys  Glu  Gln  Glu  Lys  Val  Gln  Met  Lys  Glu  Lys  Ser  Ser  Thr  Ala  Met
         1795                    1800                    1805
Glu  Met  Leu  Gln  Thr  Gln  Leu  Lys  Glu  Leu  Asn  Glu  Arg  Val  Ala  Ala
         1810                    1815                    1820
Leu  His  Asn  Asp  Gln  Glu  Ala  Cys  Lys  Ala  Lys  Glu  Gln  Asn  Leu  Ser
1825                    1830                    1835                    1840
Ser  Gln  Val  Glu  Cys  Leu  Glu  Leu  Glu  Lys  Ala  Gln  Leu  Leu  Gln  Gly
         1845                    1850                    1855
Leu  Asp  Glu  Ala  Lys  Asn  Asn  Tyr  Ile  Val  Leu  Gln  Ser  Ser  Val  Asn
         1860                    1865                    1870
Gly  Leu  Ile  Gln  Glu  Val  Glu  Asp  Gly  Lys  Gln  Lys  Leu  Glu  Lys  Lys
         1875                    1880                    1885
```

-continued

Asp Glu Glu Ile Ser Arg Leu Lys Asn Gln Ile Gln Asp Gln Glu Gln
    1890                1895                1900

Leu Val Ser Lys Leu Ser Gln Val Glu Gly Glu His Gln Leu Trp Lys
1905                1910                1915                1920

Glu Gln Asn Leu Glu Leu Arg Asn Leu Thr Val Glu Leu Glu Gln Lys
            1925                1930                1935

Ile Gln Val Leu Gln Ser Lys Asn Ala Ser Leu Gln Asp Thr Leu Glu
            1940                1945                1950

Val Leu Gln Ser Ser Tyr Lys Asn Leu Glu Asn Glu Leu Glu Leu Thr
            1955                1960                1965

Lys Met Asp Lys Met Ser Phe Val Glu Lys Val Asn Lys Met Thr Ala
    1970                1975                1980

Lys Glu Thr Glu Leu Gln Arg Glu Met His Glu Met Ala Gln Lys Thr
1985                1990                1995                2000

Ala Glu Leu Gln Glu Glu Leu Ser Gly Glu Lys Asn Arg Leu Ala Gly
            2005                2010                2015

Glu Leu Gln Leu Leu Leu Glu Glu Ile Lys Ser Ser Lys Asp Gln Leu
            2020                2025                2030

Lys Glu Leu Thr Leu Glu Asn Ser Glu Leu Lys Lys Ser Leu Asp Cys
            2035                2040                2045

Met His Lys Asp Gln Val Glu Lys Glu Gly Lys Val Arg Glu Glu Ile
    2050                2055                2060

Ala Glu Tyr Gln Leu Arg Leu His Glu Ala Glu Lys Lys His Gln Ala
2065                2070                2075                2080

Leu Leu Leu Asp Thr Asn Lys Gln Tyr Glu Val Glu Ile Gln Thr Tyr
            2085                2090                2095

Arg Glu Lys Leu Thr Ser Lys Glu Glu Cys Leu Ser Ser Gln Lys Leu
            2100                2105                2110

Glu Ile Asp Leu Leu Lys Ser Ser Lys Glu Glu Leu Asn Asn Ser Leu
            2115                2120                2125

Lys Ala Thr Thr Gln Ile Leu Glu Glu Leu Lys Lys Thr Lys Met Asp
    2130                2135                2140

Asn Leu Lys Tyr Val Asn Gln Leu Lys Lys Glu Asn Glu Arg Ala Gln
2145                2150                2155                2160

Gly Lys Met Lys Leu Leu Ile Lys Ser Cys Lys Gln Leu Glu Glu Glu
            2165                2170                2175

Lys Glu Ile Leu Gln Lys Glu Leu Ser Gln Leu Gln Ala Ala Gln Glu
            2180                2185                2190

Lys Gln Lys Thr Gly Thr Val Met Asp Thr Lys Val Asp Glu Leu Thr
            2195                2200                2205

Thr Glu Ile Lys Glu Leu Lys Glu Thr Leu Glu Glu Lys Thr Lys Glu
    2210                2215                2220

Ala Asp Glu Tyr Leu Asp Lys Tyr Cys Ser Leu Leu Ile Ser His Glu
2225                2230                2235                2240

Lys Leu Glu Lys Ala Lys Glu Met Leu Glu Thr Gln Val Ala His Leu
            2245                2250                2255

Cys Ser Gln Gln Ser Lys Gln Asp Ser Arg Gly Ser Pro Leu Leu Gly
            2260                2265                2270

Pro Val Val Pro Gly Pro Ser Pro Ile Pro Ser Val Thr Glu Lys Arg
    2275                2280                2285

Leu Ser Ser Gly Gln Asn Lys Ala Ser Gly Lys Arg Gln Arg Ser Ser
    2290                2295                2300

Gly Ile Trp Glu Asn Gly Gly Gly Pro Thr Pro Ala Thr Pro Glu Ser
2305                2310                2315                2320

```
Phe  Ser  Lys  Lys  Ser  Lys  Lys  Ala  Val  Met  Ser  Gly  Ile  His  Pro  Ala
              2325                    2330                         2335

Glu  Asp  Thr  Glu  Gly  Thr  Glu  Phe  Glu  Pro  Glu  Gly  Leu  Pro  Glu  Val
         2340                    2345                         2350

Val  Lys  Lys  Gly  Phe  Ala  Asp  Ile  Pro  Thr  Gly  Lys  Thr  Ser  Pro  Tyr
         2355                    2360                    2365

Ile  Leu  Arg  Arg  Thr  Thr  Met  Ala  Thr  Arg  Thr  Ser  Pro  Arg  Leu  Ala
     2370                    2375                    2380

Ala  Gln  Lys  Leu  Ala  Leu  Ser  Pro  Leu  Ser  Leu  Gly  Lys  Glu  Asn  Leu
2385                    2390                    2395                         2400

Ala  Glu  Ser  Ser  Lys  Pro  Thr  Ala  Gly  Gly  Ser  Arg  Ser  Gln  Lys  Val
               2405                    2410                         2415

Lys  Val  Ala  Gln  Arg  Ser  Pro  Val  Asp  Ser  Gly  Thr  Ile  Leu  Arg  Glu
               2420                    2425                         2430

Pro  Thr  Thr  Lys  Ser  Val  Pro  Val  Asn  Asn  Leu  Pro  Glu  Arg  Ser  Pro
               2435                    2440                    2445

Thr  Asp  Ser  Pro  Arg  Glu  Gly  Leu  Arg  Val  Lys  Arg  Gly  Arg  Leu  Val
     2450                    2455                    2460

Pro  Ser  Pro  Lys  Ala  Gly  Leu  Glu  Ser  Lys  Gly  Ser  Glu  Asn  Cys  Lys
2465                    2470                    2475                         2480

Val  Gln
```

( 2 ) INFORMATION FOR SEQ ID NO:7:

( i ) SEQUENCE CHARACTERISTICS:
        ( A ) LENGTH: 180 amino acids
        ( B ) TYPE: amino acid
        ( D ) TOPOLOGY: linear ( x i ) SEQUENCE DESCRIPTION: SEQ ID NO:7:

```
Glu  Glu  Val  His  Gln  Leu  Arg  Arg  Gly  Ile  Glu  Lys  Leu  Arg  Val  Arg
1                   5                        10                       15

Ile  Glu  Ala  Asp  Glu  Lys  Lys  Gln  Leu  His  Ile  Ala  Glu  Lys  Leu  Lys
              20                       25                  30

Glu  Arg  Glu  Arg  Glu  Asn  Asp  Ser  Leu  Lys  Asp  Lys  Val  Glu  Asn  Leu
         35                       40                       45

Glu  Arg  Glu  Leu  Gln  Met  Ser  Glu  Glu  Asn  Gln  Glu  Leu  Ile  Val  Leu
         50                       55                  60

Asp  Ala  Glu  Asn  Ser  Lys  Ala  Glu  Val  Glu  Thr  Leu  Lys  Thr  Gln  Ile
65                       70                  75                            80

Glu  Glu  Met  Ala  Arg  Ser  Leu  Lys  Val  Phe  Glu  Leu  Asp  Leu  Val  Thr
              85                       90                       95

Leu  Arg  Ser  Glu  Lys  Glu  Asn  Leu  Thr  Lys  Gln  Ile  Gln  Glu  Lys  Gln
              100                      105                      110

Gly  Gln  Leu  Ser  Glu  Leu  Asp  Lys  Leu  Leu  Ser  Ser  Phe  Lys  Ser  Leu
         115                      120                      125

Leu  Glu  Glu  Lys  Glu  Gln  Ala  Glu  Ile  Gln  Ile  Lys  Glu  Glu  Ser  Lys
         130                      135                      140

Thr  Ala  Val  Glu  Met  Leu  Gln  Asn  Gln  Leu  Lys  Glu  Leu  Asn  Glu  Ala
145                      150                      155                       160

Val  Ala  Ala  Leu  Cys  Gly  Asp  Gln  Glu  Ile  Met  Lys  Ala  Thr  Glu  Gln
                    165                      170                      175

Ser  Leu  Asp  Pro
              180
```

( 2 ) INFORMATION FOR SEQ ID NO:8:

( i ) SEQUENCE CHARACTERISTICS:
    ( A ) LENGTH: 180 amino acids
    ( B ) TYPE: amino acid
    ( D ) TOPOLOGY: linear ( x i ) SEQUENCE DESCRIPTION: SEQ ID NO:8:

| Pro | Ile | Glu | Glu | Glu | His | Gln | Leu | Arg | Asn | Ser | Ile | Glu | Lys | Leu | Arg |
|---|---|---|---|---|---|---|---|---|---|---|---|---|---|---|---|
| 1 | | | | 5 | | | | | 10 | | | | | 15 | |
| Ala | Arg | Leu | Glu | Ala | Asp | Glu | Lys | Lys | Gln | Leu | Cys | Val | Leu | Gln | Gln |
| | | | 20 | | | | 25 | | | | | | 30 | | |
| Leu | Lys | Glu | Ser | Glu | His | His | Ala | Asp | Leu | Leu | Lys | Gly | Arg | Val | Glu |
| | | 35 | | | | | 40 | | | | | 45 | | | |
| Asn | Leu | Glu | Arg | Glu | Leu | Glu | Ile | Ala | Arg | Thr | Asn | Gln | Glu | His | Ala |
| | 50 | | | | | 55 | | | | | 60 | | | | |
| Ala | Leu | Glu | Ala | Glu | Asn | Ser | Lys | Gly | Glu | Val | Glu | Thr | Leu | Lys | Ala |
| 65 | | | | | 70 | | | | | 75 | | | | | 80 |
| Lys | Ile | Glu | Gly | Met | Thr | Gln | Ser | Leu | Arg | Gly | Leu | Glu | Leu | Asp | Val |
| | | | | 85 | | | | | 90 | | | | | 95 | |
| Val | Thr | Ile | Arg | Ser | Glu | Lys | Glu | Asn | Leu | Thr | Asn | Glu | Leu | Gln | Lys |
| | | | 100 | | | | | 105 | | | | | 110 | | |
| Glu | Gln | Glu | Arg | Ile | Ser | Glu | Leu | Glu | Ile | Ile | Asn | Ser | Ser | Phe | Glu |
| | | 115 | | | | | 120 | | | | | 125 | | | |
| Asn | Ile | Leu | Gln | Glu | Lys | Glu | Gln | Glu | Lys | Val | Gln | Met | Lys | Glu | Lys |
| | 130 | | | | | 135 | | | | | 140 | | | | |
| Ser | Ser | Thr | Ala | Met | Glu | Met | Leu | Gln | Thr | Gln | Leu | Lys | Glu | Leu | Asn |
| 145 | | | | | 150 | | | | | 155 | | | | | 160 |
| Glu | Arg | Val | Ala | Ala | Leu | His | Asn | Asp | Gln | Glu | Ala | Cys | Lys | Ala | Lys |
| | | | | 165 | | | | | 170 | | | | | 175 | |
| Glu | Gln | Asn | Leu | | | | | | | | | | | | |
| | | | 180 | | | | | | | | | | | | |

NUCLEAR MITOTIC PHOSPHOPROTEIN

This application is a continuation-in-part of U.S. Ser. No. 08/141,239, filed Oct. 22, 1993, now abandoned, the contents of which are hereby incorporated by reference into the present disclosure.

This invention made in part with government support under a grant from the National Institute of Health (EYO5758). Accordingly, the United States Government has certain rights to this invention.

BACKGROUND OF THE INVENTION

Throughout this application, various publications are referred to within parentheses. The disclosures of these references are hereby incorporated by reference into the specification.

The events that occur from one cell division to the next are deemed the cell cycle. The cell cycle is comprised of the mitotic phase (M-phase), cytokinesis (cell separation), $G_1$ or gap phase, the synthesis or S-phase and finally $G_2$.

The control of cell division is one of the most basic aspects of multicellular existence. Uncontrolled cell growth and division, which produces cells that divide when they should not, produces contiguous cellular masses called tumors that are the basis for many cancers.

Thus, information concerning the mechanisms to control or promote cell division and proliferation is important to understand and conquer many diseases including cancer. This invention provides this information and provides related advantages as well.

SUMMARY OF THE INVENTION

A novel purified protein designated mitosin is provided by this invention. Also provided are biologically active fragments of mitosin. Methods of using the mitosin protein and fragment, e.g., for the generation of monoclonal antibodies, also is provided.

A nucleic acid molecule encoding mitosin also is provided by this invention, as well as active fragments thereof. The nucleic acid molecules are useful to recombinantly produce mitosin and for use as probes.

The compositions and methods of this invention are based on the instant discovery that the intracellular presence of Mitosin is necessary for a eukaryotic cell to enter into to the M phase of mitosis, and that the degradation of Mitosin is necessary for the cell to advance to the next stage. Thus, an anti-mitosin antibody, a mutant or a non-functional analog of mitosin would inhibit the mitotic cell cycle by preventing cells from entering the M phase, and overexpression of mitosin, or a functional equivalent thereof, would inhibit the cycle by preventing cells from leaving the M phase. Such overexpression could be achieved either addition of the protein or through gene therapy, i.e. delivery of a gene encoding the protein or a functional equivalent thereof.

(A) RNA blotting analysis using mitosin, RB, E2F-1 and Gβ-like cDNA as probes. Monkey kidney CV1 cells were synchronized as described in the Experimental Procedures. 10 μg of total RNA extracted from each sample was subjected to Northern blotting with radioactively labeled cDNAs as indicated. The level of Gβ-like RNA varies very little during the cell-cycle, and thus served as an internal control. Lane 1 is RNA from cells arrested in early G1 by lovastatin (marked as 'G0/G1'). Lane 2 is cells in late G1 after removing lovastatin for 8 hours. Lane 3 is cells arrested at the G1/S boundary by hydroxyurea. Lane 4 is cells in the S phase, after removing the hydroxyurea and nocodazole double block. Lane 5 is mitotic cells collected after the hydroxyurea and nocodazole double block. Lane 6 is G0 cells after 4 days of serum starvation (0.5% fetal calf serum). (B) Quantitation of relative mRNA levels of each gene by densitometry. Each individual mRNA band was normalized to the amount of Gβ-like mRNA to show the expression pattern during the cell-cycle.

FIG. 2: Mitosin Migrates as a 350 Kd Cellular Protein.

$1\times10^6$ actively growing HeLa cells were immunoprecipitated with each antibody to mitosin (α10Bgl, α10Stu, or α10C). After 3–12% gradient SDS-PAGE, the immunoprecipitates were immunoblotted with the same antibody in the absence (−) or presence (+) of the corresponding antigen competitor or maltose binding protein (MBP) (10 μg/ml) to demonstrate the specificity. Antigens used for production of antibodies and also as competitors are shown in the figure. A sample prepared from rabbit backbone muscles was also loaded side by side. The position of nebulin in this muscle sample, serving as a 770 Kd marker, was visualized by immunoblotting with mAb to nebulin (Kruger et al., *J. Cell Biol.* 115:97–107 (1991)).

Figure 3A:
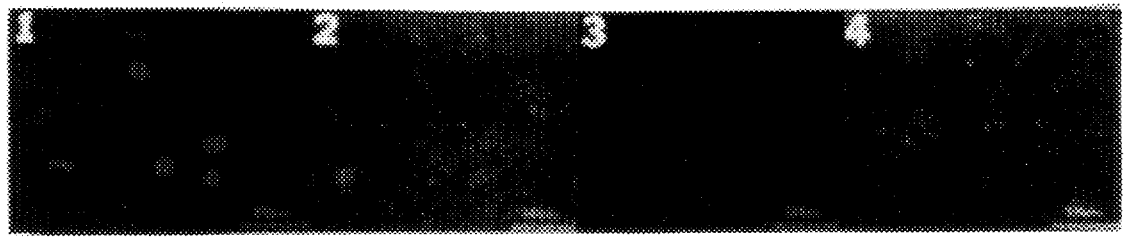
Figure 3B:
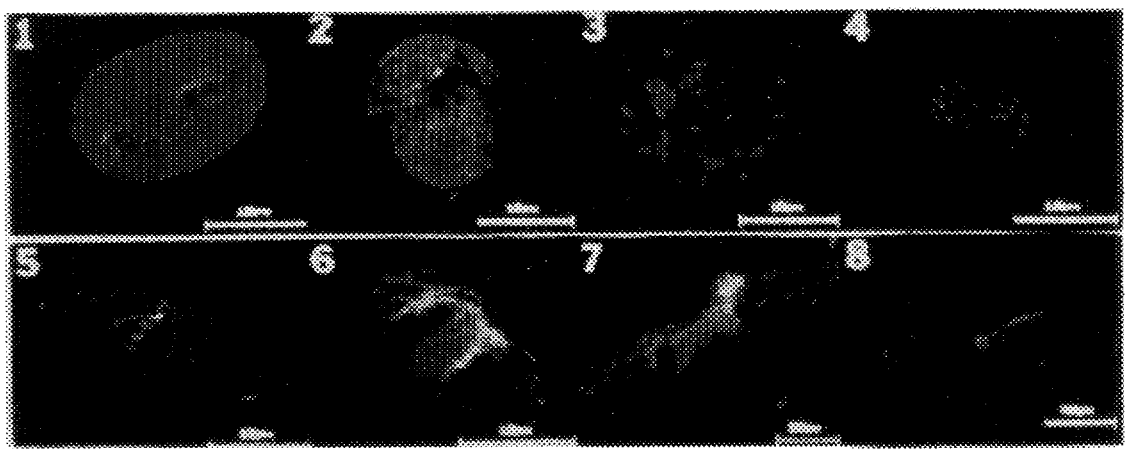
Figure 3C:
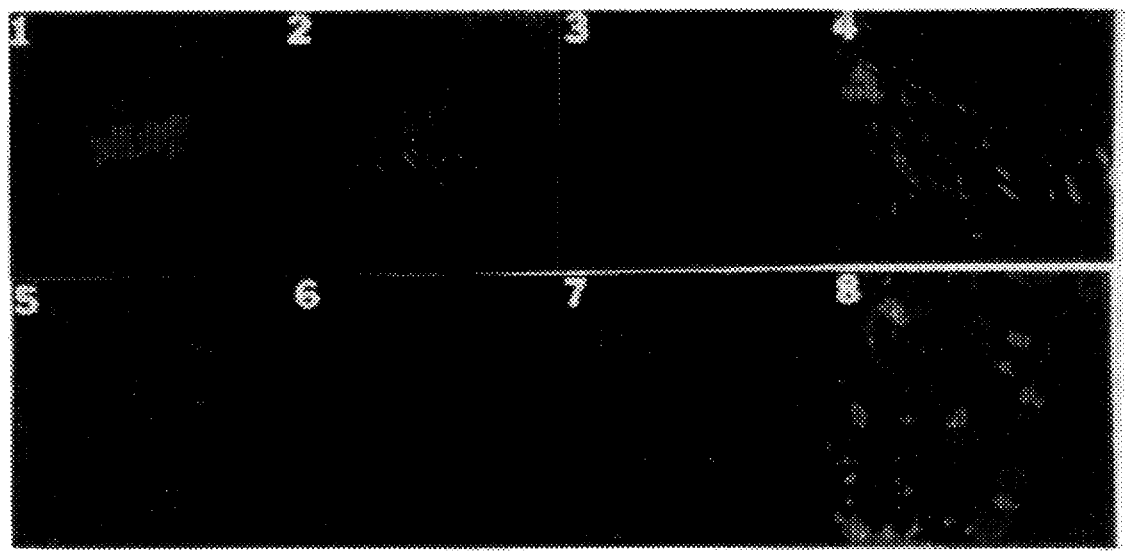
Figures 7A, 7B:
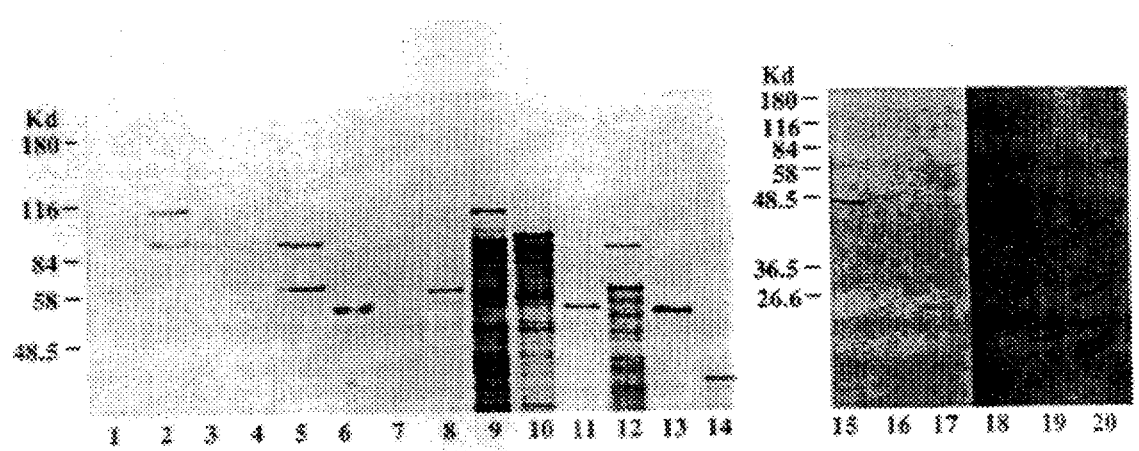

FIGS. 3A–3C: Mitosin Redistributes from the Nucleus to the Centromere, Spindle, and Midbody during M phase Progression.

Monkey kidney CV1 cells were grown directly on glass coverslips. After methanol fixation and labeling with α10C and FITC-conjugated anti-rabbit IgG antibody, indirect immunofluorescence microscopy was performed with a laser-scanning confocal microscope. Digitized optical sections (red) and Normarski differential interference contrast (DIC) images (green) were superimposed or recorded separately. (A1–A4) demonstrates that immunostaining of mitosin was not affected by MBP (10 μg/ml) (A1), but was abolished by the same amount of antigen MBP-10 (A3). (A2) and (A4) represent the corresponding DIC images. (B1–B8) A representative cell from different stages of the cell-cycle: (B1) S or G2 phase; (B2) late G2/early prophase; (B3) prophase; (B4) metaphase; (B5, B6) anaphase; (B7, B8) telophase; (C1–C8) depicts the centromeric staining of mitosin. The centromeric staining was not affected by MBP (10 μg/ml) (C1), but was abolished by MBP-10 (C3). (C2) and (C4) are the corresponding DIC images. Immunostaining of mitosin (C5) with mitotic cells spun onto cover slips was superimposed with the corresponding chromosome staining by propidium iodine (C6) and DIC image (C7) to confirm its centromeric localization (C8). The non-centromeric background in (C5) and (C8) was due to the cytoplasmic portion of mitosin.

FIGS. 4A–4D: Expression and Modification of Mitosin during the Cell Cycle.

Cell lysates prepared from synchronized CV1 as described in Experimental Procedures were analyzed by Western blotting. The appropriate portions of a blot (according to the MW of proteins to be probed) were separately probed with anti-mitosin α10C (A), anti-Rb mAb 11D7 (B), or anti-Gβ-like protein antibody (C). The phosphorylation status of Rb serves as an internal control for the quality of synchronization. Gβ-like protein expressed constantly during the cell cycle was used as an internal control for quantitation of cell lysates. (D) Cell-cycle distribution of the corresponding samples analyzed by flow cytometry to show the status of cell cycle progression.

FIGS. 5A–5C: Modification of Mitosin by Phosphorylation.

(A–B) The results from immunoblotting and autoradiography of the same blot, respectively. Lanes 1 and 4 are mitosin prepared from cells arrested at G1/S by hydroxyurea. Lane 2 is mitosin immunoprecipitated from cells in late S phase, labeled with (32P)-orthophosphate. Lane 3 is the same sample that was treated with calf intestinal alkaline phosphatase (CIAP). (C) The slowest migrating form of mitosin (lane 5) can be converted to the fastest migrating form by CIAP treatment (lane 6).

The results shown in FIGS. 5A through 5C show that regulation of mitosin phosphorylation is critical to its function, as is the case for p110$^{RB}$ (Ludlow et al., *Cell* 56:57–65 (1989)). These results also suggest that mutants of mitosin that cannot be phosphorylated are useful as cell growth inhibitors; and that reagents which block phosphorylation of mitosin would have similar activity. Either protein or gene therapy can be used to utilize these agents to inhibit cell growth. Because of the importance of mitosin in chromosome segregation, inhibitors of mitosin are useful to block gametogenesis.

FIGS. 6A and 6B: Mitosin Interacts with Rb in M Phase.

$3 \times 10^6$ CV1 cells synchronized at prometaphase by nocodazole was lysed and coimmunoprecipitated with either α10Bgl (lane 1), anti-RbmAb 11D7 (lanes 3 and 5), or a control antibody anti-GST (lanes 2 and 4). The immunoprecipitates were analyzed by immunoblotting with α10Bgl.(A) and anti-Rb mAb 11D7 (B). Immunoprecipitates in lanes 2 and 3 were washed three times, while those in lane 4 and 5 were washed five times.

FIGS. 7A–7D: Determination of the Rb-binding Region of Mitosin.

(A) Two identical blots containing seven purified MBP fusion proteins were probed with either the "Rb-sandwich" (lanes 1–7) or with an antibody to MBP (New England Biolabs) (lanes 8–14). Only those fusion proteins sharing the extreme C-terminal region of 211 amino acid residues of mitosin bound to the "Rb sandwich". The faint band in lane 3 (MBP-10/H) is an artifact because it reproducibly migrates faster than the full-length product (lane 10) does. Lanes 1 and 8 were MBP-T antigen served as positive control, lanes 2 and 9 were MBP-10, lanes 3 and 10 were MBP-10/H, lanes 4 and 11 were MBP-10/NB, lanes 5 and 12 were MBP-10/KN, lanes 6 and 13 were MBP-10/NI, and lanes 7 and 14 were MBP alone. (B) Similarly, two identical blots of the purified GST-fusion proteins were probed with either the "Rb-sandwich" (lanes 15–17) or with an antibody to GST (lanes 18–20). Lanes 15 and 18 were GST-T antigen, lanes 16 and 19 were GST alone and lanes 17 and 20 were GST-1045 which bound to the Rb-sandwich. (C) A diagram of the different constructs used in this experiment. The Rb-binding ability for each fusion protein is also included. (D) Sequence comparison of the Rb-binding region of mitosin with the Rb-binding domain of E2F-1 (in bold letters) and neighboring residues (SEQ. ID NOS: 3 and 4). A 51% homology between these two sequences was found. Dashed lines indicate conserved residues and solid lines indicate identical residues.

Figures 8A, 8C:
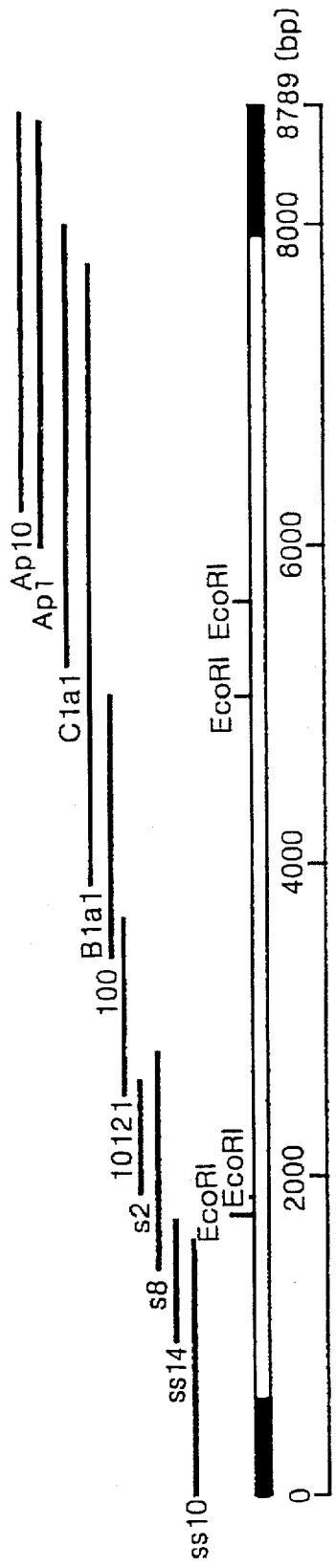
Figure 8B-1:
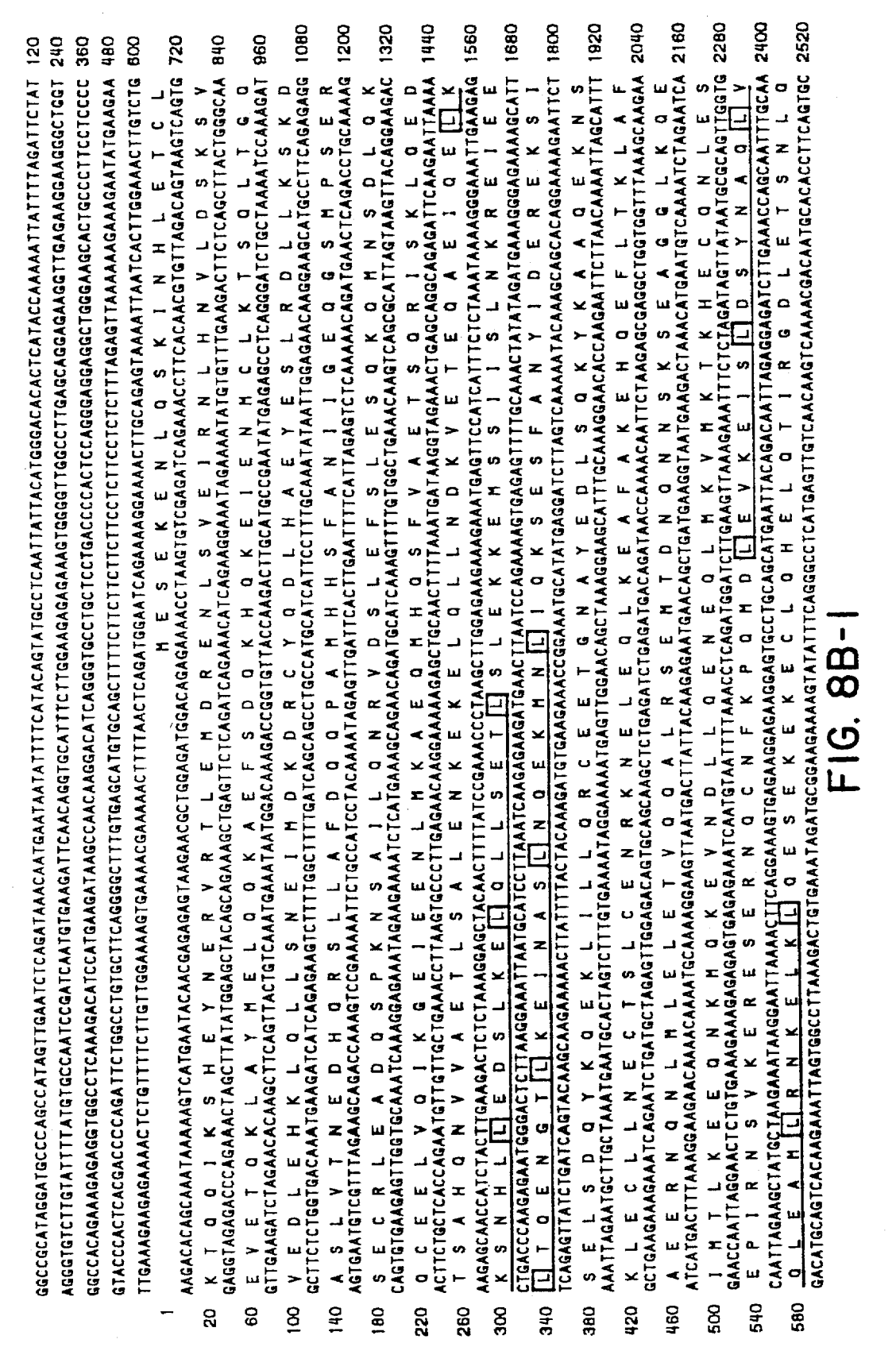
Figure 8B-2:
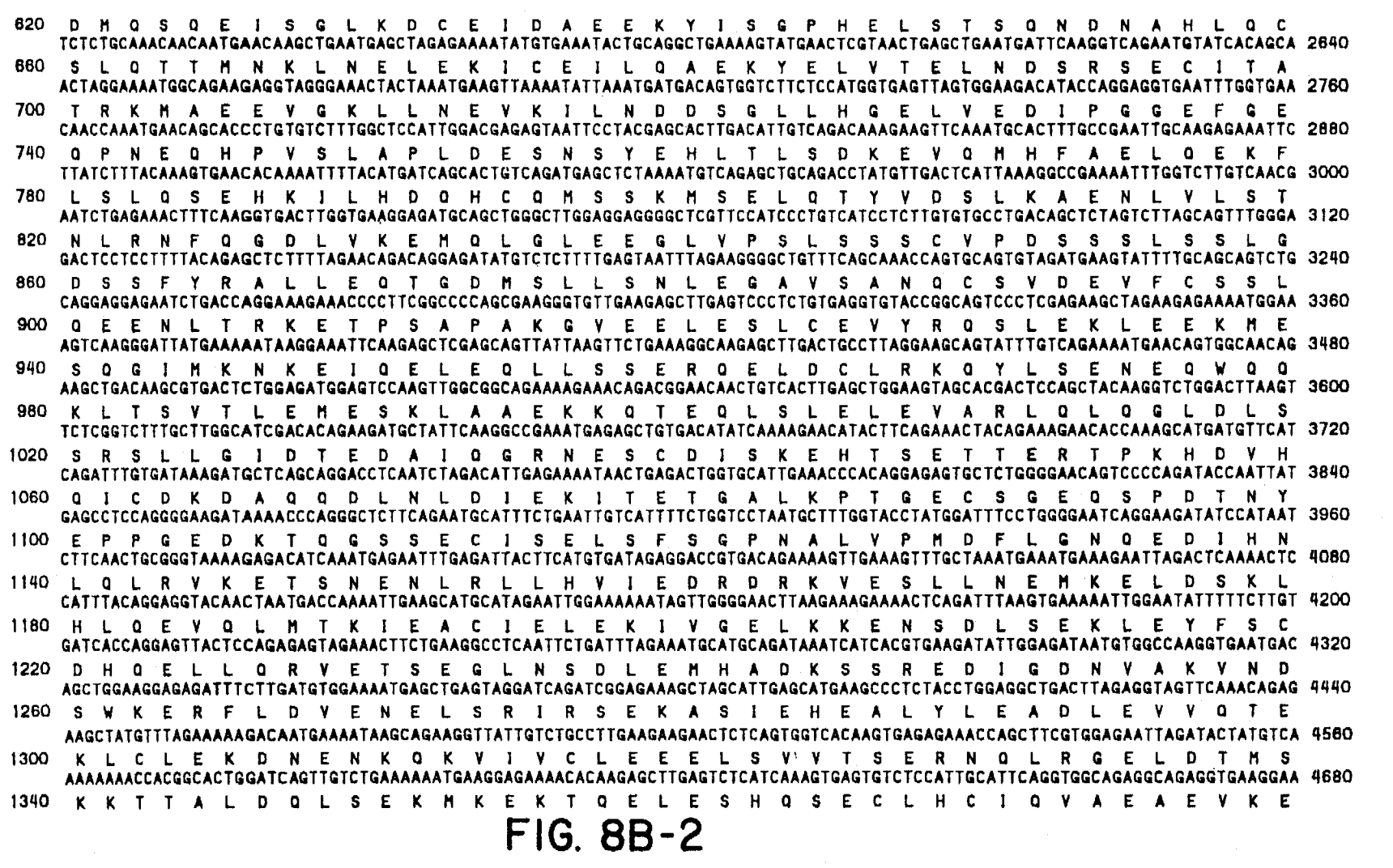
Figure 8B-3:
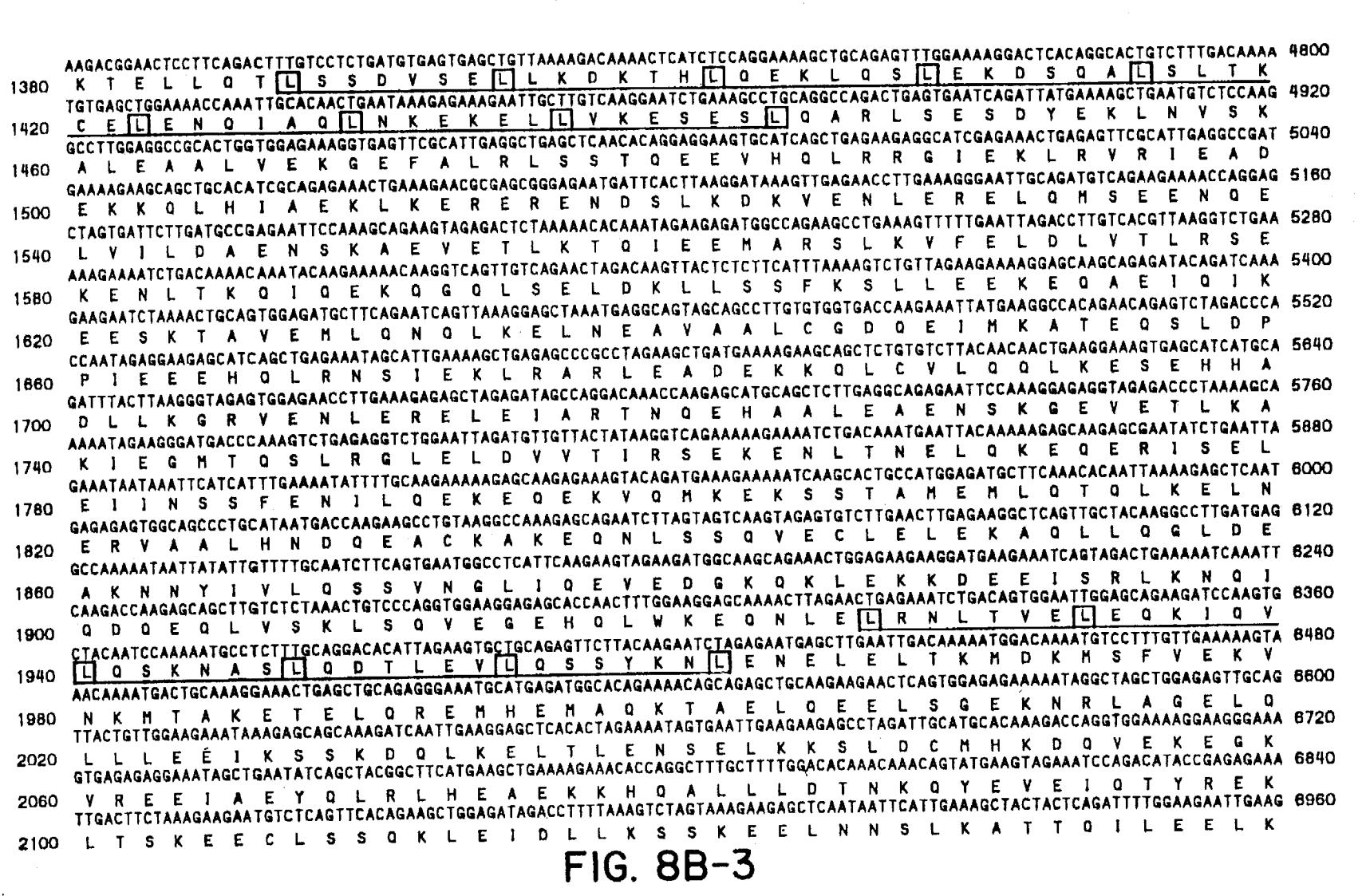
Figure 8B-4:
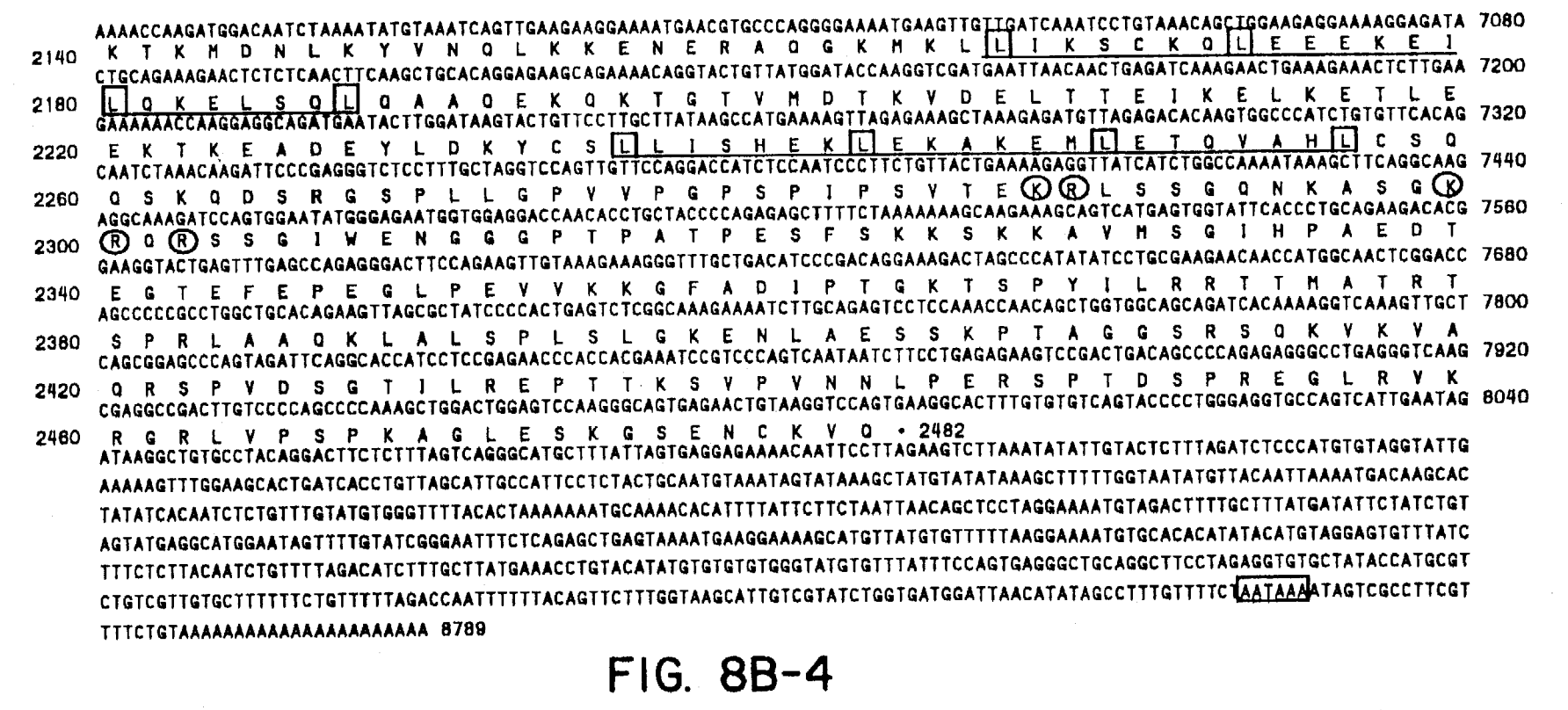

FIGS. 8A–8C: Cloning and Sequence Analysis of Mitosin.

(A) A schematic diagram for overlapping cDNA clones and the full-length cDNA. Solid bars represent untranslated regions. Clones AP10 and AP1 were isolated by the "Rb-sandwich" method. Clone C1a1, B1a1 and 100 were isolated from a Y79 cDNA library. The rest were from a K562 cDNA library. (B) Nucleotide and deduced amino acid sequence of mitosin (SEQ. ID NOS:5 and 6). The putative leucine heptad repeats are underlined; conserved leucines are boxed. The basic residues, presumably representing a bipartite nuclear targeting motif, are circled. The polyadenylation signal at the end of the cDNA is boxed. (C) Alignment for the internal repeats. Identical residues are connected by bars, similar ones by dots (SEQ. ID NOS: 7 and 8).

Figure 9:
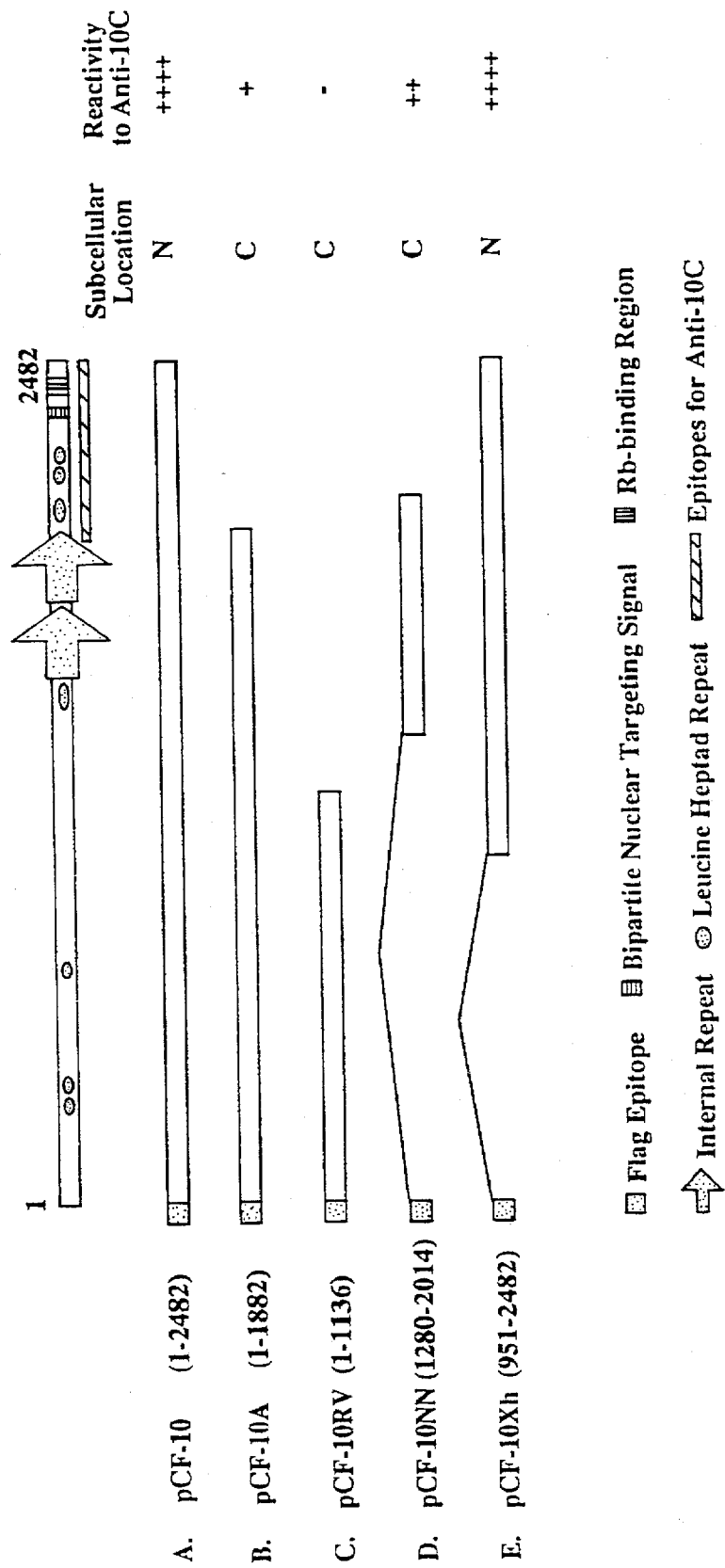

FIG. 9: Schematic Diagram of Mitosin Expression Constructs.

The episomal vector pCEP4 (Invitrogen) was used for initial construction. Each construct is assigned with a letter (A–E) for easier description in text. Both the predicted subcellular location (N-Nuclear; C-Cytoplasmic) and the predicted reactivity of expressed proteins to α10C antibody are listed.

Figure 10:
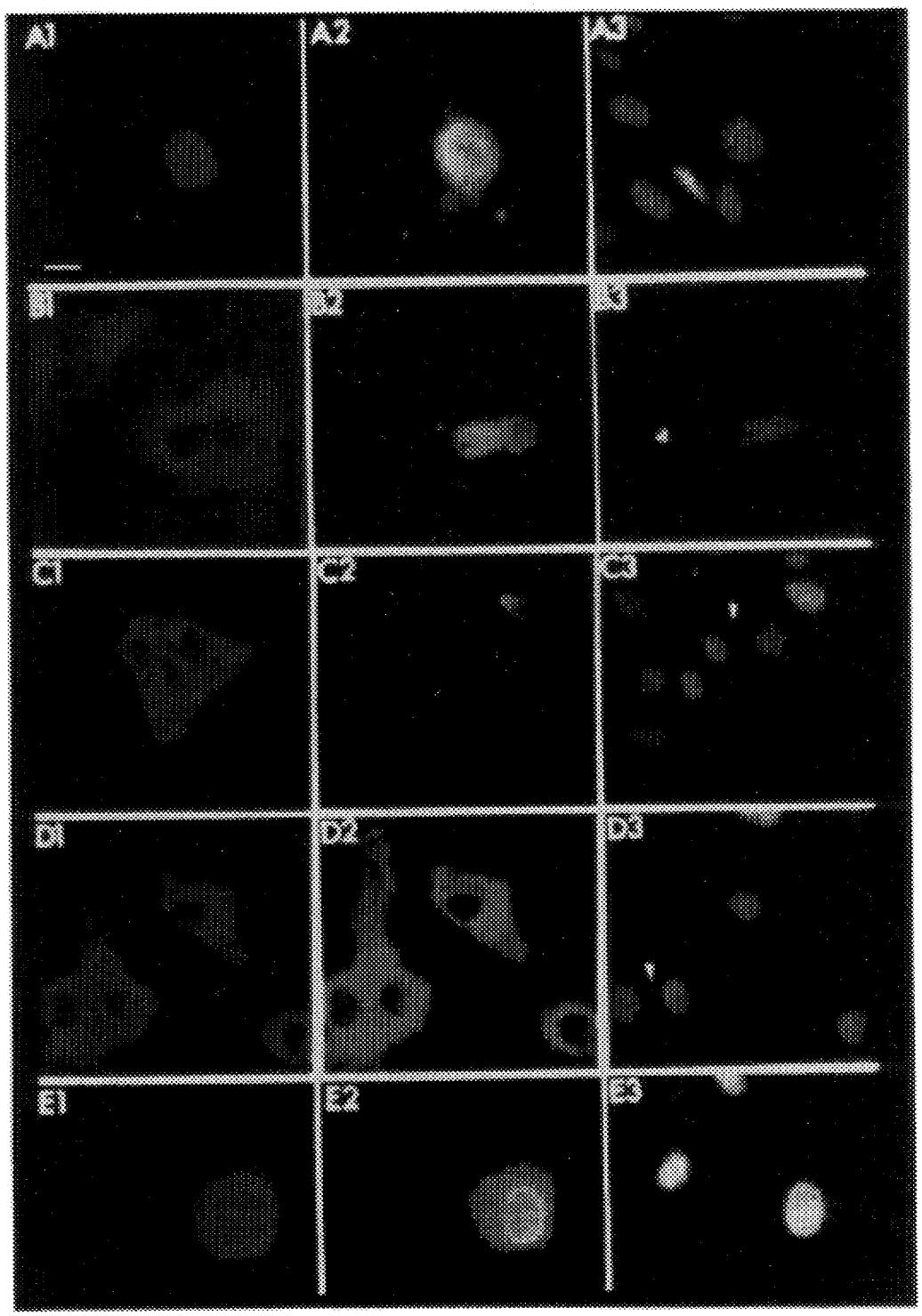

FIG. 10: Transient Expression of Mitosin in CV1 Cells.

Cells growing in 100 mm Petri dishes were methanol-fixed three days after transfection, and subjected to triple fluorescence staining. The flag epitope was stained red (by Texas red; panel A1–E1), the extreme C-terminus of mitosin stained green (by FITC; panel A2–E2), and nuclear DNA stained blue (by DAPI; panel A3–E3). Panels (A)–(E) are representative results from cells expressing the constructs "A"–"E" sequentially. The abnormally divided cells with chromatin bridges in panel (B3), (C3) and (D3) are indicated by arrows. Scale bar: 20 µm.

DETAILED DESCRIPTION OF THE INVENTION

This invention provides a novel, purified mammalian protein designated mitosin. Mitosin has a molecular weight of about 350 kD as determined by Western blot analysis. Mitosin is a cellular protein which has been found to interact with the retinoblastoma protein. It also is cell cycle dependent, that is, it is first synthesized at the G1/S boundary, phosphorylated from S through M phase, and during mitosis, is intimately associated with centromeres/kinetochores and the spindle poles. Mitosin has many of the properties previously described which characterize transcriptional regulatory proteins (Buchkovich et al., *Cell* 58:1097–1105 (1989); Chen et al., *Cell* 58:1193–1198 (1989); deCaprio et al., *Cell* 58:1085–1095 (1989); Ludlow et al., *Cell* 60:387–396 (1990); and Mihara et al., *Science* 246:1300–1303 (1989)).

The compositions and methods of this invention are based on the instant discovery that the intracellular presence of Mitosin is necessary for a eukaryotic cell to enter into to the M phase of mitosis, and that the degradation of Mitosin is necessary for the cell to advance to the next stage. Thus, an anti-mitosin antibody, a mutant or a non-functional analog of mitosin would inhibit the mitotic cell cycle by preventing cells from entering the M phase, and overexpression of mitosin, or a functional equivalent thereof, would inhibit the cycle by preventing cells from leaving the M phase. Such overexpression could be achieved either addition of the protein or through gene therapy, i.e. delivery of a gene encoding the protein or a functional equivalent thereof.

This protein has been purified from both simian and human sources. "Purified", when used to describe the state of mitosin, denotes the protein free of a portion of the other proteins and molecules normally associated with or occurring with mitosin in its native environment. As used herein the term "native" refers to the form of a protein, polypeptide, antibody or a fragment thereof that is isolated from nature or that which is without an intentional amino acid substitution.

Generally, antagonists of mitosin function would be expected to block cell growth; and the presence of mitosin in a cell is an index of proliferation—an important indicator of hyperproliferative diseases, such as cancer.

Thus, antagonists of the novel protein is useful to control pathologic hyperproliferative cells. As used herein, the term "hyperproliferative cells" includes but is not limited to cells having the capacity for autonomous growth, i.e., existing and reproducing independently of normal regulatory mechanisms. Hyperproliferative diseases may be categorized as pathologic, i.e., deviating from normal cells, characterizing or constituting disease, or may be categorized as non-pathologic, i.e., deviation from normal but not associated with a disease state. Pathologic hyperproliferative cells are characteristic of the following disease states, thyroid hyperplasia—Grave's Disease, psoriasis, benign prostatic hypertrophy, Li-Fraumeni syndrome including breast cancer, sarcomas and other neoplasms, bladder cancer, colon cancer, lung cancer, various leukemias and lymphomas. Examples of non-pathologic hyperproliferative cells are found, for instance, in mammary ductal epithelial cells during development of lactation and also in cells associated with wound repair. Pathologic hyperproliferative cells characteristically exhibit loss of contact inhibition and a decline in their ability to selectively adhere which implies a change in the surface properties of the cell and a further breakdown in intercellular communication. These changes include stimulation to divide and the ability to secrete proteolytic enzymes. Moreover, reintroduction or supplementation of lost mitosin function by introduction of the protein or nucleic acid encoding the protein into a cell can restore defective chromosome segregation, which is a marker of progressing malignancy. Malignant proliferation of cells can then be halted.

As is known to those of skill in the art, the term "protein" means a linear polymer of amino acids joined in a specific sequence by peptide bonds. As used herein, the term "amino acid" refers to either the D or L stereoisomer form of the amino acid, unless otherwise specifically designated. Also encompassed within the scope of this invention are equivalent mitosin proteins or equivalent mitosin peptides, having the biological activity of purified mitosin. "Equivalent proteins" and "equivalent polypeptides" refer to compounds that depart from the linear sequence of the naturally occurring proteins or polypeptides, but which have amino acid substitutions that do not change its biological activity. "Biological activity" shall mean having the ability to bind to the retinoblastoma protein under native conditions. These equivalents can differ from the native sequences by the replacement of one or more amino acids with related amino acids, for example, similarly charged amino acids, or the substitution or modification of side chains or functional groups.

It is further understood that limited modifications may be made to the primary sequence of mitosin without destroying its biological function, and that only a portion of the entire primary structure may be required in order to effect activity, one aspect of which is the ability to bind $p110^{RB}$. One such biologically active fragment is a molecule having substantially the C-terminal region of about 600 amino acid residues of the molecule, the sequence of which is shown in FIG. 8. Another biologically active fragment is a molecule having substantially the C-terminal region of about 200 amino acid residues of the molecule, the sequence of which is shown in FIG. 8. As is understood by those of skill in the art, any fragment having at least the C-terminal 200 amino acids up to about the C-terminal 600 amino acids are biologically active fragments of mitosin. Minor modifications of this sequence which do not destroy the activity of the protein also fall within the definition of mitosin and within the definition of the protein claimed as such. Moreover, fragments of the amino acid sequence shown in FIG. 8, but not including the previously described 600 to 200 amino acid fragments, which retain the function of the entire protein are included within the definition. These fragments can be generated by restriction enzyme digestion of the nucleic acid molecule of FIG. 8 and recombinant expression of the resulting fragments. It is understood that minor modifications of primary amino acid sequence can result in proteins which have substantially equivalent or enhanced function as compared to the sequence set forth in FIG. 8. These modifications may be deliberate, as through site-directed mutagenesis, or may be accidental such as through mutation in hosts which are mitosin producers. All of these modifications are included as long as mitosin biological function is retained.

"Inhibitively active" also shall mean fragments and mutants of the mitosin protein ("muteins") that act in a dominant negative fashion thereby inhibiting normal function of the protein, thereby inhibiting the ability of mitosin to mediate host cell division and/or host cell proliferation. These can be, but are not limited to, non-phosphorylated proteins or proteins phosphorylated such that cell proliferation of the host cell is inhibited. These proteins and fragments can be made by expressing the nucleic acid of the mitosin protein in a bacterial host cell that lacks the ability to phosphorylate or by chemical means well known to those of skill in the art. The muteins and inhibitively active fragments are useful therapeutically to inhibit hyperproliferation of cells and to generate diagnostic reagents such as anti-mitosin antibodies.

This invention also provides agents that inhibit phosphorylation of mitosin in a cell. These agents include, but are not limited to calf intestine alkaline phosphatase and other regulatory phosphatases. These agents are useful to inhibit the growth or proliferation of a cell by contacting the cell, in vitro or in vivo with the agent by methods described below. Accordingly, this invention also provides a method to inhibit the growth or proliferation of a cell, such as a hyperproliferative cell, by contacting the cell with the agent. Also provided are methods of treating pathologies characterized by hyperproliferative cell growth, such as cancer, by administering to a suitable subject these agents in an effective concentration such that cell proliferation is inhibited. A suitable subject for this method includes but is not limited to vertebrates, simians, murines, and human patients.

These agents also are useful to block gametogenesis of an immature gamete by contacting the cell, in vitro or in vivo with the agent by methods described below.

Pharmaceutical compositions comprising any of the compositions of matter described above and one or more pharmaceutically acceptable carriers. Pharmaceutically acceptable carriers are well known in the art and include aqueous solutions such as physiologically buffered saline or other solvents or vehicles such as glycols, glycerol, vegetable oils (e.g., olive oil) or injectable organic esters. A pharmaceutically acceptable carrier can be used to administer the mitosin or its equivalent proteins, fragments or mutants thereof to a cell in vitro or to a subject in vivo.

A pharmaceutically acceptable carrier can contain a physiologically acceptable compound that acts, for example, to stabilize the polypeptide or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide and on the particular physiochemical characteristics of the specific polypeptide. For example, a physiologically acceptable compound such as aluminum monosterate or gelatin is particularly useful as a delaying agent, which prolongs the rate of absorption of a pharmaceutical composition administered to a subject. Further examples of carriers, stabilizers or adjutants can be found in Martin, *Remington's Pharm. Sci.*, 15th Ed. (Mack Publ. Co., Easton, 1975), incorporated herein by reference. The pharmaceutical composition also can be incorporated, if desired, into liposomes, microspheres or other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

Purified mitosin or mitosin pharmaceutical compositions are useful to control the growth of a cell by contacting the cell with the purified mitosin, active fragment or composition, containing these polypeptides or proteins.

For the purposes of this invention, the contacting can be effected in vitro, ex vivo or in vivo. When the cells are inhibited in vitro, the contacting is effected by mixing the composition or protein of this invention with the cell culture medium and then feeding the cells or by directly adding the composition or protein to the culture medium. Methods of determining an effective amount are well known to those of skill in the art.

This method also is useful to treat or prevent pathologies associated with abnormally proliferative cells in a subject in vivo. Thus, when the contacting is effected in vivo, an effective amount of the composition of this invention is administered to the subject in an amount effective to inhibit the proliferation of the cells in the subject. An effective amount of the pharmaceutical composition comprising described above is generally in the range of about 0.01 to 100 mg/kg body weight. An effective amount can be determined using methods known to those in the art. The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the amount of compositions of this invention required to obtain an effective dose in a subject depends on many factors including the age and general health of the subject as well as the route of administration and the number of treatments to be administered. For the purpose of this invention, "subject" means any vertebrate, such as an animal, mammal, human, or rat.

Methods of administering a pharmaceutical are well known in the art and include but are not limited to administration orally, intravenously, intramuscularly or intraperitoneal. Administration can be effected continuously or intermittently and will vary with the subject as is the case with other therapeutic recombinant proteins (Landmann et al., *J. Interferon Res.* 12(2):103–111 (1992); Aulitzky et al., *Eur. J. Cancer* 27(4):462–467 (1991); Lantz et al., *Cytokine* 2(6):402–406 (1990); Supersaxo et al., *Pharm. Res.* 5(8):472–476 (1988); Demetri et al., *J. Clin. Oncol.* 7(10:1545–1553 (1989); and LeMaistre et al., *Lancet* 337:1124–1125 (1991)).

Isolated nucleic acid molecules which encode amino acid sequences corresponding to the purified mammalian mitosin protein, mutein, active fragments thereof, otherwise referred herein as "equivalent proteins" or "equivalent polypeptides" and anti-mitosin antibody are further provided by this invention. As used herein, "nucleic acid" shall mean single and double stranded DNA, cDNA and mRNA. In one embodiment, this nucleic acid molecule encoding mitosin protein and fragments has the sequence or parts thereof shown in FIG. 8. Also included within the scope of this invention are nucleic acid molecules that hybridize under stringent conditions to the nucleic acid molecule or its complement, for example, the sequence of which is shown in FIG. 8. Such hybridizing nucleic acid molecules or probes, can by prepared, for example, by nick translation of the nucleic acid molecule of FIG. 8, in which case the hybridizing nucleic acid molecules can be random fragments of the molecule, the sequence of which is shown in FIG. 8. For methodology for the preparation of such fragments, see Sambrook et al., *Molecular Cloning: A Laboratory Manual* Cold Spring Harbor Press, Cold Spring Harbor, N.Y. (1989), incorporated herein by reference. Nucleic acid fragments of at least 10 nucleotides are useful as hybridization probes. Isolated nucleic acid fragments also are useful to generate novel peptides. These peptides, in turn, are useful as immunogens for the generation of polyclonal and monoclonal antibodies. Methods of preparing and using the probes and immunogens are well known in the art.

The nucleic acid sequences also are useful to promote cell division and proliferation of a cell. The nucleic acid molecule is inserted into the cell, the cell is grown under conditions such that the nucleic acid is encoded to mitosin protein in an effective concentration so that the growth of the cell is inhibited. For the purposes of this invention, the nucleic acid can be inserted by liposomes or lipidated DNA or by other gene carriers such as viral vectors as disclosed in Sambrook et al., supra, incorporated herein by reference.

For the purpose of illustration only, a delivery system for insertion of a nucleic acid is a replication-incompetent retroviral vector. As used herein, the term "retroviral" includes, but is not limited to, a vector or delivery vehicle having the ability to selectively target and introduce the nucleic acid into dividing cells. As used herein, the terms "replication-incompetent" is defined as the inability to produce viral proteins, precluding spread of the vector in the infected host cell.

Another example of a replication-incompetent retroviral vector is LNL6 (Miller, A. D. et al., *BioTechniques* 7:980–990 (1989)). The methodology of using replication-incompetent retroviruses for retroviral-mediated gene transfer of gene markers is well established (Correll, P. H. et al., *PNAS USA* 86:8912 (1989); Bordignon, C. et al., *PNAS USA* 86:8912–52 (1989); Culver, K. et al., *PNAS USA* 88:3155 (1991); Rill, D. R. et al., *Blood* 79(10):2694–700 (1991)). Clinical investigations have shown that there are few or no adverse effects associated with the viral vectors (43: Anderson, *Science* 256:808–13 (1992)).

Other vectors are suitable for use in this invention and will be selected for efficient delivery of the nucleic acid encoding the mitosin genes, or the fragments or mutants thereof. The nucleic acid can be DNA, cDNA or RNA. Such vectors include adenovirus vectors, specifically replication-deficient recombinant adenovirus vectors as described in Siegfried, W., *Exp. Clin. Endocrinol.*, 101:7–11 (1993); Rosenfeld, M. A. et al., *Cell* 68:143–155 (1992); Rich, D. P. et al., *Human Gene Therapy*, 4:460–476 (1993); and Lemarchand, P., et al., *Proc. Natl. Acad. Sci. USA* 89:6482–6486 (1992).

In a separate embodiment, an isolated nucleic acid molecule of this invention is operatively linked to a promoter of RNA transcription. These nucleic acid molecules are useful for the recombinant production of mitosin proteins and polypeptides or as vectors for use in gene therapy.

This invention also provides a vector having inserted therein an isolated nucleic acid molecule described above. For example, suitable vectors can be, but are not limited to a plasmid, a cosmid, or a viral vector. For examples of suitable vectors, see Sambrook et al., supra, and Zhu et al., *Science* 261:209–211 (1993), each incorporated herein by reference. When inserted into a suitable host cell, e.g., a procaryotic or a eucaryotic cell, mitosin can be recombinantly produced. Suitable host cells can include mammalian cells, insect cells, yeast cells, and bacterial cells. See Sambrook et al., supra., incorporated herein by reference.

A method of producing recombinant mitosin or mitosin fragments, by growing the host cells described above under suitable conditions such that the nucleic acid encoding mitosin or its fragment, is expressed, is provided by this invention. Suitable conditions can be determined using methods well known to those of skill in the art, see for example, Sambrook et al., supra, incorporated herein by reference. Proteins and polypeptide produced in this manner also are provided by this invention.

Also provided by this invention is an antibody capable of specifically forming a complex with mitosin protein or a fragment thereof. The term "antibody" includes polyclonal antibodies and monoclonal antibodies. The antibodies include, but are not limited to mouse, rat, rabbit or human monoclonal antibodies.

As used herein, a "antibody or polyclonal antibody" means a protein that is produced in response to immunization with an antigen or receptor. The term "monoclonal antibody" means an immunoglobulin derived from a single clone of cells. All monoclonal antibodies derived from the clone are chemically and structurally identical, and specific for a single antigenic determinant.

Laboratory methods for producing polyclonal antibodies and monoclonal antibodies are known in the art, see Harlow and Lane, *Antibodies: A Laboratory Manual*, Cold Spring Harbor Laboratory, New York (1988), incorporated herein by reference. The monoclonal antibodies of this invention can be biologically produced by introducing mitosin or a fragment thereof into an animal, e.g., a mouse or a rabbit. The details of this process are well known and will not be repeated here. However, basically it involves injecting a mouse, or other suitable animal, with an immunogen. The mouse is subsequently sacrificed and cells taken from its spleen are fused with myeloma cells. The results is a hybrid cell, referred to as a "hybridoma," that reproduces in vitro. The population of hybridomas is screened and manipulated so as to isolate individual clones each of which secretes a single antibody species to the antigen. Each individual antibody species obtained in this way is the product of a single B cell from the immune animal generated in response to a specific antigenic site recognized on the immunogenic substance. When an immunogenic substance is introduced into a living host, the host's immune system responds by producing antibodies to all the recognizable sites on the substance. This "shotgun" approach to producing antibodies to combat the invader results in the production of antibodies of differing affinities and specificities for the immunogenic substance. After the different hybridoma cell lines are screened to identify those that produce antibody to the desired antigen, the antibodies produced by the individual hybridoma cell lines are preferably screened to identify those having the highest affinity for the immunogenic substance stimulating their original production before selection for use in the present invention. The hybridoma cells producing the monoclonal antibodies of this invention also are provided. Monoclonal antibodies produced in this manner include, but are not limited to the monoclonal antibodies described below.

Thus, using the mitosin protein or fragment thereof, and well known methods, one of skill in the art can produce and screen the hybridoma cells and antibodies of this invention for antibodies having the ability to bind mitosin.

This invention also provides biological active fragments of the polyclonal and monoclonal antibodies described above. These "antibody fragments" retain some ability to selectively bind with its antigen or immunogen. Such antibody fragments can include, but are not limited to:

(1) Fab, the fragment which contains a monovalent antigen-binding fragment of an antibody molecule produced by digestion with the enzyme papain to yield an intact light chain and a portion of one heavy chain;

(2) Fab', the fragment of an antibody molecule obtained by treating with pepsin, followed by reduction, to yield an intact light chain and a portion of the heavy chain; two Fab' fragments are obtained per antibody molecule;

(3) (Fab')$_2$, the fragment of the antibody that is obtained by treating with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) SCA, defined as a genetically engineered molecule containing the variable region of the light chain, the variable region of the heavy chain, linked by a suitable polypeptide linker as a genetically fused single chain molecule.

Methods of making these fragments are known in the art, see for example, Harlow and Lane, supra, incorporated herein by reference.

Specific examples of "biologically active antibody fragment" include the CDR regions of the antibodies.

Anti-idiotypic peptides specifically reactive with the antibodies or biologically active fragments thereof also are provided by this invention. As used herein, "anti-idiotyptic peptides" are purified antibodies from one species that are injected into a distant species and recognized as foreign antigens and elicit a strong humoral immune response. For a discussion of general methodology, see Harlow and Lane, supra, incorporated herein by reference.

Also encompassed by this invention are proteins or polypeptides that have been recombinantly produced, biochemically synthesized, chemically synthesized or chemically modified, that retain the ability to bind mitosin or a fragment thereof, as the corresponding native polyclonal or monoclonal antibody. The ability to bind with an antigen or immunogen is determined by antigen-binding assays known in the art such as antibody capture assays. See for example, Harlow and Lane, supra, incorporated herein by reference.

In one embodiment, the antibody is linked to a detectable agent, useful to detect the mitosin protein and fragments in a sample using standard immunochemical techniques such as immunohistochemistry as described by Harlow and Lane, supra, incorporated herein by reference.

In a separate embodiment, the antibody is administered to bind to mitosin and thereby inhibit its function within the cell. The antibody is administered by methods well known to those of skill in the art and in an effective concentration such that mitosin function is inhibited. The antibody also can be used therapeutically to inhibit cell growth or proliferation as described above.

Another aspect of this invention is a diagnostic one, utilizing the antibodies and nucleic acid molecules of this invention are useful to detect and determine the presence of mitosin in a cell or a sample taken from a patient. Because the presence of mitosin in a cell is an index of proliferation, and thus, an important indicator of hyperproliferative disease, such as cancer, an excessive amount of mitosin is indicative of a hyperproliferative and/or pre-malignant state of the cell. Examples of the types of immunoassay such as EIA and RIA utilizing the antibodies of the instant invention are known in the art. Examples of these formats can be found, for example, in C. P. Prince, D. J. Newman, editors, Principals and Practice of Immunoassay, Stockton Press, New York, 1991, herein incorporated by reference. Nucleic acid hybridization assays utilizing the instant nucleic acids can be found in B. D. Hames and S. J. Higgins, editors, Nucleic Acid Hybridization, IRL Press, Oxford, 1991, and Larry J. Kricka, editor, Nonisotopic DNA Probe Techniques, San Diego, Calif., 1992.

The above-identified proteins, polypeptides, nucleic acids, antibodies, and fragments thereof are useful for the preparation of medicaments for therapy, as outlined above.

The invention will now be described in greater detail by reference to the following examples. These examples are intended to illustrate but not limit the invention.

EXPERIMENTAL PROCEDURES

EXPERIMENT I

CLONING AND SEQUENCING OF MITOSIN

Ten (10) μg of total RNA extracted from different cell lines Y79 and K562 was subjected to Northern blotting as described by Shan, B. et al., Mol. Cell. Biol., 12:5620–5631 (1992), incorporated herein by reference, using radiolabeled mitosin cDNA as a probe. The cloning of cDNAs for RB-associated proteins was performed according to the method described previously in Shan, B. et al., supra, incorporated herein by reference. Briefly, an immunocomplex ("RB-sandwich") formed by purified p56-RB, anti-RB antibody 0.47, and an alkaline phosphatase-conjugated secondary antibody was used as a probe to screen lambda-gt11 expression human cDNA libraries, while a "sandwich" without RB was used as a negative control. Two additional libraries were used for rescreening: (1) a Y79 cDNA library prepared as described in Lee, W.-H. et al. Science 235:1394–1399 (1987), incorporated herein by reference; and (2) a K562 cDNA library (a gift from Dr. M.-L. Chu at Thomas Jefferson University, Philadelphia, Pa.). The orientation of internal EcoRI fragments was determined by both comparing overlapping clones in appropriate regions and directly sequencing through intact EcoRI junctions. Direct sequencing also eliminates the possibility of missing other small EcoRI fragments. DNA sequencing was performed using the dideoxynucleotide termination method (Sambrook et al., supra) and the sequences were analyzed by a computer program provided by DNASTAR (Madison, Wis.).

EXPERIMENT II

PREPARATION OF POLYCLONAL ANTI-MITOSIN ANTIBODIES

To prepare polyclonal antibodies against mitosin, three fusion proteins with different portions of mitosin, GST-10Bgl (comprising amino acid residues 1128–1462 of FIG. 8B), GST-10Stu (comprising amino acid residues 1461–1856 of FIG. 8B), or MBP-10C (comprising amino acid residues 1853–2482 of FIG. 8B), were generated, using vectors (Riggs, P., in Current Protocols in Molecular Biology, Ausebel, F. M. et al. (eds.), New York (1990); Smith and Johnson, Gene 67:31–40 (1988)) capable of expressing fusion protein of either glutathione S-transferase (GST) or maltose-binding protein (MBP). Animals were immunized subcutaneously, using standard procedures, with these bacterially expressed fusion proteins. Immune sera (anti-10Bgl, anti-10Stu, and anti-10C) were preabsorbed with either GSB bound to glutathione resin or MBP bound to amylose resin, depending on the source of antigen, for 1 hour at 4° C. The flow-through was then incubated for two hours at 4° C. with pre-blocked (in PBS+1% BSA) Immobilon-P membrane (Millipore) containing 500 μg fusion protein electrophoretically transferred from an SDS-polyacrylamide gel. After extensive washing with phosphate buffered saline (PBS), specific antibodies were eluted out with aliquots of 0.2M Glycine-Hcl, pH 2.3, and the eluent was neutralized with 3M Tris-Hcl, pH 8.0. The specifities of these antibodies were further tested by blotting analysis using corresponding antigens.

EXPERIMENT III

IDENTIFICATION OF THE MITOSIN PROTEIN

To identify the cellular gene product of mitosin, $5 \times 10^5$ actively growing HeLa cells were lysed directly in boiling SDS-loading buffer and the lysate was subjected to 3–12% gradient SDS-PAGE and electrophoretic transfer to an Immobilon-P membrane (Millipore). Three adjacent lanes with the same sample were excised and each lane probed separately with one of the three antibodies. A sample prepared from rabbit backbone muscles also was loaded side by side with the HeLa cell lysate. The position of nebulin in this sample, which served as a 770 kD marker, was visualized by probing with a monoclonal antibody provided by Dr. K. Wang (University of Texas, Austin, Tex.), made by the method described in Kruger, M. et al. J. Cell Biol. 115:97–107 (1991), incorporated herein by reference.

EXPERIMENT IV

DISTRIBUTION OF MITOSIN DURING THE CELL CYCLE

Monkey kidney CV1 cells were grown directly upon glass coverslips and were synchronized as described below in Example V and in the description of FIG. 4. Coverslips bearing samples were washed in PBS and fixed for 10 minutes in cold absolute methanol. After hydration in TBST (0.1M Tris, pH 7.4, 0.15M NaCl, 0.1% Tween 20), cells were blocked with TBST containing 5% dry milk (TBST- M). A one-hour incubation with rabbit anti-10C diluted in TBST-M was followed by a 30-minute incubation with goat anti-rabbit IgG conjugated with FITC (1:100) (FisherBiotech). After washing in TBST, coverslips were mounted in Permafluor (Lipshaw-Immunonon, Inc.). Laser-scanning confocal microscopy was performed with a Zeiss LSM III, equipped with Ar and HeNe lasers. Optical sections (0.25 µm) were digitized and superimposed with Normarski differential interference contrast images and recorded directly onto Ektachrome 100 35 mm film (FocusGraphics, Inc.).

EXPERIMENT V

ANALYSIS OF CELL EXTRACTS FROM SYNCHRONIZED CELL POPULATIONS BY WESTERN BLOTTING

Normal monkey kidney CV1 cells were synchronized with lovastatin, hydroxyurea and nocodazole and released for different periods of time to obtain fairly uniform populations in different cell-cycle stages. Two plates of cells growing simultaneously under identical conditions were prepared for each sample, one for immunoblotting and the other for flow cytometry. For samples released from early G1 or G1/S, $1.5 \times 10^6$ cells were plated per 100 mm petri dish in fresh, complete Dulbecco's modified Eagle medium (DMEM) plus 10% serum. Lovastatin (40 µM) was added for 36 hours to arrest cells in early G1 (Keyomarsi et al., *Cancer Res.* 51:3602–3609 (1991)); cells were then released by adding mevalonic acid lactone to a final concentration of 4 mM. For synchronization at the G1/S boundary, hydroxyurea (0.5 mM) (Adams and Lindsay, *J. Biol. Chem.* 242:1314–1317 (1967)) was added for 24 hours; cells were released from the arrest by washing three times with PBS. Samples were collected at different time points as noted. For samples released from nocodazole (prometaphase) block $6 \times 10^6$ cells were plated per 150 mm Petri dish, in the presence of hydroxyurea for 24 hours. After washing three times with PBS, medium with nocadazole (0.4 µg/ml) was added. Mitotic cells were gently shaken off 12 hours later, spun down, and resuspended in PBS. Following three more washes with PBS, aliquots of cells ($1.5 \times 10^6$) were replated and collected again at different time points. For immunoblotting, cells were collected into PBS from one set of dishes, using rubber policemen, then spun down and directly lysed by boiling in 100 µl SDS-loading buffer. Another set was trypsinized, spun down, washed once with PBS, and resuspended in 0.3 ml of PBS. Each sample was vortexed gently while 1 ml of methanol was added dropwise to fix cells for flow cytometry. Fixed samples were stored at 4° C. until needed.

$2 \times 10^6$ CV1 cells, released for 4 hours from G1/S boundary (hydroxyurea block), were labeled with $^{32}P$ orthophosphate (0.25 mCi/ml final) in DME medium supplemented with 10% dialyzed fetal bovine serum for 2 hours. Equal amount of cells were collected by mitotic shake-off after sequential double blocking with hydroxyurea and nocodazole, as described in the legend to FIG. 4. These two different cell samples were lysed in cold Ab buffer (20 mM Tris-HCl, pH 7.4, 50 mM NaCl, 50 mM NaF, 1 mM EDTA, 0.5% NP-40, 0.5% deoxycholate, 0.5% SDS, plus leupeptin, aprotinin, antipain, 1 µg/ml each), sonicated briefly, clarified by centrifugation, and then subjected to immunoprecipitation using saturating amount of anti-10Bgl. Immunocomplexes were precipitated by protein A-Sepharose beads. The beads were then washed twice with RIPA buffer (10 mM Tris, pH 7.4, 150 mM NaCl, 1% NP-40, 1% deoxycholate, 0.1% SDS, plus protease inhibitors), once with high salt buffer (10 mM Tris, pH 7.4, 1M NaCl, 1% NP-40, 1% deoxycholate, plus protease inhibitors), twice with Tris-buffered saline, and three times with sterile deionized water. Immunoprecipitates from samples were divided into two equal aliquots. Twenty (20) units calf intestinal alkaline phosphatase (CIA), 20 U/µl (Boehringer Mannheim Biochemica) in 25 µl working buffer (50 mM Tris-HCl, pH 8.5, 0.1 mM EDTA) was added to one aliquot while only 25 µl buffer (without CIAP) was added to the remaining aliquot. Both fractions were incubated at 37° C. for 10 minutes. Samples were boiled in SDS-loading buffer, separated by 3–12% gradient SDS-PAGE and transferred to Immobilon-P membrane. The blots were then subject to immunoblotting and/or autoradiography.

EXPERIMENT VI

DNA CONTENT ANALYSIS BY FLOW CYTOMETRY

CV1 cells were trypsinized and washed once with PBS. After fixation in 70% methanol and RNase digestion, cells were stained with propidium iodide for DNA content analysis. For two color selection, transfected cells were fixed sequentially in 70% methanol and cold absolute methanol, stained with anti-flag mAb M2 (IBI) plus FITC-conjugated secondary antibody (Fisher Biotech) before propidium iodide staining. The DNA content of both the FITC positive cells and the FITC negative cells were analyzed.

EXPERIMENT VII

CO-IMMUNOPRECIPITATION

Co-immunoprecipitation was performed following the method previously described (Durfee et al., *Genes & Development* 7:555–569 (1993)) using mitotic cells collected from nocodazole-synchronized CV1 populations.

EXPERIMENT VIII

PLASMID CONSTRUCTION AND TRANSFECTION

The full-length cDNA of mitosin was obtained by ligation of appropriate cDNA fragments isolated from cDNA libraries. An artificial BamH I site was inserted immediately upstream of the first ATG. All ligated junctions of cDNAs were sequenced to ensure the correct ligation and modification.

To distinguish the exogenously expressed mitosin from the endogenous form, an ATG containing sequence encoding the flag-tag (Hopp et al., *Biotech* 6:1205–1210 (1988)) was inserted between the multiple cloning sites Kpn I and Hind III of pCEP4 (Invitrogen, San Diego, Calif.) to create pCEP4F. The full-length cDNA of mitosin (nucleotides 543–8241) was then cloned downstream of the flag epitope to make pCF-10. Other deletion mutants (pCF-10Acc, nucleotides 543–6222; pCF-10RV, nucleotides 543–3951; pCF-10NN, nucleotides 4381–6582; and pCF10Xh, nucleotides 3397–8241) were also constructed in this way using appropriate restriction sites.

Transfection was performed with CV1 cells by calcium phosphate DNA precipitation method as previously described (Shan et. al., *Mol. Cell. Biol.* 12:5620–5631 (1992)). 10 µg of construct DNA was mixed with 10 µg of carrier DNA (pGEM-3Z, Promega, Madison, Wis.) for each transfection. Cells were collected or fixed three days after transfection for immunofluorescence microscopy, or flow cytometry. When colony selection was required, cells were diluted and re-plated two days after transfection. Drug-resistant colonies were selected in the presence of hygromycin B (200 μg/ml) for two weeks.

The Rb binding domain of mitosin was located by constructing and expressing fusion proteins of various sites which encompass the C-terminal domain of the peptide. For the in vitro Rb-binding assay, different deletion mutants were constructed from MBP-10. The 3'-coding sequence of AP10 was deleted to either the Hind III site at nucleotide position 7,427, or Nhe I site at nucleotide position 6,582 to express MBP-10/H (amino acid residues 1,853–2,296) and MBP-10/NB (residues 1853–2041). The 5'-coding sequence of AP10 was partially deleted to express MBP-10KN (residues 2014–2482) and MBP-10NI (residues 2014–2482) and MBP-10NI (residues 2271–2482), respectively. A BspH I-Nco I fragment (nucleotides 7529–7664) containing sequences homologous to the Rb-binding domain in E2F-1 was cloned into the unique Nco I site of pGEX-PK, a vector derived from pGEX-2T (Pharmacia Biotech, Piscataway, N.J.) to express GST-1045 (residues 2330–2375).

Expression of fusion proteins was induced by adding IPTG to a final concentration of 0.1 mM into an exponentially growing bacterial culture at 30° C. After 1 hour of induction, bacteria were collected and lysed by mild sonication. Fusion proteins were purified either by electroelution after SDS-PAGE or by affinity chromatography.

EXPERIMENT IX

INDIRECT IMMUNOFLUORESCENCE STUDIES

CV1 cells were washed in PBS and fixed for 10 minutes in cold absolute methanol or 4% paraformaldehyde in PBS for 20 min. Both fixatives resulted in the same pattern of immunostaining. After hydration in TBST (100 mM tris-HCL, pH 7.4, 150 mM NaCl, 0.1% Tween 20), cells were clocked in TBST containing 5% dry milk (TBST-M). A one hour incubation with a suitable antibody diluted in TBST-M was followed by three washed, then by another one-hour incubation with fluorochrome-conjugated second antibody (1:100) (Fisher Biotech). Nuclear DNA was then stained by DAPI (0.5 μg/ml) to indicate different stages of M phase. Competition experiments were performed by including competitors (GST-10Bgl, GST-10Stu, MBP-10, or MBP; 10 μg/ml) to dilute antibodies. Chromosome spreads were prepared by centrifuging KCl-swollen CV1 cells onto cover slips (Earnshaw et al., *J. Cell Biol.* 98:352–357 (1984)) and then processed as described above, except that chromosomal DNA was stained by propidium iodide (1 μg/ml; Sigma) after RNase digestion. Samples were mounted in Permafluor (Lipshaw-Immunonon, Inc.). Laser-scanning confocal microscopy was performed with Zeiss LSM 310, equipped with Ar and HeNe lasers. Optical sections were digitized and superimposed with Normarski differential contrast images.

EXPERIMENTAL DISCUSSION

Figure 1A:
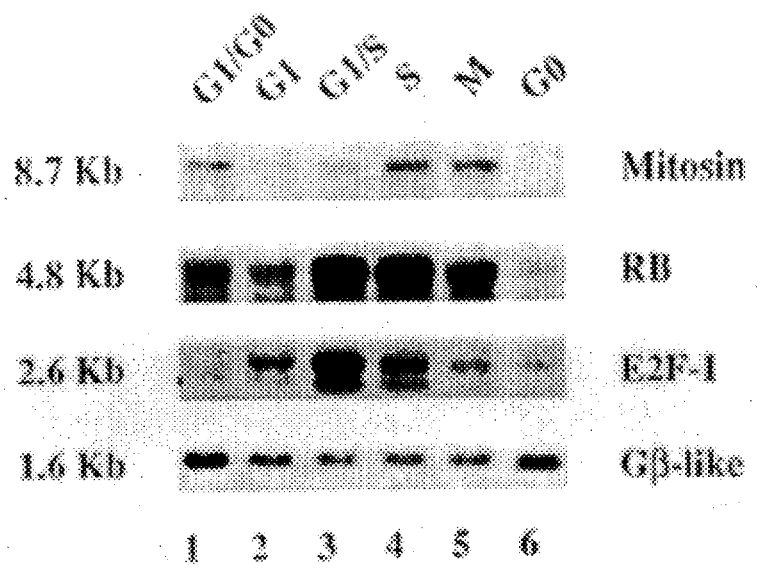
FIGS. 1A and 1B: Mitosin mRNA is Expressed in a Cell-cycle Dependent Manner.
Figure 1B:
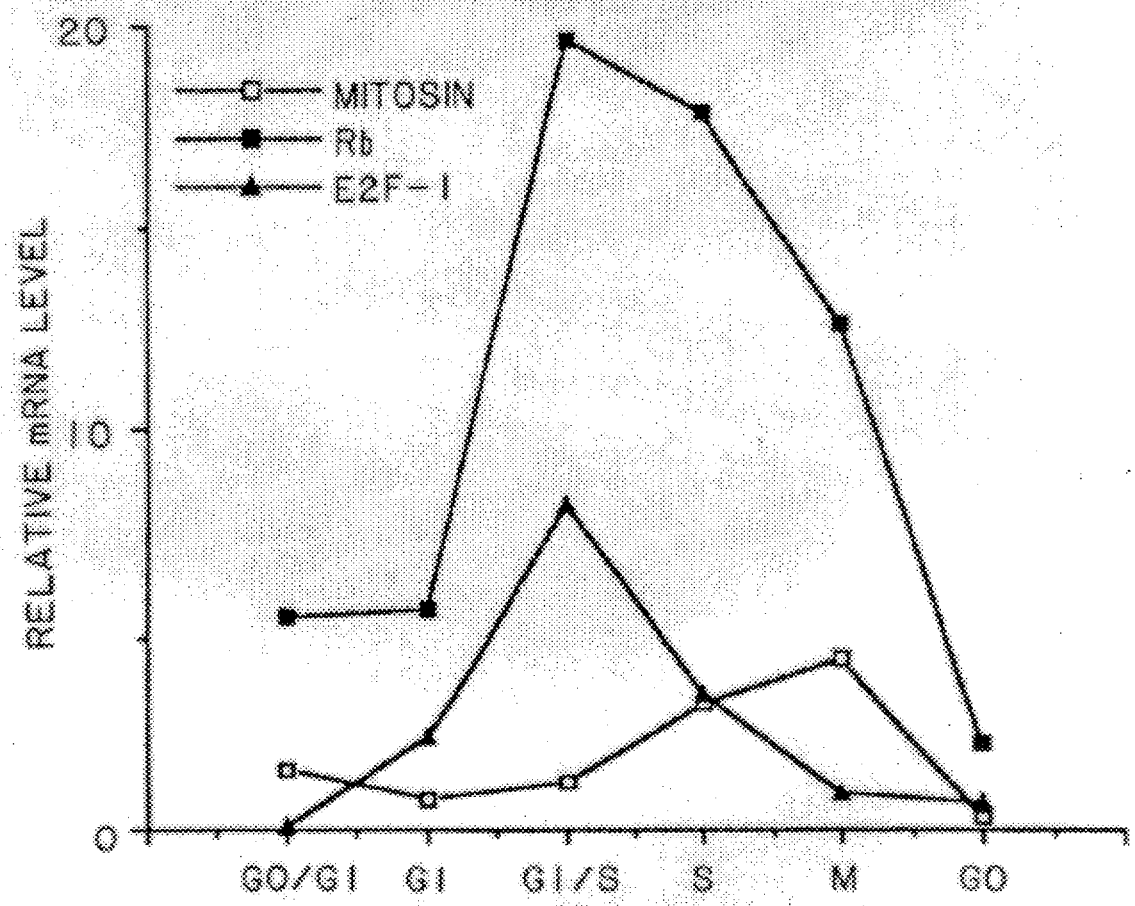

The function of Rb in cell growth and differentiation is believed to be exerted through association with the cellular proteins (Goodrich and Lee, *Biochem. Biophys. Acta.* 1155:43–61 (1993); Weinberg, R. A., *Science* 254:1138–1146 (1991)). Mitosin cDNA was obtained using the "Rb-Sandwich" method as described previously (Shan et al., *Mol. Cell. Biol.* 12:5620–5631 (1992). Because Rb function is modulated in concert with the cell division cycle, the expression pattern of this gene in synchronized primate cells was examined. mRNA levels of mitosin in monkey kidney CV1 cells were low in G1, gradually increased after the G1/S boundary, and peaked in M phase (FIG. 1). This expression profile differed from those of three other genes: the transcription factor E2F-1, which is predominantly expressed at the G1/S boundary; RB, which is expressed throughout the cell cycle with 3–4 fold increase during S phase (Shan et al., *Mol. Cell. Biol.* 14: 299–309 (1994)), and the Gβ-like gene (Gullemont et al., *Proc. Natl. Acad. Sci. USA* 86:4594–4598 (1989)), which is expressed uniformly throughout the cell-cycle (Shan et al., *Mol. Cell. Biol.* 12:5620–5631 (1992)) and served as an internal control for RNA loading. Mitosin mRNA was also detected in all human tumor cell lines tested, including HeLa (cervical tumor), Molt4 (leukemia), and Saos2 (osteosarcoma), suggesting that this gene is widely transcribed in human cells.

Three distinct polyclonal antibodies against three different regions of the deduced gene product were raised in mice or rabbits using GST or MBP fusion proteins as antigens (see experimental procedures). After purification by affinity chromatography, these antibodies, termed α10Bgl, α10Stu, and α10C, all recognized a cellular protein with molecular weight approximately 350 Kd (kilodaltons) in HeLa cells by immunoblotting (FIG. 2). Detection of this protein was specifically abolished by corresponding antigen competitors (FIG. 2). The same protein was also detected in other cell lines including monkey kidney CV1, human leukemia Molt4, and osteosarcoma Saos-2. By immunostaining (FIG. 3 A1) and subcellular fractionation, this protein was located in the nucleus. The immunostaining pattern by α10C was not affected by MBP competitor (FIG. 3 A3). Similar competition results were obtained when using other anti-mitosin antibodies, suggesting that the staining pattern by these antibodies is specific to mitosin.

Interestingly, only 20–30% of unsynchronized populations were immune-positive (FIG. 3 A1), regardless of method of fixation, suggesting that the levels of mitosin protein were also cell cycle-dependent. When CV1 cells were synchronized at early G1 by lovastatin treatment (Keyomarsi et al., *Cancer Res.* 51:3602–3609 (1991)) and then released for 1 hour, virtually all of the cells were negative for mitosin. When hydroxyurea-treated cells were released from arrest at the G1/S boundary (Adam and Lindsay, *J. Biol. Chem.* 242:1314–1317 (1967)), more than 90% exhibited nuclear staining. Cell nuclei were uniformly labeled except for nucleoli (FIG. 3 B1), a pattern which remained unchanged through the rest of interphase. The localization of mitosin, however, changed dramatically during M phase. In late G2 or early prophase, brightly staining foci began to appear (FIG. 3 B2). Following chromosome condensation, more discrete parts of fluorescent spots were observed (FIG. 3 B3). During metaphase, bright and discrete dot staining was visible on the chromosomes at the midplate, in addition to some labeling in the spindle pole regions (FIG. 3 B4). The intensity of the fluorescent dots decreased during anaphase; the staining at the spindle region became predominant (FIG. 3 B5, B6). During telophase, the midbody was labeled while the cytoplasmic staining decreased (FIG. 3 B7, B8). Following completion of cytokinesis, no immunostaining was observed. The mitotic stages of cells described above were determined by DAPI staining of nuclear DNA.

To substantiate the mitosin is located at the centromere, chromosome spreads prepared from nocodazole-arrested CV1 cells were used for immunostaining. As shown in FIG. 3 C5–C8, mitosin was unambiguously found at the centromere region. The specificity of the centromeric staining was further confirmed by competition experiments (FIG. 3, C1–C4). Identical staining patterns were obtained with either α10Bgl or α10Stu. These results confirmed that mitosin transiently associated with the centromere in M phase.

To corroborate the immunostaining observations, synchronized cell populations by Western blotting were analyzed. Using lovastatin (Keyomarsi et al., *Cancer Res.* 51:3602–3609 (1991)), hydroxyurea (Adams and Lindsay, *J. Biol. Chem.* 242:1314–1317 (1967)), and nocodazole (Zieve et al., *Exp. Cell Res.* 126:397–405 (1980)), CV1 cells were synchronized at various stages of the cell-cycle. The degree of synchronization was confirmed by the expression pattern of Rb (FIG. 4B) (Buchkovich et al., *Cell* 58:1097–105 (1989); Chen et al., *Cell* 58:1193–1198 (1989)), as well as flow cytometry (FIG. 4D). Mitosin was virtually undetectable in G1 (lane 1–5, lane 14–16), appeared when cells entered S phase, peaked in M phase (lane 6–13) and then rapidly disappeared (lane 14–15). In contrast, the level of Gβ-like protein remained unchanged throughout the cell cycle (FIG. 4C). In addition to the difference in protein quantity, the mobility of mitosin in SDS-PAGE gradually decreased, suggesting the possibility of post-translational modification. The appearance of the multiple, slowly migrating mitosin isoforms suggested stepwise modification between S phase and prophase of mitosis. After prometaphase (the block point of nocodazole), only the slowest migrating form was present and it disappeared rapidly thereafter.

It was speculated that the mobility change of mitosin, similar to that of RB, might be due to phosphorylation. To test this hypothesis, cells synchronized in S phase were radioactively labeled with $^{32}P$ orthophosphate. Mitosin was then immunoprecipitated and treated with calf intestinal alkaline phosphatase (CIAP). As shown in FIG. 5B, mitosin can be labeled with $^{32}P$ and the labeled group can be removed by incubation with CIAP. The same gel was then blotted with an anti-mitosin antibody to show the presence of unlabeled mitosin (FIG. 5A). Similar experiments were performed using cells synchronized in M phase (FIG. 5C); here, the isoform of mitosin with the slowest mobility can be converted into the fast-migrating isoform by treatment with CIAP, thus proving that phosphorylation is the only cause of the mobility alteration. The existence of multiple, more slowly migrating bands implicates a difference in either the extent or the specificity of phosphorylation. The temporal pattern of mitosin phosphorylation coincides directly with its spatial reorganization, suggesting that phosphorylation may be critical for these dynamic changes. It is well known that many proteins are regulated by phosphorylation through cyclin-dependent kinase (CDK) during the cell cycle progression. Although there are no typical consensus phosphorylation sites for CDKs [i.e., (ST)PX(KR)] (SEQ. ID NO:1) (Shenoy et al., *Cell* 57:763 (1989)) in mitosin, there are four proline-derived kinase sites [i.e., (ST)P(KR)] (SEQ. ID NO: 2) and five cAMP or cGMP-dependent kinase sites (Feramisco et al., *J. Biol. Chem.* 255:4240–4245 (1980) and Glass et al., *J. Biol. Chem.* 261:2987–2993 (1986)), indicating that multiple potential sites are available for phosphorylation.

Since mitosin was isolated as a candidate Rb-associated protein, the interaction of Rb with mitosin in mammalian cells was examined. Most of the effect was placed on M phase because (1) mitosin was undetectable in G1; (2) mitosin was relatively insoluble in S phase and (3) only little or no hypophosphorylated Rb, to which cellular proteins have been shown to bind, is present in S phase. Co-immunoprecipitation with anti-Rb monoclonal antibody 11D7 was performed to test such an interaction using synchronized CV1 cells at prometaphase by nocodazole treatment. As shown in FIG. 6, mitosin co-immunoprecipitated with Rb protein (FIG. 6, lanes 3 and 5). Under the similar conditions, mitosin was not detected in immunoprecipitates by monoclonal antibody against bacterial GST (FIG. 6, lanes 2 and 4).

To precisely define a region of mitosin responsible for binding to Rb, the original isolated clone, AP10, containing about an approximately 60 Kd portion of the C-terminal region, was fused to maltose-binding protein (MBP) and express in *E. Coli.* Four additional constructs containing deletion fragments of AP10 (FIG. 7, panel C), and the first 300 amino acid of simian virus 40 (SV40) large T antigen, were fused to MBP and expressed. MBP alone served as a negative control. These seven MBP fusion proteins (FIG. 7, lanes 8–14) were blotted and probed with the "Rb-sandwich" (Shan et. al, *Mol. Cell. Biol.* 12:5620–5631 (1992)) (FIG. 7, lanes 1–7). Only the fusion proteins containing the C-terminal 211 amino acids of mitosin bound to Rb (FIG. 7, lanes 2, 5, 6) with MBP-T antigen (lane 1) serving as a positive control. The sequence comparison indicates that amino acid residues 2328–2360 of mitosin are 51% homologous and 27% identical to the surrounding region of the known Rb-binding domain of E2F-1 (Helin et al., *Cell* 70:337–350 (1992)) (FIG. 7, panel D).

To further demonstrate that this region of mitosin is sufficient to bind Rb, a mitosin fragment containing amino acid residues 2,330–2,375 was fused with glutathione S-transferase (GST) to express fusion protein GST-1045. As shown in FIG. 7, both GST-T antigen (lane 15) and GST-1045 (lane 17) bound to Rb while GST alone (lane 16) did not. Thus mitosin can bind to Rb as indicated by their co-immunoprecipitation in cell lysates as well as directly probing Western blot containing mitosin with the "Rb-Sandwich".

To further characterize mitosin, the full-length cDNA was completely sequenced and its primary amino acid sequence was deduced. Four of the cDNA clones originally isolated by the "Rb-Sandwich" screening (Shan et al. *Mol. Cell. Biol.* 12:5620–5631 (1992)) shared identical 3' sequences of approximately 2 Kb. A series of overlapping clones spanning 8,789 bp was isolated by multiple screens of several different cDNA libraries (FIG. 8A). The longest open reading frame (ORF) of 7,446 bp encoded an acidic protein (pI 4.8) of 2,482 amino acid residues. The existence of multiple stop codons in all three reading frames upstream of the first ATG strongly suggested that the cDNA sequence defined by these clones was full-length (FIG. 8B).

The deduced amino acid sequence of mitosin exhibits its novelty. It does not share significant homology with any known proteins in GENEBANK. Interestingly, this protein is predicted to contain a pair of highly charged tandem repeats separate by two proline residues (FIG. 8C). The first repeat (residues 1,480 to 1,657) is 62% identical to the second (residues 1,662 to 1,839). This internal repeat region is flanked by two blocks of leucine heptad repeats (Landschultz et al., *Science* 240:1759–1763 (1988)). Additionally, two leucine repeats are found near the N-terminal region; the other two are found closely to the C-terminal region. The secondary structure of this protein is predicted to be mostly α-helical, except for the extreme C-terminal region of 220 residues. This C-terminal region is basic (pI 10.02), proline-rich, containing a bipartite nuclear targeting signal (Dingwall and Laskey, *TIBS* 16:478–481 (1991)) and the Rb-binding region.

The cell-dependent expression of mitosin and its physical association with the kinetochore/centromere suggest a role for this protein in M phase. To further substantiate this notion, full-length and truncated mutants of mitosin tagged with the flag epitope (Hopp et al., *Biotech* 6:1205–1210 (1988)) at their N-termini (constructs "A" to "E") (FIG. 9) were expressed in CV1 cells using the pCEP4 vector. This vector utilizes a CMV promotor to drive transcription, carries a hygromycin-resistant gene for selection, and replicates episomally (Invitrogen, La Jolla, Calif.). Expression of the epitope-tagged proteins was confirmed by indirect immunofluorescence with (i) mouse monoclonal anti-flag antibody and Texas Red-conjugated anti-mouse IgG secondary antibody, and (ii) rabbit polyclonal anti-mitosin antibody (α10C, recognizing the C-terminus of mitosin) and fluorescein isothiocyanate (FITC)-conjugated anti-rabbit IgG secondary antibody (FIG. 10). Both "A" and "E" fusion proteins localized to the nucleus, with additional, variable staining in the cytoplasm. All three of the C-terminus truncated mutants ("B", "C", "D"), however, were exclusively cytoplasmic, consistent with the nuclear targeting signal found in the C-terminus of mitosin (FIG. 8B).

To elucidate the effect of the overexpression on cell-cycle progression, CV1 cells were analyzed by two-parameter flow cytometry three days after transfection. As summarized in Table 1, cell fractions with 4N DNA content (G2/M phase) were largely increased and those with S phase DNA content were variably decreased in cells expressing any of the five constructs compared to non-expressing populations. Interestingly, there was no significant difference in the percentage of G0/G1 cells expressing any of the mitosin constructs. These results suggest that the inhibition of cell growth by these proteins may be at G2/M.

TABLE 1

THE EFFECT OF TRANSIENT EXPRESSION OF MITOSIN ON THE CELL DISTRIBUTION*

| Samples | Cell-Cycle Stages | G0/G1 (%) T1 | G0/G1 (%) T2 | S (%) T1 | S (%) T2 | G2/M (%) T1 | G2/M (%) T2 | Percentage of Expression** |
|---|---|---|---|---|---|---|---|---|
| A | FITC+ | 71 | 74 | 11 | 11 | 18 | 15 | 0.03 ± 0.01 |
|   | FITC− | 72 | 63 | 20 | 29 | 8 | 8 |  |
| B | FITC+ | 71 | 67 | 12 | 16 | 17 | 17 | 0.6 ± 0.1 |
|   | FITC− | 67 | 68 | 24 | 23 | 9 | 9 |  |
| C | FITC+ | 68 | 61 | 15 | 17 | 17 | 22 | 0.6 ± 0.1 |
|   | FITC− | 68 | 67 | 24 | 24 | 8 | 9 |  |
| D | FITC+ | 65 | 60 | 19 | 15 | 16 | 25 | 3.8 ± 0.7 |
|   | FITC− | 70 | 63 | 22 | 24 | 8 | 13 |  |
| E | FITC+ | 55 | 47 | 15 | 14 | 30 | 39 | 0.6 ± 0.1 |
|   | FITC− | 68 | 64 | 22 | 23 | 10 | 13 |  |

*Results from two separate experiments (T1 and T2) are listed;
**1 × 10⁶ CV1 cells was transfected for each construct; Samples were collected three days post-transfection; Cells expressing mitosin proteins are labeled FITC+ and vice versa Detailed microscopic analysis of these transfected cells revealed that an increased number of cells expressing exogenous mitosin "A" and "E" have larger nuclei (FIGS. 10A and E), suggesting the at the arrest may be at the stage of G2/M. On the other hand, when examining cells expressing B, C, and D, signs of improper cell division were common. In addition to an increased number of multinucleated cells (FIGS. 10B, C, and D), chromatin bridges between two newly divided cells were observed with 10–40 fold higher frequency when compared with flag-negative cells.

Inhibition of cell proliferation was examined in CV1 colonies after hygromycin-selection for 14 days (Table 2). In samples transfected with "A", "B", "C" or "E" constructs, only 1–4 flag positive cells were found in some colonies regardless of colony size. These positive cells usually were well separated form each other, implying that they were not actively dividing cells. The "D" construct caused less effect on cell division; the epitope tag was expressed in a large portion of cells in each individual colony. This result served as a useful negative control for the "A", "B", "C" and "E" constructs; furthermore, it suggested that inhibition of cell division may be a specific effect of these constructs.

TABLE 2

THE EFFECT OF ECTOPIC EXPRESSION OF MITOSIN ON CELL DIVISION

| CONSTRUCT | PERCENTAGE OF COLONIES WITH TR+ CELLS | AVERAGE NO. OF TR+ CELLS PER COLONY* | AVERAGE COLONY SITE |
|---|---|---|---|
| A | 20 | 1 | ≈100 |
| B | 55 | 2 | ≈70 |
| C | 73 | 3 | ≈100 |
| D | 96 | 33 | ≈55 |
| E | 31 | 1 | ≈100 |

*Only colonies with TR+ cells are analyzed

Recently, proteins with similar properties and functions have been cloned. For example, CENP-E, a cytoplasmic protein with a kinesin-like motor, has somewhat similar patterns of cell cycle regulation. Cells in G1 and early S phases have little detectable CENP-E, but levels of the protein increase sharply during late S and G2/M. CENP-E associates with kinetochores during congression, relocates to spindle midzones at anaphase, and is discarded or degraded at the end of cell division. CENP-E is believed to serve as an organizing center, facilitating microtubule-kinetochore interaction. Whereas CENP-E is a cytoplasmic protein equipped with both kinesin and microtubule-binding domains, mitosin, however, is a nuclear protein with tandem repeats and multiple blocks of leucine heptad repeats. Based on the immunostaining data and the potential interaction sites of mitosin, it appears that mitosin can function as a bridge to link chromosomes to kinetochores and thereby allow the chromosome to move during mitosis. If so, mitosin should interact with CENP, other centromeric proteins, and/or DNA.

Based on the expression-screening data, the C-terminal one-fourth of mitosin binds to the N-terminal truncated p56-RB protein in vitro. The C-terminal 200 amino acid residues of mitosin has been further defined to be responsible for such binding.

Although the invention has been described with reference to the above embodiments, it should be understood that various modifications can be made without departing from the spirit of the invention. Accordingly, the invention is limited only by the claims that follow.

What is claimed is:

1. An isolated nucleic acid molecule which encodes a protein comprising the amino acid sequence of SEQ. ID NO. 6.

2. An isolated nucleic acid molecule which encodes a protein comprising about 200 to about 600 consecutive C terminal amino acid residues of SEQ ID NO. 6.

3. An isolated nucleic acid molecule of claim 1 or 2, wherein the nucleic acid molecule is a DNA molecule.

4. An isolated nucleic acid molecule of claim 1 or 2, wherein the nucleic acid molecule is a cDNA molecule.

5. An isolated nucleic acid molecule of claim 1 or 2 wherein the nucleic acid molecule is a DNA molecule operatively linked to a promoter which in turn is encompassed in an expression vector.

6. A host vector system for the production of an amino acid molecule which is the mitosin protein or biologically active fragment thereof which comprises the vector of claim 5 in a suitable host cell.

7. A host vector system of claim 6 wherein the host cell is a mammalian cell.

8. A method of producing recombinant mitosin, which comprises the steps of growing the host vector system of claim 6 under suitable conditions such that the nucleic acid encoding mitosin is expressed and purifying the mitosin so produced.

* * * * *